United States Patent
Van Peij et al.

(10) Patent No.: US 9,745,563 B2
(45) Date of Patent: Aug. 29, 2017

(54) AMYLASE-DEFICIENT STRAIN

(71) Applicant: DSM IP ASSETS B.V., Heerlen (NL)

(72) Inventors: Noel Nicolaas Maria Elisabeth Van Peij, Echt (NL); Martina Beishuizen, Echt (NL); Peter Jozef Ida Van De Vondervoort, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/407,565

(22) PCT Filed: Jul. 19, 2013

(86) PCT No.: PCT/EP2013/065347
§ 371 (c)(1),
(2) Date: Dec. 12, 2014

(87) PCT Pub. No.: WO2014/013073
PCT Pub. Date: Jan. 23, 2014

(65) Prior Publication Data
US 2015/0166970 A1    Jun. 18, 2015

Related U.S. Application Data

(60) Provisional application No. 61/673,589, filed on Jul. 19, 2012, provisional application No. 61/673,607, filed on Jul. 19, 2012.

(30) Foreign Application Priority Data

Jul. 19, 2012  (EP) .................................... 12177171
Jul. 19, 2012  (EP) .................................... 12177173

(51) Int. Cl.
*A61K 51/00*     (2006.01)
*C12N 9/30*      (2006.01)
*C12P 21/02*     (2006.01)
*C12N 9/04*      (2006.01)
*C12N 9/26*      (2006.01)

(52) U.S. Cl.
CPC ........... *C12N 9/242* (2013.01); *C12N 9/0006* (2013.01); *C12N 9/2408* (2013.01); *C12P 21/02* (2013.01); *C12Y 101/03004* (2013.01); *C12Y 302/01001* (2013.01)

(58) Field of Classification Search
None
See application file for complete search history.

(56) References Cited

U.S. PATENT DOCUMENTS

2005/0032059 A1*  2/2005  Maier .................... C12N 9/242
                                                         435/6.12

FOREIGN PATENT DOCUMENTS

| WO | 8901969 A1 | 3/1989 |
| WO | 03016535 A2 | 2/2003 |
| WO | 2010121933 A1 | 10/2010 |
| WO | 2011009700 A1 | 1/2011 |
| WO | 2012001169 A1 | 1/2012 |

OTHER PUBLICATIONS

International Search Report received in corresponding PCT/EP2013/065347, mailed Oct. 9, 2013.
Takashi et al., "Improvement of Heterologous Protein Production in Aspergillus oryzae by RNA Interference with [alpha]-Amylase Genes", Bioscience, Biotechnology and Biochei Istry, vol. 73, No. 11, Nov. 7, 2009 (Nov. 7, 2009), pp. 2370-2373. XP055044514.
Yuan et al., "Aspergillus niger genome-wide analysis reveals a large number of novel alpha-glucan acting enzymes with unexpected expression profiles", Molecular Genetics and Genomics, Springer, Berlin, DE, vol. 279, No. 6, Mar. 5, 2008 (Mar. 5, 2008), pp. 545-561, XP019630981.
Wirsel et al., "Three Alpha-Amylase Genes of Aspergillus Oryzae Exhibit Identical Intron-Exon Organization", Molecular Microbiology, Wiley-Blackwell Publishing Ltd. GB, vol. 3, No. 1, 1989, pp. 3-14, XP009047054.
Nemoto et al., "Contribution Ratios of amyA, amyB, amyC Genes to High-Level alpha-Amylase Expression in Aspergillus oryzae", Bioscience Biotechnology and Biochei Istry, vol. 76, No. 8, Aug. 7, 2012 (Aug. 7, 2012), pp. 1477-1483, XP055044513.

* cited by examiner

*Primary Examiner* — J. Hines
*Assistant Examiner* — Khatol Shahnan Shah
(74) *Attorney, Agent, or Firm* — McBee Moore Woodward & Vanik IP, LLC; Chester Moore; Susan McBee

(57) ABSTRACT

The present invention relates to a mutant microbial host cell which has been modified, preferably in its genome, to result in a deficiency in the production of a polypeptide having α-amylase activity AmyC or an homologous thereof. It has been surprisingly found that when the mutant microbial host cell according to the invention is used in a method to produce a compound of interest, for example an enzyme, an improved purity of the product is obtained.

17 Claims, 5 Drawing Sheets

SEQUENCE LISTING

```
<160> NUMBER OF SEQ ID NOS: 20

<210> SEQ ID NO 1
<211> LENGTH: 5932
<212> TYPE: DNA
<213> ORGANISM: Aspergillus niger
<220> FEATURE:
<221> NAME/KEY: misc_feature
<223> OTHER INFORMATION: AmyC genomic DNA including 2kb upstream and
      downstream flanking regions

<400> SEQUENCE: 1
caatatcacc aacgctacag aggcggcgtc agcttcggcg ggagcttcca gtcaggctgc        60
agcaaccgcg accaccacgt cgacttcggt atcatatctg cggacaacgc ccacgcctgg       120
tgtccgcaat gttgagcacc caccctatgt gatcaaccat gaccaagaag gccatgatct       180
cagtgtccat gcggtgtcgc cgaatgcaac gcatgttgat ggtgttgagg agtatgatgt       240
gcacggtctc tacggacatc aaggattgaa cgctacctac caaggtctgc ttgaggtctg       300
gtctcataag cggcggccat ttattattgg ccgctcaacc ttcgctggct ctggcaaatg       360
ggcaggccac tggggcggcg acaactattc caaatggtgg tccatgtact actccatctc       420
gcaagccctc tccttctcac ttttcggcat tccgatgttt ggtgcggaca cctgtgggtt       480
taacggaaac tccgatgagg agctctgcaa ccgatggatg caactgtccg cattcttccc       540
attctaccga aaccacaatg agctctccac aatcccacag gagccttatc ggtgggcttc       600
tgttattgaa gcaaccaagt ccgccatgag aattcggtac gccatcctac cttactttta       660
tacgttgttt gacctggccc acaccacggg ctccactgta atgcgcgcac tttcctggga       720
attccctaat gacccaacat tggctgcggt tgagactcaa ttcatggttg ggccggccat       780
```

```
catggtggtc cggtattgg agcctctggt caatacggtc aagggcgtat tcccaggagt    840
tggacatggc gaagtgtggt acgattggta cacccaggct gcagttgatg cgaagcccgg   900
ggtcaacacg accatttcgg caccattggg ccacatccca gtttatgtac gaggtggaaa   960
catcttgccg atgcaagagc cggcattgac cactcgtgaa gcccggcaaa ccccgtgggc  1020
tttgctagct gcactaggaa gcaatggaac cgcgtcgggg cagctctatc tcgatgatgg  1080
agagagcatc tacccaatg ccaccctcca tgtggacttc acggcatcgc ggtcaagcct   1140
gcgctcgtcg gctcaaggaa gatggaaaga gaggaacccg cttgctaatg tgacggtgct  1200
cggagtgaac aaggagccct ctgcggtgac cctgaatgga caggccgtat ttcccgggtc  1260
tgtcacgtac aattctacgt cccaggttct ctttgttggg gggctgcaaa acttgacgaa  1320
gggcggcgca tgggcggaaa actgggtatt ggaatggtag tgtcagccac aagccaggtg  1380
tgcgcgtaca gcatgcaaca tgggaacgat gctctgcaat gtagctcttt ggttataatt  1440
caaaattcaa cttccacctt tgtttcaccg gcggccacgg cattcctgca tgactaacgt  1500
tctgtaaatg gacccgataa cacccagcac gttgcagcag agaaggtact ctctcacacg  1560
cactgctctt tatagttgcc gagacggccg ccgaggagaa aaccgccggc ctgtggccac  1620
tattcgctgg aaggaaccct gccagtcgaa cacacccgcc cgtgatcgcc aggggccgat  1680
ggatttcccc ccgcatcctt gtcggttcat gagtgaagac tttaaatccc atctagctga  1740
cggtcgggta catcaataac tggcagccta gtttccaaga cacggagaag catgtaatcg  1800
ctatttatag aatgctggga tcggacccgt cgaatggtct tccgatggga agtgacaact  1860
cacattgtca tgttggcctt actcaatcca acgggatctg acctgctttg gctaacctag  1920
tataaatcag catgtctctc ctttgataca tcggatcgtt cctcaaatat agttatatct  1980
tcgaaaaatt gacaagaagg atgacaatct ttctgtttct ggccattttc gtggctacag  2040
ctctggcagc cacgcctgca gaatggcgct cccagtcgat atatttcctg ctcaccgatc  2100
gctttgcgcg aacggataat tctaccactg cttcttgtga cttgagcgct cgggttagtc  2160
acagcatgtt ctagaatctc caattgattc gctgacagat ctagcaatat tgcggtggat  2220
cctggcaggg catcatcaat caggtcggtc cgtccatcgt tgcagcacta tctacatcaa  2280
cgtttgtttg gcaaattaac atccattagc tggactatat tcaaggaatg ggctttacag  2340
cgatctggat cacacccgta actgcacaga tcccccaaga tactggttac ggacaggcat  2400
atcacggata ctggcagcag gacgcgtgag atgctacctc tatcgcccgg atgaatgtat  2460
atccttctta ccatgcagac agttatgccc tgaactccca ttatggtacg gcagacgatc  2520
tcaaagctct ggcttcagct cttcactcac ggggcatgta tctcatggtg gacgttgttg  2580
ccaatcacat ggtatgttct tagcctccca cgggaccta  gctttatatc tgacagcgat  2640
agggccacaa tggtacgggg agctctgtgg actacagtgt ttataggcca tttaattcgc  2700
aaaagtactt tcacaacctc tgttggatct ctgattacaa taaccagaca aacgttgaag  2760
actgctggct aggcgataac accgttgcct tgccggatct tgatactacc agtacggagg  2820
tgaagaatat gtggtatgac tgggtcgagt ctctcgtctc taactactcc ggtaatccta  2880
cctttacttc gctattttct gcctcttatg agacaaagac taacaaatat caagtcgacg  2940
gcctccgcgt agacacagtc aagaacgtac agaagaactt ctggcccggc tacaacaatg  3000
cttcaggcgt gtactgtatt ggagaagtct tcgatgggga cgcctcatac acctgtcctt  3060
atcaggaaga cttggacgga gtccttaatt accccatgta agcctacat  ttaaccccat   3120 tgaatgcttg ccaacgactt gcaataggta ctatccactc ctccgggctt tcgaatccac  3180
```

```
caacggcagt atcagcgacc tctataacat gatcaacacc gtgaaatcca cctgcagaga   3240
ttctacgctt ctagggacct tcgtcgaaaa ccacgataac ccacgctttg ccaagtaaga   3300
atatcctctc cgagttcacc attacaaaca caagagctca cctcagaagc tacacaagcg   3360
acatgtccct agccaaaaat gccgcaacat tcactatcct ggctgacggc attcccatca   3420
tatacgccgg tcaggaacag cactatagcg gcggtaatga cccctacaac cgcgaagcga   3480
cctggctttc aggctacaag accaccagcg agctctacac ccatatcgcc gcatcgaaca   3540
agattcgcac ccacgctata aaacaggata ccggatatct cacctacaaa gtaatcttca   3600
ttcgagtcca tgtgtggtac aatctatctg actagaacct attctagaac taccccatct   3660
accaagacac ctcgacccct gccatgcgca aaggctacaa tggcacccaa actatcacgg   3720
tcctttctaa ccttggcgcc tcggggtcct catacacact ctccctccca ggaacaggct   3780
acacagccgg ccaaaagatt actgaaatct atacctgcac gaatctaaca gtcaactcaa   3840
atggctcggt gccagtaccc atgaagagcg ggttaccgcg gatcctctat cctgcagata   3900
agttggttaa tggaagctca ttttgcagtt agttccctgc ctatatgttt caataagccg   3960
tatttgcatg cgcgtccatc gcattgattc tttatggatt gatcaactga tacattcgca   4020
caggctctgc gatcactgtt ttcaaggatg caggaggagg cgtgttgttc tttagctaca   4080
ctgtgtaagt gtatcagatc atatcatggc cactagacga tgaccccgt gatcgtgatc    4140 cagatgctga cttcaatttg tagaattttc gctcaggtgc ttattgctat aatgacgtga   4200
ttaggatgtc tcagatgaca gtatatatta ttaggtgacg tgatgattct atgtgtaatg   4260
gattcttcaa gatcatttta tattattagt atccacagta ttcatttgcc tgcaaagtaa   4320
gtatggataa aatcactacc accgacgtag tagttgtacc tagtccttag tgtctcaaag   4380
ccacagtcac tacaacctca cgaaacgacg gagtaaactt atttctattg acacccagcc   4440
aataccaaca acagcagacc aatagtaaat tcaacctcaa cctctgcatc atacaaacat   4500
actagagaaa tatacttcat cataaaaaaa gaaaaggaaa gaaaagaaac aaaaacccct   4560
acttatctcc atcaagtatc tacatccgaa cccaaccatc tacgggcggg gcaagcgaga   4620
tgaacaacac ctcctactgc ctgcagcata gtagcatcat cccgtcaatt tccttccaaa   4680
agttacacct acattcacag caacataaca atacccaact cccctaccct cctctccaag   4740
ttttaattaa tccagataat taattggaga gaaaagttta tttctctaat cccgtccccc   4800
ctctccttcc tctcctcatc atgaaaagat aactaactag caatgatcga cttaataatt   4860
ctcggcggca tcctccggct cccacccact cactttcctc tcctcggcaa ctggttagat   4920
agttacttac tactatgtgc agtcaacgga tagtggagta aagggtcaa agacatacta    4980 ctactactac ttagtctacc tgaacgtttt tgtttggtcg atcggagaaa taaacatctt   5040
gtcttcgatg aatgattact ctttcctaaa tagtagttta ctaaaatgct gagggtaag    5100 ttagttagca agcactgact tgttcgtctc tctgctgcct tggaaaagaa acgatagaaa   5160
cgaaaagaat gtgttctgac tcgttcaact ctccgcggag gcacggaacg gtccgaacaa   5220
aggaggaaag cgtacgtttc ggagatatat ccgattagga aatggtggct ggctggcttc   5280
ctgcagctgg tggtcagtag gagttagtag tttggcatgt gaatgtgaga gtgtctatgg   5340
ggttgtttaa gttgcaagga agcaaaagcg ctcaattacg tgatgtttcg tggcacgggc   5400
cctctaacta aataggcctg tgcaggaagg caacctgatg gatccggtgg tggtggtggt   5460
agtggatcgt gtggaattat attattttat tttagtattt acttggcctt ggttatgatc   5520
```

```
ctttcgttgc acgtcatcat gctaggttcg gggttttagt tcagcccatg ggcaggaact    5580
aaaccaccgc tgcaggttat catccctggt gttactgcta ctaccaccac cacccccact    5640
catgtccttt ccaacccgat ctcgattact tacagcgtcg ctgaccgata cgctgctagc    5700
ccagtcacag gcattccgtt gagtatccca tccggaaagg aactcggcat gacttctggc    5760
atcagttgct cgaagccgta cccctcgatc atgccatcca tgagcggtgg catgaacggt    5820
gcttgcccca tgctcatctt acgactgtcg ccgtaggatg ataacggaga ccccttgaca    5880
gtggatgatg ggtcattgca ttccgcactg ccacatcgcc gcttgaactc gg           5932
```

<210> SEQ ID NO 2
<211> LENGTH: 1482
<212> TYPE: DNA
<213> ORGANISM: Aspergillus niger
<220> FEATURE:
<221> NAME/KEY: misc_feature
<223> OTHER INFORMATION: AmyC cDNA

<400> SEQUENCE: 2

```
atgacaatct ttctgtttct ggccattttc gtggctacag ctctggcagc cacgcctgca      60
gaatggcgct cccagtcgat atatttcctg ctcaccgatc gctttgcgcg aacggataat     120
tctaccactg cttcttgtga cttgagcgct cggcaatatt gcggtggatc ctggcagggc     180
atcatcaatc agctggacta tattcaagga atgggcttta cagcgatctg gatcacaccc     240
gtaactgcac agatccccca agatactggt tacggacagg catatcacgg atactggcag     300
caggacgctt atgccctgaa ctcccattat ggtacggcag acgatctcaa agctctggct     360
tcagctcttc actcacgggg catgtatctc atggtggacg ttgttgccaa tcacatgggc     420
cacaatggta cggggagctc tgtggactac agtgtttata ggccatttaa ttcgcaaaag     480
tactttcaca acctctgttg gatctctgat tacaataacc agacaaacgt tgaagactgc     540
tggctaggcg ataacaccgt tgccttgccg gatcttgata ctaccagtac ggaggtgaag     600
aatatgtggt atgactgggt cgagtctctc gtctctaact actccgtcga cggcctccgc     660
gtagacacag tcaagaacgt acagaagaac ttctggcccg gctacaacaa tgcttcaggc     720
gtgtactgta ttggagaagt cttcgatggg gacgcctcat acacctgtcc ttatcaggaa     780
gacttggacg gagtccttaa ttaccccatg tactatccac tcctccgggc tttcgaatcc     840
accaacggca gtatcagcga cctctataac atgatcaaca ccgtgaaatc cacctgcaga     900
gattctacgc ttctagggac cttcgtcgaa aaccacgata cccacgcctt gccaactac     960 acaagcgaca tgtccctagc caaaaatgcc gcaacattca ctatcctggc tgacggcatt    1020
cccatcatat acgccggtca ggaacagcac tatagcggcg gtaatgaccc ctacaaccgc    1080
gaagcgacct ggcttcagg ctacaagacc accagcgagc tctacaccca tcgccgca      1140 tcgaacaaga ttcgcacccca cgctataaaa caggataccg atatctcac ctacaaaaac   1200 taccccatct accaagacac ctcgacccct gccatgcgca aaggctacaa tggcacccaa    1260
actatcacgg tccttttctaa ccttggcgcc tcgggttcct catacacact ctcctccca    1320 ggaacaggct acacagccgg ccaaaagatt actgaaatct atacctgcac gaatctaaca    1380
gtcaactcaa atggctcggt gccagtaccc atgaagagcg ggttaccgcg gatcctctat    1440
cctgcagata agttggttaa tggaagctca ttttgcagtt ag                        1482
```

<210> SEQ ID NO 3
<211> LENGTH: 493
<212> TYPE: PRT

```
<213> ORGANISM: Aspergillus niger
<220> FEATURE:
<221> NAME/KEY: misc_feature
<223> OTHER INFORMATION: AmyC protein

<400> SEQUENCE: 3
```

| | | | | | | | | | | | | | | |
|---|---|---|---|---|---|---|---|---|---|---|---|---|---|---|
| Met | Thr | Ile | Phe | Leu | Phe | Leu | Ala | Ile | Phe | Val | Ala | Thr | Ala | Leu | Ala |
| 1 | | | | 5 | | | | | 10 | | | | | 15 | |

Ala Thr Pro Ala Glu Trp Arg Ser Gln Ser Ile Tyr Phe Leu Leu Thr
            20                  25                  30

Asp Arg Phe Ala Arg Thr Asp Asn Ser Thr Thr Ala Ser Cys Asp Leu
            35                  40                  45

Ser Ala Arg Gln Tyr Cys Gly Gly Ser Trp Gln Gly Ile Ile Asn Gln
 50                  55                  60

Leu Asp Tyr Ile Gln Gly Met Gly Phe Thr Ala Ile Trp Ile Thr Pro
 65                  70                  75                  80

Val Thr Ala Gln Ile Pro Gln Asp Thr Gly Tyr Gly Gln Ala Tyr His
                85                  90                  95

Gly Tyr Trp Gln Gln Asp Ala Tyr Ala Leu Asn Ser His Tyr Gly Thr
               100                 105                 110

Ala Asp Asp Leu Lys Ala Leu Ala Ser Ala Leu His Ser Arg Gly Met
               115                 120                 125

Tyr Leu Met Val Asp Val Val Ala Asn His Met Gly His Asn Gly Thr
130                 135                 140

Gly Ser Ser Val Asp Tyr Ser Val Tyr Arg Pro Phe Asn Ser Gln Lys
145                 150                 155                 160

Tyr Phe His Asn Leu Cys Trp Ile Ser Asp Tyr Asn Asn Gln Thr Asn
               165                 170                 175

Val Glu Asp Cys Trp Leu Gly Asp Asn Thr Val Ala Leu Pro Asp Leu
               180                 185                 190

Asp Thr Thr Ser Thr Glu Val Lys Asn Met Trp Tyr Asp Trp Val Glu
               195                 200                 205

Ser Leu Val Ser Asn Tyr Ser Val Asp Gly Leu Arg Val Asp Thr Val
210                 215                 220

Lys Asn Val Gln Lys Asn Phe Trp Pro Gly Tyr Asn Asn Ala Ser Gly
225                 230                 235                 240

Val Tyr Cys Ile Gly Glu Val Phe Asp Gly Asp Ala Ser Tyr Thr Cys
               245                 250                 255

Pro Tyr Gln Glu Asp Leu Asp Gly Val Leu Asn Tyr Pro Met Tyr Tyr
               260                 265                 270

Pro Leu Leu Arg Ala Phe Glu Ser Thr Asn Gly Ser Ile Ser Asp Leu
               275                 280                 285

Tyr Asn Met Ile Asn Thr Val Lys Ser Thr Cys Arg Asp Ser Thr Leu
290                 295                 300

Leu Gly Thr Phe Val Glu Asn His Asp Asn Pro Arg Phe Ala Asn Tyr
305                 310                 315                 320

Thr Ser Asp Met Ser Leu Ala Lys Asn Ala Ala Thr Phe Thr Ile Leu
               325                 330                 335

Ala Asp Gly Ile Pro Ile Ile Tyr Ala Gly Gln Glu Gln His Tyr Ser
               340                 345                 350

Gly Gly Asn Asp Pro Tyr Asn Arg Glu Ala Thr Trp Leu Ser Gly Tyr
               355                 360                 365

Lys Thr Thr Ser Glu Leu Tyr Thr His Ile Ala Ala Ser Asn Lys Ile
370                 375                 380

```
Arg Thr His Ala Ile Lys Gln Asp Thr Gly Tyr Leu Thr Tyr Lys Asn
385                 390                 395                 400

Tyr Pro Ile Tyr Gln Asp Thr Ser Thr Leu Ala Met Arg Lys Gly Tyr
                405                 410                 415

Asn Gly Thr Gln Thr Ile Thr Val Leu Ser Asn Leu Gly Ala Ser Gly
            420                 425                 430

Ser Ser Tyr Thr Leu Ser Leu Pro Gly Thr Gly Tyr Thr Ala Gly Gln
        435                 440                 445

Lys Ile Thr Glu Ile Tyr Thr Cys Thr Asn Leu Thr Val Asn Ser Asn
449 450                 455                 460

Gly Ser Val Pro Val Pro Met Lys Ser Gly Leu Pro Arg Ile Leu Tyr
465                 470                 475                 480

Pro Ala Asp Lys Leu Val Asn Gly Ser Ser Phe Cys Ser
                485                 490

<210> SEQ ID NO 4
<211> LENGTH: 477
<212> TYPE: PRT
<213> ORGANISM: Aspergillus niger
<220> FEATURE:
<221> NAME/KEY: misc_feature
<223> OTHER INFORMATION: AmyC mature protein

<400> SEQUENCE: 4

Ala Thr Pro Ala Glu Trp Arg Ser Gln Ser Ile Tyr Phe Leu Leu Thr
1               5                   10                  15

Asp Arg Phe Ala Arg Thr Asp Asn Ser Thr Thr Ala Ser Cys Asp Leu
                20                  25                  30

Ser Ala Arg Gln Tyr Cys Gly Gly Ser Trp Gln Gly Ile Ile Asn Gln
            35                  40                  45

Leu Asp Tyr Ile Gln Gly Met Gly Phe Thr Ala Ile Trp Ile Thr Pro
50                  55                  60

Val Thr Ala Gln Ile Pro Gln Asp Thr Gly Tyr Gly Gln Ala Tyr His
65                  70                  75                  80

Gly Tyr Trp Gln Gln Asp Ala Tyr Ala Leu Asn Ser His Tyr Gly Thr
                85                  90                  95

Ala Asp Asp Leu Lys Ala Leu Ala Ser Ala Leu His Ser Arg Gly Met
                100                 105                 110

Tyr Leu Met Val Asp Val Val Ala Asn His Met Gly His Asn Gly Thr
            115                 120                 125

Gly Ser Ser Val Asp Tyr Ser Val Tyr Arg Pro Phe Asn Ser Gln Lys
130                 135                 140

Tyr Phe His Asn Leu Cys Trp Ile Ser Asp Tyr Asn Asn Gln Thr Asn
145                 150                 155                 160

Val Glu Asp Cys Trp Leu Gly Asp Asn Thr Val Ala Leu Pro Asp Leu
                165                 170                 175

Asp Thr Thr Ser Thr Glu Val Lys Asn Met Trp Tyr Asp Trp Val Glu
                180                 185                 190

Ser Leu Val Ser Asn Tyr Ser Val Asp Gly Leu Arg Val Asp Thr Val
            195                 200                 205

Lys Asn Val Gln Lys Asn Phe Trp Pro Gly Tyr Asn Asn Ala Ser Gly
210                 215                 220

Val Tyr Cys Ile Gly Glu Val Phe Asp Gly Asp Ala Ser Tyr Thr Cys
225                 230                 235                 240

Pro Tyr Gln Glu Asp Leu Asp Gly Val Leu Asn Tyr Pro Met Tyr Tyr
                245                 250                 255
```

```
Pro Leu Leu Arg Ala Phe Glu Ser Thr Asn Gly Ser Ile Ser Asp Leu
            260                 265                 270

Tyr Asn Met Ile Asn Thr Val Lys Ser Thr Cys Arg Asp Ser Thr Leu
        275                 280                 285

Leu Gly Thr Phe Val Glu Asn His Asp Asn Pro Arg Phe Ala Asn Tyr
    290                 295                 300

Thr Ser Asp Met Ser Leu Ala Lys Asn Ala Ala Thr Phe Thr Ile Leu
305                 310                 315                 320

Ala Asp Gly Ile Pro Ile Ile Tyr Ala Gly Gln Glu Gln His Tyr Ser
                325                 330                 335

Gly Gly Asn Asp Pro Tyr Asn Arg Glu Ala Thr Trp Leu Ser Gly Tyr
            340                 345                 350

Lys Thr Thr Ser Glu Leu Tyr Thr His Ile Ala Ala Ser Asn Lys Ile
        355                 360                 365

Arg Thr His Ala Ile Lys Gln Asp Thr Gly Tyr Leu Thr Tyr Lys Asn
    370                 375                 380

Tyr Pro Ile Tyr Gln Asp Thr Ser Thr Leu Ala Met Arg Lys Gly Tyr
385                 390                 395                 400

Asn Gly Thr Gln Thr Ile Thr Val Leu Ser Asn Leu Gly Ala Ser Gly
                405                 410                 415

Ser Ser Tyr Thr Leu Ser Leu Pro Gly Thr Gly Tyr Thr Ala Gly Gln
            420                 425                 430

Lys Ile Thr Glu Ile Tyr Thr Cys Thr Asn Leu Thr Val Asn Ser Asn
        435                 440                 445

Gly Ser Val Pro Val Pro Met Lys Ser Gly Leu Pro Arg Ile Leu Tyr
    450                 455                 460

Pro Ala Asp Lys Leu Val Asn Gly Ser Ser Phe Cys Ser
465                 470                 475

<210> SEQ ID NO 5
<211> LENGTH: 5932
<212> TYPE: DNA
<213> ORGANISM: Aspergillus niger
<220> FEATURE:
<221> NAME/KEY: misc_feature
<223> OTHER INFORMATION: AmyC genomic DNA including 2kb upstream and
      downstream flanking regions

<400> SEQUENCE: 5
caatatcacc aacgctacag aggcggcgtc agcttcggcg ggagcttcca gtcaggctgc      60
agcaaccgcg accaccacgt cgacttcggt atcatatctg cggacaacgc ccacgcctgg    120
tgtccgcaat gttgagcacc caccctatgt gatcaaccat gaccaagaag gccatgatct    180
cagtgtccat gcggtgtcgc cgaatgcaac gcatgttgat ggtgttgagg agtatgatgt    240
gcacggtctc tacggacatc aaggattgaa cgctacctac caaggtctgc ttgaggtctg    300
gtctcataag cggcggccat ttattattgg ccgctcaacc ttcgctggct ctggcaaatg    360
ggcaggccac tggggcggcg acaactattc aaatggtgg tccatgtact actccatctc    420
gcaagccctc tccttctcac ttttcggcat tccgatgttt ggtgcggaca cctgtgggtt    480
taacggaaac tccgatgagg agctctgcaa ccgatggatg caactgtccg cattcttccc    540
attctaccga aaccacaatg agctctccac aatcccacag gagcctatc ggtgggcttc     600 tgttattgaa gcaaccaagt ccgccatgag aattcggtac gccatcctac cttacttta    660 tacgttgttt gacctggccc acaccacggg ctccactgta atgcgcgcac tttcctggga    720
```

```
attccctaat gacccaacat tggctgcggt tgagactcaa ttcatggttg ggccggccat      780
catggtggtc ccggtattgg agcctctggt caatacggtc aagggcgtat tcccaggagt      840
tggacatggc gaagtgtggt acgattggta cacccaggct gcagttgatg cgaagcccgg      900
ggtcaacacg accatttcgg caccatgggg ccacatccca gtttatgtac gaggtggaaa      960
catcttgccg atgcaagagc cggcattgac cactcgtgaa gcccggcaaa cccgtgggc     1020 tttgctagct gcactaggaa gcaatggaac cgcgtcgggg cagctctatc tcgatgatgg     1080
agagagcatc tacccaatg ccaccctcca tgtggacttc acggcatcgc ggtcaagcct      1140
gcgctcgtcg gctcaaggaa gatggaaaga gaggaacccg cttgctaatg tgacggtgct     1200
cggagtgaac aaggagccct ctgcggtgac cctgaatgga caggccgtat tcccgggtc      1260 tgtcacgtac aattctacgt cccaggttct ctttgttggg gggctgcaaa acttgacgaa     1320
gggcggcgca tgggcggaaa actgggtatt ggaatggtag tgtcagccac aagccaggtg     1380
tgcgcgtaca gcatgcaaca tgggaacgat gctctgcaat gtagctcttt ggttataatt     1440
caaaattcaa cttccacctt tgtttcaccg gcggccacgg cattcctgca tgactaacgt     1500
tctgtaaatg gacccgataa cacccagcac gttgcagcag agaaggtact ctctcacacg     1560
cactgctctt tatagttgcc gagacggccg ccgaggagaa aaccgccggc ctgtggccac     1620
tattcgctgg aaggaaccct gccagtcgaa cacacccgcc cgtgatcgcc aggggccgat     1680
ggatttcccc ccgcatcctt gtcggttcat gagtgaagac tttaaatccc atctagctga     1740
cggtcgggta catcaataac tggcagccta gtttccaaga cacggagaag catgtaatcg     1800
ctatttatag aatgctggga tcggacccgt cgaatggtct tccgatggga agtgacaact     1860
cacattgtca tgttggcctt actcaatcca acgggatctg acctgctttg gctaacctag     1920
tataaatcag catgtctctc ctttgataca tcggatcgtt cctcaaatat agttatatct     1980
tcgaaaaatt gacaagaagg atgacaatct ttctgtttct ggccattttc gtggctacag     2040
ctctggcagc cacgcctgca gaatggcgct cccagtcgat atatttcctg ctcaccgatc     2100
gctttgcgcg aacggataat tctaccactg cttcttgtga cttgagcgct cgggttagtc     2160
acagcatgtt ctagaatctc caattgattc gctgacagat ctagcaatat tgcggtggat     2220
cctggcaggg catcatcaat caggtcggtc cgtccatcgt tgcagcacta tctacatcaa     2280
cgtttgtttg gcaaattaac atccattagc tggactatat tcaaggaatg ggctttacag     2340
cgatctggat cacacccgta actgcacaga tcccccaaga tactggttac ggacaggcat     2400
atcacggata ctgcagcag gacgcgtgag atgctacctc tatcgcccgg atgaatgtat      2460
atccttctta ccatgcagac agttatgccc tgaactccca ttatggtacg gcagacgatc     2520
tcaaagctct ggcttcagct cttcactcac ggggcatgta tctcatggtg gacgttgttg     2580
ccaatcacat ggtatgttct tagcctccca cgggacctta gctttatatc tgacagcgat     2640
agggccacaa tggtacgggg agctctgtgg actacagtgt ttataggcca tttaattcgc     2700
aaaagtactt tcacaacctc tgttggatct ctgattacaa taaccagaca aacgttgaag     2760
actgctggct aggcgataac accgttgcct tgccggatct tgatactacc agtacggagg     2820
tgaagaatat gtggtatgac tgggtcgagt ctctcgtctc taactactcc ggtaatccta     2880
cctttacttc gctattttct gcctcttatg agacaaagac taacaaatat caagtcgacg     2940
gcctccgcgt agacacagtc aagaacgtac agaagaactt ctggcccggc tacaacaatg     3000
cttcaggcgt gtactgtatt ggagaagtct tcgatgggga cgcctcatac acctgtcctt     3060
atcaggaaga cttggacgga gtccttaatt accccatgta agccctacat ttaaccccat     3120
```

```
tgaatgcttg ccaacgactt gcaataggta ctatccactc ctccgggctt tcgaatccac    3180
caacggcagt atcagcgacc tctataacat gatcaacacc gtgaaatcca cctgcagaga    3240
ttctacgctt ctagggacct tcgtcgaaaa ccacgataac ccacgctttg ccaagtaaga    3300
atatcctctc cgagttcacc attacaaaca caagagctca cctcagaagc tacacaagcg    3360
acatgtccct agccaaaaat gccgcaacat tcactatcct ggctgacggc attcccatca    3420
tatacgccgg tcaggaacag cactatagcg gcggtaatga ccctacaac cgcgaagcga     3480 cctggctttc aggctacaag accaccagcg agctctacac ccatatcgcc gcatcgaaca    3540
agattcgcac ccacgctata aacaggata ccggatatct cacctacaaa gtaatcttca     3600
ttcgagtcca tgtgtggtac aatctatctg actagaacct attctagaac taccccatct    3660
accaagacac ctcgacccct tgccatgcgca aaggctacaa tggcacccaa actatcacgg    3720
tccttcctaa ccttggcgcc tcggggtcct catacacact ctccctccca ggaacaggct    3780
acacagccgg ccaaaagatt actgaaatct atacctgcac gaatctaaca gtcaactcaa    3840
atggctcggt gccagtaccc atgaagagcg ggttaccgcg gatcctctat cctgcagata    3900
agttggttaa tggaagctca ttttgcagtt agttccctgc ctatatgttt caataagccg    3960
tatttgcatg cgcgtccatc gcattgattc tttatggatt gatcaactga tacattcgca    4020
caggctctgc gatcactgtt ttcaaggatg caggaggagg cgtgttgttc tttagctaca    4080
ctgtgtaagt gtatcagatc atatcatggc cactagacga tgacccctgt gatcgtgatc    4140
cagatgctga cttcaatttg tagaatttc gctcaggtgc ttattgctat aatgacgtga     4200
ttaggatgtc tcagatgaca gtatatatta ttaggtgacg tgatgattct atgtgtaatg    4260
gattcttcaa gatcatttta tattattagt atccacagta ttcatttgcc tgcaaagtaa    4320
gtatggataa aatcactacc accgacgtag tagttgtacc tagtccttag tgtctcaaag    4380
ccacagtcac tacaacctca cgaaacgacg gagtaaactt atttctattg acacccagcc    4440
aataccaaca acagcagacc aatagtaaat tcaacctcaa cctctgcatc atacaaacat    4500
actagagaaa tatacttcat cataaaaaaa gaaaagaaa gaaaagaaac aaaaaccccct    4560 acttatctcc atcaagtatc tacatccgaa cccaaccatc tacgggcggg gcaagcgaga    4620
tgaacaacac ctcctactgc ctgcagcata gtagcatcat cccgtcaatt tccttccaaa    4680
agttacacct acattcacag caacataaca atacccaact ccctaccct cctctccaag     4740 ttttaattaa tccagataat taattggaga gaaaagttta tttctctaat cccgtccccc    4800
ctctccttcc tctcctcatc atgaaaagat aactaactag caatgatcga cttaataatt    4860
ctcggcggca tcctccggct cccacccact cactttcctc tcctcggcaa ctggttagat    4920
agttacttac tactatgtgc agtcaacgga tagtggagta aaggggtcaa agacatacta    4980
ctactactac ttagtctacc tgaacgtttt tgtttggtcg atcggagaaa taaacatctt    5040
gtcttcgatg aatgattact ctttcctaaa tagtagttta ctaaaatgct gaggggtaag    5100
ttagttagca agcactgact tgttcgtctc tctgctgcct tggaaaagaa acgatagaaa    5160
cgaaaagaat gtgttctgac tcgttcaact ctccgcggag gcacggaacg gtccgaacaa    5220
aggaggaaag cgtacgtttc ggagatatat ccgattagga aatggtggct ggctggcttc    5280
ctgcagctgg tggtcagtag gagttagtag tttggcatgt gaatgtgaga gtgtctatgg    5340
ggttgtttaa gttgcaagga agcaaaagcg ctcaattacg tgatgtttcg tggcacgggc    5400
cctctaacta aataggcctg tgcaggaagg caacctgatg gatccggtgg tggtggtggt    5460
```

```
agtggatcgt gtggaattat attattttat tttagtattt acttggcctt ggttatgatc    5520
ctttcgttgc acgtcatcat gctaggttcg gggttttagt tcagcccatg ggcaggaact    5580
aaaccaccgc tgcaggttat catccctggt gttactgcta ctaccaccac cacccccact    5640
catgtccttt ccaacccgat ctcgattact tacagcgtcg ctgaccgata cgctgctagc    5700
ccagtcacag gcattccgtt gagtatccca tccggaaagg aactcggcat gacttctggc    5760
atcagttgct cgaagccgta cccctcgatc atgccatcca tgagcggtgg catgaacggt    5820
gcttgcccca tgctcatctt acgactgtcg ccgtaggatg ataacggaga ccccttgaca    5880
gtggatgatg ggtcattgca ttccgcactg ccacatcgcc gcttgaactc gg            5932
```

<210> SEQ ID NO 6
<211> LENGTH: 1575
<212> TYPE: DNA
<213> ORGANISM: Aspergillus niger
<220> FEATURE:
<221> NAME/KEY: misc_feature
<223> OTHER INFORMATION: AmyC cDNA

<400> SEQUENCE: 6

```
atgacaatct ttctgtttct ggccattttc gtggctacag ctctggcagc cacgcctgca     60
gaatggcgct cccagtcgat atatttcctg ctcaccgatc gctttgcgcg aacggataat    120
tctaccactg cttcttgtga cttgagcgct cggcaatatt gcggtggatc ctggcagggc    180
atcatcaatc agctggacta tattcaagga atgggcttta cagcgatctg gatcacaccc    240
gtaactgcac agatccccca agatactggt tacggacagg catatcacgg atactggcag    300
caggacgctt atgccctgaa ctcccattat ggtacggcag acgatctcaa agctctggct    360
tcagctcttc actcacgggg catgtatctc atggtggacg ttgttgccaa tcacatgggc    420
cacaatggta cggggagctc tgtggactac agtgtttata ggccatttaa ttcgcaaaag    480
tactttcaca acctctgttg gatctctgat tacaataacc agacaaacgt tgaagactgc    540
tggctaggcg ataacaccgt tgccttgccg gatcttgata ctaccagtac ggaggtgaag    600
aatatgtggt atgactgggt cgagtctctc gtctctaact actccgtcga cggcctccgc    660
gtagacacag tcaagaacgt tacagaagaac ttctggcccg gctacaacaa tgcttcaggc    720
gtgtactgta ttggagaagt cttcgatggg gacgcctcat acacctgtcc ttatcaggaa    780
gacttggacg gagtccttaa ttaccccatg tactatccac tcctccgggc tttcgaatcc    840
accaacggca gtatcagcga cctctataac atgatcaaca ccgtgaaatc cacctgcaga    900
gattctacgc ttctagggac cttcgtcgaa accacgata acccacgctt tgccaactac    960
acaagcgaca tgtccctagc caaaaatgcc gcaacattca ctatcctggc tgacggcatt   1020
cccatcatat acgccggtca ggaacagcac tatagcggcg taatgacccc ctacaaccgc   1080
gaagcgacct ggctttcagg ctacaagacc accagcgagc tctacaccca tatcgccgca   1140
tcgaacaaga ttcgcacccca cgctataaaa caggataccg gatatctcac ctacaaaaac   1200
taccccatct accaagacac ctcgacccctt gccatgcgca aaggctacaa tggcacccaa   1260
actatcacgg tcctttctaa ccttggcgcc tcggggtcct catacacact ctccctccca   1320
ggaacaggct acacagccgg ccaaaagatt actgaaatct atacctgcac gaatctaaca   1380
gtcaactcaa atggctcggt gccagtaccc atgaagagcg ggttaccgcg gatcctctat   1440
cctgcagata agttggttaa tggaagctca ttttgcagct ctgcgatcac tgttttcaag   1500
gatgcaggag gaggcgtgtt gttctttagc tacactgtaa ttttcgctca ggtgcttatt   1560
```
gctataatga cgtga                                                          1575

<210> SEQ ID NO 7
<211> LENGTH: 524
<212> TYPE: PRT
<213> ORGANISM: Aspergillus niger
<220> FEATURE:
<221> NAME/KEY: misc_feature
<223> OTHER INFORMATION: AmyC protein

<400> SEQUENCE: 7

Met Thr Ile Phe Leu Phe Leu Ala Ile Phe Ala Thr Ala Leu Ala
1               5                   10                  15

Ala Thr Pro Ala Glu Trp Arg Ser Gln Ser Ile Tyr Phe Leu Leu Thr
            20                  25                  30

Asp Arg Phe Ala Arg Thr Asp Asn Ser Thr Thr Ala Ser Cys Asp Leu
            35                  40                  45

Ser Ala Arg Gln Tyr Cys Gly Gly Ser Trp Gln Gly Ile Ile Asn Gln
50                  55                  60

Leu Asp Tyr Ile Gln Gly Met Gly Phe Thr Ala Ile Trp Ile Thr Pro
65                  70                  75                  80

Val Thr Ala Gln Ile Pro Gln Asp Thr Gly Tyr Gly Gln Ala Tyr His
                85                  90                  95

Gly Tyr Trp Gln Gln Asp Ala Tyr Ala Leu Asn Ser His Tyr Gly Thr
            100                 105                 110

Ala Asp Asp Leu Lys Ala Leu Ala Ser Ala Leu His Ser Arg Gly Met
            115                 120                 125

Tyr Leu Met Val Asp Val Val Ala Asn His Met Gly His Asn Gly Thr
130                 135                 140

Gly Ser Ser Val Asp Tyr Ser Val Tyr Arg Pro Phe Asn Ser Gln Lys
145                 150                 155                 160

Tyr Phe His Asn Leu Cys Trp Ile Ser Asp Tyr Asn Asn Gln Thr Asn
                165                 170                 175

Val Glu Asp Cys Trp Leu Gly Asp Asn Thr Val Ala Leu Pro Asp Leu
            180                 185                 190

Asp Thr Thr Ser Thr Glu Val Lys Asn Met Trp Tyr Asp Trp Val Glu
            195                 200                 205

Ser Leu Val Ser Asn Tyr Ser Val Asp Gly Leu Arg Val Asp Thr Val
210                 215                 220

Lys Asn Val Gln Lys Asn Phe Trp Pro Gly Tyr Asn Asn Ala Ser Gly
225                 230                 235                 240

Val Tyr Cys Ile Gly Glu Val Phe Asp Gly Asp Ala Ser Tyr Thr Cys
                245                 250                 255

Pro Tyr Gln Glu Asp Leu Asp Gly Val Leu Asn Tyr Pro Met Tyr Tyr
            260                 265                 270

Pro Leu Leu Arg Ala Phe Glu Ser Thr Asn Gly Ser Ile Ser Asp Leu
            275                 280                 285

Tyr Asn Met Ile Asn Thr Val Lys Ser Thr Cys Arg Asp Ser Thr Leu
290                 295                 300

Leu Gly Thr Phe Val Glu Asn His Asp Asn Pro Arg Phe Ala Asn Tyr
305                 310                 315                 320

Thr Ser Asp Met Ser Leu Ala Lys Asn Ala Ala Thr Phe Thr Ile Leu
                325                 330                 335

Ala Asp Gly Ile Pro Ile Ile Tyr Ala Gly Gln Glu Gln His Tyr Ser
            340                 345                 350

```
Gly Gly Asn Asp Pro Tyr Asn Arg Glu Ala Thr Trp Leu Ser Gly Tyr
            355                 360                 365

Lys Thr Thr Ser Glu Leu Tyr Thr His Ile Ala Ser Asn Lys Ile
370                 375                 380

Arg Thr His Ala Ile Lys Gln Asp Thr Gly Tyr Leu Thr Tyr Lys Asn
385                 390                 395                 400

Tyr Pro Ile Tyr Gln Asp Thr Ser Thr Leu Ala Met Arg Lys Gly Tyr
                405                 410                 415

Asn Gly Thr Gln Thr Ile Thr Val Leu Ser Asn Leu Gly Ala Ser Gly
                420                 425                 430

Ser Ser Tyr Thr Leu Ser Leu Pro Gly Thr Gly Tyr Thr Ala Gly Gln
            435                 440                 445

Lys Ile Thr Glu Ile Tyr Thr Cys Thr Asn Leu Thr Val Asn Ser Asn
            450                 455                 460

Gly Ser Val Pro Val Pro Met Lys Ser Gly Leu Pro Arg Ile Leu Tyr
465                 470                 475                 480

Pro Ala Asp Lys Leu Val Asn Gly Ser Ser Phe Cys Ser Ser Ala Ile
                485                 490                 495

Thr Val Phe Lys Asp Ala Gly Gly Val Leu Phe Phe Ser Tyr Thr
                500                 505                 510

Val Ile Phe Ala Gln Val Leu Ile Ala Ile Met Thr
            515                 520

<210> SEQ ID NO 8
<211> LENGTH: 508
<212> TYPE: PRT
<213> ORGANISM: Aspergillus niger
<220> FEATURE:
<221> NAME/KEY: misc_feature
<223> OTHER INFORMATION: AmyC mature protein

<400> SEQUENCE: 8

Ala Thr Pro Ala Glu Trp Arg Ser Gln Ser Ile Tyr Phe Leu Leu Thr
1               5                   10                  15

Asp Arg Phe Ala Arg Thr Asp Asn Ser Thr Thr Ala Ser Cys Asp Leu
                20                  25                  30

Ser Ala Arg Gln Tyr Cys Gly Gly Ser Trp Gln Gly Ile Ile Asn Gln
            35                  40                  45

Leu Asp Tyr Ile Gln Gly Met Gly Phe Thr Ala Ile Trp Ile Thr Pro
    50                  55                  60

Val Thr Ala Gln Ile Pro Gln Asp Thr Gly Tyr Gly Gln Ala Tyr His
65                  70                  75                  80

Gly Tyr Trp Gln Gln Asp Ala Tyr Ala Leu Asn Ser His Tyr Gly Thr
                85                  90                  95

Ala Asp Asp Leu Lys Ala Leu Ala Ser Ala Leu His Ser Arg Gly Met
                100                 105                 110

Tyr Leu Met Val Asp Val Val Ala Asn His Met Gly His Asn Gly Thr
            115                 120                 125

Gly Ser Ser Val Asp Tyr Ser Val Tyr Arg Pro Phe Asn Ser Gln Lys
130                 135                 140

Tyr Phe His Asn Leu Cys Trp Ile Ser Asp Tyr Asn Asn Gln Thr Asn
145                 150                 155                 160

Val Glu Asp Cys Trp Leu Gly Asp Asn Thr Val Ala Leu Pro Asp Leu
                165                 170                 175

Asp Thr Thr Ser Thr Glu Val Lys Asn Met Trp Tyr Asp Trp Val Glu
                180                 185                 190
```

-continued

Ser Leu Val Ser Asn Tyr Ser Val Asp Gly Leu Arg Val Asp Thr Val
    195                 200                 205

Lys Asn Val Gln Lys Asn Phe Trp Pro Gly Tyr Asn Asn Ala Ser Gly
    210                 215                 220

Val Tyr Cys Ile Gly Glu Val Phe Asp Gly Asp Ala Ser Tyr Thr Cys
225                 230                 235                 240

Pro Tyr Gln Glu Asp Leu Asp Gly Val Leu Asn Tyr Pro Met Tyr Tyr
            245                 250                 255

Pro Leu Leu Arg Ala Phe Glu Ser Thr Asn Gly Ser Ile Ser Asp Leu
            260                 265                 270

Tyr Asn Met Ile Asn Thr Val Lys Ser Thr Cys Arg Asp Ser Thr Leu
            275                 280                 285

Leu Gly Thr Phe Val Glu Asn His Asp Asn Pro Arg Phe Ala Asn Tyr
    290                 295                 300

Thr Ser Asp Met Ser Leu Ala Lys Asn Ala Ala Thr Phe Thr Ile Leu
305                 310                 315                 320

Ala Asp Gly Ile Pro Ile Ile Tyr Ala Gly Gln Glu Gln His Tyr Ser
            325                 330                 335

Gly Gly Asn Asp Pro Tyr Asn Arg Glu Ala Thr Trp Leu Ser Gly Tyr
            340                 345                 350

Lys Thr Thr Ser Glu Leu Tyr Thr His Ile Ala Ala Ser Asn Lys Ile
            355                 360                 365

Arg Thr His Ala Ile Lys Gln Asp Thr Gly Tyr Leu Thr Tyr Lys Asn
    370                 375                 380

Tyr Pro Ile Tyr Gln Asp Thr Ser Thr Leu Ala Met Arg Lys Gly Tyr
385                 390                 395                 400

Asn Gly Thr Gln Thr Ile Thr Val Leu Ser Asn Leu Gly Ala Ser Gly
            405                 410                 415

Ser Ser Tyr Thr Leu Ser Leu Pro Gly Thr Gly Tyr Thr Ala Gly Gln
            420                 425                 430

Lys Ile Thr Glu Ile Tyr Thr Cys Thr Asn Leu Thr Val Asn Ser Asn
    435                 440                 445

Gly Ser Val Pro Val Pro Met Lys Ser Gly Leu Pro Arg Ile Leu Tyr
    450                 455                 460

Pro Ala Asp Lys Leu Val Asn Gly Ser Ser Phe Cys Ser Ser Ala Ile
465                 470                 475                 480

Thr Val Phe Lys Asp Ala Gly Gly Val Leu Phe Ser Tyr Thr
            485                 490                 495

Val Ile Phe Ala Gln Val Leu Ile Ala Ile Met Thr
            500                 505

<210> SEQ ID NO 9
<211> LENGTH: 6909
<212> TYPE: DNA
<213> ORGANISM: Aspergillus niger
<220> FEATURE:
<221> NAME/KEY: misc_feature
<223> OTHER INFORMATION: AgdB genomic DNA including 2kb upstream and
      downstream flanking regions

<400> SEQUENCE: 9
tatgagttat gaagatggtg cgctcttgga acctctgagt gtttctctgg cgggtattga    60
acgtagtggc cttcgcttgg gtgacccatg cctagtcact ggtgctggcc ctattggtct   120
catcaccctg ttgagtgctc gtgctgctgg agctagccct atcgtcatta ccgacatcga   180

| | |
|---|---|
| cgaggggcgg ctggaattcg ccaagtcgct ggtccctgac gttcgcactt acaaggtgca | 240 |
| gattggcctc tctgctgagc agaatgctga aggtatcatc aacgtcttca acgatgggca | 300 |
| aggctcgggc cccggcgctt tgaggcctcg cattgcgatg gagtgcactg gtgtggagag | 360 |
| cagtgttgct tcggcgattt ggagtgtcaa gttcggcggc aaggtcttcg tcattggtgt | 420 |
| cggaaagaac gagatgaccg ttcctttcat gcgcctcagt acttgggaga ttgacctcca | 480 |
| gtaccagtac cggtactgca acacttggcc tcgcgcgatc cgcttggtga ggaacggtgt | 540 |
| tattgacttg aagaagcttg tgacacaccg gttcctcttg gaggatgcga tcaaggcctt | 600 |
| cgaaacggct gccaacccca agacgggagc catcaaggtt caaatcatga gctccgaaga | 660 |
| cgatgtgaag gctgcttccg ctggtcagaa gatttaaaca gtcgtacatt cgtgagcaca | 720 |
| tgcctccact gctttatatt gggtgactgg tcacccttgga tacctttcgc attcatgaca | 780 |
| catatttttc atgacatttt gatggatggt ttatcgtgta acgttcccct tttttatgac | 840 |
| gttgttagag atccctgctg gttggaggca tagagatgca cgtagaattc tattccttca | 900 |
| tttttgactc tcacaacatc tgcatccgac atatcgcagg tagagaagct gtctctcatc | 960 |
| gcattgacaa gcctttgcat agaatgaagc ggcagagtaa cccagagctg cagcttgact | 1020 |
| gaacactttg tcttaacgca tctgcacact tcccccaggt ccccaagctt ctgccagggt | 1080 |
| acccggcctg ctggaggagt gaatatgcac acctcgagtg ccacattaat tagtacgatg | 1140 |
| tggtcaatac cttatgccac ctcattgctt aatgcttgca gcactggcag taagcgaccg | 1200 |
| cctcttgaca ggtcagagcc acctatcagc tacaactacg tatcagcaga ccggatccgt | 1260 |
| tgcatccgac gctttgtctg actcttgtgc ggttttgag tgaccagaat atttactttg | 1320 |
| gtccatgttc tttgagtgag atctgatcct gatcctttga atgtctcagt ttgtttgttt | 1380 |
| gcggggcgtc aggcggggca cgtggtgggg agagtgagga gagccaccat cactgtcact | 1440 |
| tcctcgattc catctccata ctactattcg ctaccaaaag cttacttgca taaaatttgg | 1500 |
| agccaatcat ccagggcatt accgagagat ataccgatta gacgtgccca gagtctaggc | 1560 |
| tgctgcacga gattcaatga acgagaatcg gtgtaagtga cctgatgtta tttggtccct | 1620 |
| gcatcagccc caagccgata gcggcgaaga tccccgataa ttgaccgaga tgggacgacc | 1680 |
| ttagactcac attgtcttct ttaggcaatc gtctccacgt ttctcggctt ttctatccta | 1740 |
| taaatattgc tttttgtttt tcctcataga actgctcggc tcatcccgcc tctttgtcag | 1800 |
| atacattcct tggcttcgct gattgaatct gcggggtccg gtcataccgc gcaacgccac | 1860 |
| attatgcact tcggccaacg cgccatgcat tcaatgtcat cagtccgtgc ccaaacacat | 1920 |
| ataagccgct gggaccaccc agctgggata tgaagtcacg gcttgctgta atccggggtg | 1980 |
| atcccagagc caacatcata atgttggggt ctttgctttt actcttaccc cttgtgggcg | 2040 |
| ctgctgtcat tggacccagg gcaaacagtc agagttgccc agggtataag gcgtccaacg | 2100 |
| tccaaaagca ggctaggtca ctgactgcgg atctgactct agctggtacg ccttgtaata | 2160 |
| gctatggcaa ggatttggaa gacctcaagc tgcttgtgga atatcagact ggtgagtgtt | 2220 |
| ggcttgtgtg aatcaagagt tcctgactaa atgcttgctc agatgaacgg ttacatgtta | 2280 |
| tgatctacga tgccgacgag gaagtctatc aagttcctga atcagtcctt cctcgcgtgg | 2340 |
| gtagtgacga ggactctgag gacagtgttt tggaatttga ctatgtggaa gaaccgtttt | 2400 |
| cattcaccat ctccaaggga gatgaggtcc tgtttgactc ttcggcatca ccactagttt | 2460 |
| ttcagtcgca atatgtgaac cttcgcacct ggttgcccga tgatccctat gtgtatggtc | 2520 |
| tcggagagca ttctgaccct atgcgcttgc caacatacaa ttacacgcgg acccttggga | 2580 |

```
accgcgacgc gtatggcact ccaaacaaca ccaacttgta cggtagtcat cctgtctact    2640
atgatcaccg tggaaagtcc ggaacttatg gagtcttcct gctgaactct aatggtatgg    2700
acatcaagat caaccaaacg acagatggaa agcagtactt ggaatacaat cttctcggcg    2760
gtgttctgga cttctacttc ttctacggag aagatcctaa gcaagcgagc atggaatact    2820
caaagattgt cggtctcccg gcaatgcaga gttactggac tttcggcgta tgcccccccac   2880 cccctaatcc cataacagtc cgagttgtat gctgactctt cagttccatc aatgccgtta    2940
tggataccgc gatgtgtatg aacttgccga ggtggtctac aactacagcc aggcaaagat    3000
tcctctggag acgatgtgga cagatatcga ctacatggac aagagaaggg tgtttaccct    3060
tgatcctcag aggttcccgc tcgaaaagat gcgggagttg gtaacctacc tgcacaatca    3120
tgatcagcat tacattgtca tggttgaccc ggctgtgagc gtaagcagtg agtgacttga    3180
cgattcccca tccttgcaac tttcagctaa tggatacttt ctagataaca cggcatatat    3240
caccggcgtg agagacgatg ttttccttca caatcagaac ggtagcctat acgagggtaa    3300
gtatatacac atctcatatc tctcaacacg agctaaacta tgcaggtgct gtttggcctg    3360
gtgtcactgt tttcccagac tggttcaatg agggtactca ggattactgg actgcgcaat    3420
ttcaacagtt ctttgatccc aagtccggag tcgatattga cgccctgtgg attgacatga    3480
acgaagcctc caatttctgc ccttatcctt gtctggaccc agcggcatac gcgatctccg    3540
ccgacctccc accggcagca ccacctgttc ggccaagcag cccgatccca ctgcccggat    3600
tccccgcgga ctttcagcct tcgtctaagc gatctgttaa aagagcgcaa ggagataaag    3660
ggaagaaggt tgggttgccc aatcgcaacc tcactgaccc gccctacacc attcggaatg    3720
ccgcaggtgt ccttagtatg agcactatcg agacggatct cattcatgcg ggtgaagggt    3780
atgccgagta tgatactcac aatctctatg gaacaagtaa gtctttcaaa tatttgcata    3840
gatgatttgc cattgacagg gttagtgatg agctctgctt cccgcacggc tatgcaggcc    3900
cgccgtcccg atgtgaggcc tttggtcatc actcgcagta cgtttgcagg cgctggagca    3960
cacgtaggac actggtaagt tgaccgatag ccttcgctag cacatcgctg attcgtacag    4020
gctgggcgac aactttagcg attgggttca ctaccggatc tccatcgcgc agatcctctc    4080
cttcgcgtcc atgttccaga ttccaatggt cggggctgac gtgtgtgggt ttggtagcaa    4140
cacgacggag gaattgtgtg cccgatgggc gtcacttggt gccttctata cgttctaccg    4200
caatcataac gagctgggcg acatatcgca agagttctac cgctggccta cggttgccga    4260
gtccgcgcgt aaggccattg acatccggta caagctcctc gattatatct acactgctct    4320
tcaccggcaa agccagaccg gcgagccatt cctgcagcct caattctacc tgtaccctga    4380
ggattcgaac acctttgcga acgaccggca gttcttctat ggtgacgccc ttcttgtcag    4440
ccccgtgttg aatgagggat ccacctcagt cgacgcatac ttcccggacg acatcttcta    4500
cgattggtac acaggggcag tggtgcgtgg cacggagaa acatcacgc tcagcaacat    4560 caacatcacc cacatccctc tgcacatccg cggtggaaat atcatacctg tcaggacatc    4620
cagcggcatg acaaccactg aggttcgtaa gcagggcttc gagctgatca tcgcgccaga    4680
cttggatgac accgcatcgg gcagtctata tttggatgat ggagactcgt tgaacccgtc    4740
atctgtgaca gagctcgagt tcacgtacag caaagggag ttgcacgtga agggtacatt    4800
cggacagaag gccgtcccca aggtggagaa atgtaccttg ctggggaagt cagcacggac    4860
gttcaagggc tttgcactcg atgcgccggt gaactttaag ctgaagtagt tagcatatcg    4920
```

| | |
|---|---|
| agttggagtt cagatgagag gggggtaaaa agtagttagt gtctcaggta ccagatcgct | 4980 |
| tacatagtgc ccttactgct aattaagatg attgacatat ctcaataagc ataaactctg | 5040 |
| ccgcagcata cagcaagcac gtagccaggg gacaggcagg aaagccagtg gcagggggatc | 5100 |
| aagggatagg ataagggata cacaccaagg cagtaagcat tcaagccgcg ccaccacaaa | 5160 |
| gatactgtcc aatcctctcc agaggaagaa atgaccgcat aatacgcatc aagccatcca | 5220 |
| catttactcg ccacaccaca atctcataac tcacccaccc aacccaacct gctacataac | 5280 |
| acatgtacca cagtcaatac atacatacca tgtgccagcc gccatgcctc gaacccgcca | 5340 |
| cgcaagggat acagacaatc atcaaacaag gacgggaggc aggcaggacg cgtctacata | 5400 |
| ctacgcacgt accttgcaca tccgtctatc cctactacac gagtcaatcc ttatttccgg | 5460 |
| ggttattcaa atacctaacg gaatcacctc actagctagt aggatttcac catccacttc | 5520 |
| gtttcctctc tcgtttttatc tttctctatt atcttgaagt aaaccggaac aatatgcatc | 5580 |
| tcaaatccat cctcttcacc ctcgccgcat cgactaccct tgtcgccgcc ggcagcgact | 5640 |
| actattgtct catggcgcag gacggcacgg gcatgatcca ggaccgtat tgctgcgata | 5700 |
| gtttctctga tacgccgggg gattcgattg ctaaagttgg gaagaattgt atgtttcagc | 5760 |
| ataccttgtg actgtccttt tttagtggtg ggtcaatgct gatgattgtg tgtttgtcgt | 5820 |
| tgtaggccag tcgatggatg gacttgagtg gacggatcag tgtcctcagg gtggaactgt | 5880 |
| gaagtgttgt tatactattg taagtaaaac accaccatca tgactgtcga agaattgcct | 5940 |
| cgactgggat atgtactaat gaagatgaat gtagggtccc cagttcatct gcacggcaga | 6000 |
| agcagaggag aacacggatg atgattgatt gattgatcta ctattccaca tcatggatgg | 6060 |
| gattatactt tactcgtcca catattcacc cacacaaagc aatgaagtat tcaaactatt | 6120 |
| gtacactaca cctattcctc ccacaccacc acgtctagct agtaaataaa ttaaataact | 6180 |
| ttaaacacta accatcctaa caaacctctc ccccaactcc tccgccgcca acggattcgc | 6240 |
| tcccgtcaac aactccctac aaagcgtcgt cttacccaac ttctcccttc cccctctac | 6300 |
| catcacagcc ccagcatccc tcaactgact ctccaccttc tcaatctccc cctcaacaa | 6360 |
| cgtctccata accttctcct ccgcatcact ccaacacgta atctcatacc ccttatacac | 6420 |
| gaactcccca tccccactaa ccctcgtact caacaacgcc aacggcccat gacaaatcgc | 6480 |
| cgccgtgggc ttattctccc catgaaagta cctcaggatc ctgcccagct ccttatcacc | 6540 |
| acctaggtct acgagcggcg catgtccgcc cgggatgaac accgccgcga aagtcttcaa | 6600 |
| ttcatcgtcg gagatgctag caaagggggcg cggtgaggag aagccgtttt cgcggcgcat | 6660 |
| gcgctcgatg agctcttgct cgcgccggcg ttcgtagaag ttgccggcga aggtgaggag | 6720 |
| ggattcgctg ttcgggtcgg gttgaggggt ttggcccttg ggagaggcga aggtgacttc | 6780 |
| gtggccggcc gagaggagtt tggagagtgg tttggcgagt tcggggagga agaagccggt | 6840 |
| tggttgttgt tgcgtgccgg aggaggtgtt gtgcaggggg aaggaggtcg cgtcgctgag | 6900 |
| gattatgag | 6909 |

<210> SEQ ID NO 10
<211> LENGTH: 2598
<212> TYPE: DNA
<213> ORGANISM: Aspergillus niger
<220> FEATURE:
<221> NAME/KEY: misc_feature
<223> OTHER INFORMATION: AgdB cDNA

<400> SEQUENCE: 10

```
atgttggggt ctttgctttt actcttaccc cttgtgggcg ctgctgtcat ggacccagg      60 gcaaacagtc agagttgccc agggtataag gcgtccaacg tccaaaagca ggctaggtca     120
ctgactgcgg atctgactct agctggtacg ccttgtaata gctatggcaa ggatttggaa     180
gacctcaagc tgcttgtgga atatcagact gatgaacggt tacatgttat gatctacgat     240
gccgacgagg aagtctatca agttcctgaa tcagtccttc ctcgcgtggg tagtgacgag     300
gactctgagg acagtgtttt ggaatttgac tatgtggaag aaccgttttc attcaccatc     360
tccaagggag atgaggtcct gtttgactct tcggcatcac cactagtttt tcagtcgcaa     420
tatgtgaacc ttcgcacctg gttgcccgat gatccctatg tgtatggtct cggagagcat     480
tctgacccta tgcgcttgcc aacatacaat tacacgcgga ccctttggaa ccgcgacgcg     540
tatggcactc caaacaacac caacttgtac ggtagtcatc ctgtctacta tgatcaccgt     600
ggaaagtccg gaacttatgg agtcttcctg ctgaactcta atggtatgga catcaagatc     660
aaccaaacga cagatggaaa gcagtacttg aatacaatc ttctcggcgg tgttctggac     720
ttctacttct tctacggaga agatcctaag caagcgagca tggaatactc aaagattgtc     780
ggtctcccgg caatgcagag ttactggact ttcggcgtat gcccccccacc ccctaatccc     840 ataacagtcc gagttgtggt ctacaactac agccaggcaa agattcctct ggagacgatg     900
tggacagata tcgactacat ggacaagaga agggtgttta cccttgatcc tcagaggttc     960
ccgctcgaaa gatgcgggga gttggtaacc tacctgcaca atcatgatca gcattacatt    1020
gtcatggttg acccggctgt gagcgtaagc aataacacgg catatatcac cggcgtgaga    1080
gacgatgttt tccttcacaa tcagaacggt agcctatacg agggtgctgt ttggcctggt    1140
gtcactgttt tcccagactg gttcaatgag ggtactcagg attactggac tgcgcaattt    1200
caacagttct ttgatcccaa gtccggagtc gatattgacg ccctgtggat tgacatgaac    1260
gaagcctcca atttctgccc ttatccttgt ctggacccag cggcatacgc gatctccgcc    1320
gacctcccac cggcagcacc acctgttcgg ccaagcagcc cgatcccact gcccggattc    1380
cccgcggact ttcagccttc gtctaagcga tctgttaaaa gagcgcaagg agataaaggg    1440
aagaaggttg ggttgcccaa tcgcaacctc actgacccgc cctacaccat tcggaatgcc    1500
gcaggtgtcc ttagtatgag cactatcgag acggatctca ttcatgcggg tgaagggtat    1560
gccgagtatg atactcacaa tctctatgga acaaggttag tgatgagctc tgcttcccgc    1620
acggctatgc aggcccgccg tcccgatgtg aggccttttgg tcatcactcg cagtacgttt    1680
gcaggcgctg gagcacacgt aggacactgg ctgggcgaca actttagcga ttgggttcac    1740
taccggatct ccatcgcgca gatcctctcc ttcgcgtcca tgttccagat tccaatggtc    1800
ggggctgacg tgtgtgggtt tggtagcaac acgacggagg aattgtgtgc ccgatgggcg    1860
tcacttggtg ccttctatac gttctaccgc aatcataacg agctgggcga catatcgcaa    1920
gagttctacc gctggcctac ggttgccgag tccgcgcgta aggccattga catccggtac    1980
aagctcctcg attatatcta cactgctctt caccggcaaa gccagaccgg cgagccattc    2040
ctgcagcctc aattctacct gtaccctgag gattcgaaca cctttgcgaa cgaccggcag    2100
ttcttctatg gtgacgccct tcttgtcagc ccgtgttga atgagggatc cacctcagtc    2160
gacgcatact tcccggacga catcttctac gattggtaca caggggcagt ggtgcgtggg    2220
cacggagaaa acatcacgct cagcaacatc aacatcaccc acatccctct gcacatccgc    2280
ggtggaaata tcatacctgt caggacatcc agcggcatga caaccactga ggttcgtaag    2340
cagggcttcg agctgatcat cgcgccagac ttggatgaca ccgcatcggg cagtctatat    2400
```

```
ttggatgatg gagactcgtt gaacccgtca tctgtgacag agctcgagtt cacgtacagc   2460 aaagggagt tgcacgtgaa gggtacattc ggacagaagg ccgtcgccaa ggtggagaaa   2520
tgtaccttgc tggggaagtc agcacggacg ttcaagggct ttgcactcga tgcgccggtg   2580
aactttaagc tgaagtag                                                2598

<210> SEQ ID NO 11
<211> LENGTH: 865
<212> TYPE: PRT
<213> ORGANISM: Aspergillus niger
<220> FEATURE:
<221> NAME/KEY: misc_feature
<223> OTHER INFORMATION: AgdB protein

<400> SEQUENCE: 11

Met Leu Gly Ser Leu Leu Leu Leu Pro Leu Val Gly Ala Ala Val
1               5                   10                  15

Ile Gly Pro Arg Ala Asn Ser Gln Ser Cys Pro Gly Tyr Lys Ala Ser
            20                  25                  30

Asn Val Gln Lys Gln Ala Arg Ser Leu Thr Ala Asp Leu Thr Leu Ala
        35                  40                  45

Gly Thr Pro Cys Asn Ser Tyr Gly Lys Asp Leu Glu Asp Leu Lys Leu
    50                  55                  60

Leu Val Glu Tyr Gln Thr Asp Glu Arg Leu His Val Met Ile Tyr Asp
65                  70                  75                  80

Ala Asp Glu Glu Val Tyr Gln Val Pro Glu Ser Val Leu Pro Arg Val
                85                  90                  95

Gly Ser Asp Glu Asp Ser Glu Asp Ser Val Leu Glu Phe Asp Tyr Val
            100                 105                 110

Glu Glu Pro Phe Ser Phe Thr Ile Ser Lys Gly Asp Glu Val Leu Phe
        115                 120                 125

Asp Ser Ser Ala Ser Pro Leu Val Phe Gln Ser Gln Tyr Val Asn Leu
    130                 135                 140

Arg Thr Trp Leu Pro Asp Asp Pro Tyr Val Tyr Gly Leu Gly Glu His
145                 150                 155                 160

Ser Asp Pro Met Arg Leu Pro Thr Tyr Asn Tyr Thr Arg Thr Leu Trp
                165                 170                 175

Asn Arg Asp Ala Tyr Gly Thr Pro Asn Asn Thr Asn Leu Tyr Gly Ser
            180                 185                 190

His Pro Val Tyr Tyr Asp His Arg Gly Lys Ser Gly Thr Tyr Gly Val
        195                 200                 205

Phe Leu Leu Asn Ser Asn Gly Met Asp Ile Lys Ile Asn Gln Thr Thr
    210                 215                 220

Asp Gly Lys Gln Tyr Leu Glu Tyr Asn Leu Leu Gly Gly Val Leu Asp
225                 230                 235                 240

Phe Tyr Phe Phe Tyr Gly Glu Asp Pro Lys Gln Ala Ser Met Glu Tyr
                245                 250                 255

Ser Lys Ile Val Gly Leu Pro Ala Met Gln Ser Tyr Trp Thr Phe Gly
            260                 265                 270

Val Cys Pro Pro Pro Asn Pro Ile Thr Val Arg Val Val Tyr
        275                 280                 285

Asn Tyr Ser Gln Ala Lys Ile Pro Leu Glu Thr Met Trp Thr Asp Ile
    290                 295                 300

Asp Tyr Met Asp Lys Arg Arg Val Phe Thr Leu Asp Pro Gln Arg Phe
305                 310                 315                 320
```

```
Pro Leu Glu Lys Met Arg Glu Leu Val Thr Tyr Leu His Asn His Asp
            325                 330                 335

Gln His Tyr Ile Val Met Val Asp Pro Ala Val Ser Val Ser Asn Asn
            340                 345                 350

Thr Ala Tyr Ile Thr Gly Val Arg Asp Val Phe Leu His Asn Gln
        355                 360                 365

Asn Gly Ser Leu Tyr Glu Gly Ala Val Trp Pro Gly Val Thr Val Phe
        370                 375                 380

Pro Asp Trp Phe Asn Glu Gly Thr Gln Asp Tyr Trp Thr Ala Gln Phe
385                 390                 395                 400

Gln Gln Phe Phe Asp Pro Lys Ser Gly Val Asp Ile Asp Ala Leu Trp
                405                 410                 415

Ile Asp Met Asn Glu Ala Ser Asn Phe Cys Pro Tyr Pro Cys Leu Asp
                420                 425                 430

Pro Ala Ala Tyr Ala Ile Ser Ala Asp Leu Pro Pro Ala Ala Pro Pro
            435                 440                 445

Val Arg Pro Ser Ser Pro Ile Pro Leu Pro Gly Phe Pro Ala Asp Phe
        450                 455                 460

Gln Pro Ser Ser Lys Arg Ser Val Lys Arg Ala Gln Gly Asp Lys Gly
465                 470                 475                 480

Lys Lys Val Gly Leu Pro Asn Arg Asn Leu Thr Asp Pro Pro Tyr Thr
            485                 490                 495

Ile Arg Asn Ala Ala Gly Val Leu Ser Met Ser Thr Ile Glu Thr Asp
            500                 505                 510

Leu Ile His Ala Gly Glu Gly Tyr Ala Glu Tyr Asp Thr His Asn Leu
        515                 520                 525

Tyr Gly Thr Arg Leu Val Met Ser Ser Ala Ser Arg Thr Ala Met Gln
        530                 535                 540

Ala Arg Arg Pro Asp Val Arg Pro Leu Val Ile Thr Arg Ser Thr Phe
545                 550                 555                 560

Ala Gly Ala Gly Ala His Val Gly His Trp Leu Gly Asp Asn Phe Ser
            565                 570                 575

Asp Trp Val His Tyr Arg Ile Ser Ile Ala Gln Ile Leu Ser Phe Ala
            580                 585                 590

Ser Met Phe Gln Ile Pro Met Val Gly Ala Asp Val Cys Gly Phe Gly
            595                 600                 605

Ser Asn Thr Thr Glu Glu Leu Cys Ala Arg Trp Ala Ser Leu Gly Ala
        610                 615                 620

Phe Tyr Thr Phe Tyr Arg Asn His Asn Glu Leu Gly Asp Ile Ser Gln
625                 630                 635                 640

Glu Phe Tyr Arg Trp Pro Thr Val Ala Glu Ser Ala Arg Lys Ala Ile
                645                 650                 655

Asp Ile Arg Tyr Lys Leu Leu Asp Tyr Ile Tyr Thr Ala Leu His Arg
            660                 665                 670

Gln Ser Gln Thr Gly Glu Pro Phe Leu Gln Pro Gln Phe Tyr Leu Tyr
        675                 680                 685

Pro Glu Asp Ser Asn Thr Phe Ala Asn Asp Arg Gln Phe Phe Tyr Gly
        690                 695                 700

Asp Ala Leu Leu Val Ser Pro Val Leu Asn Glu Gly Ser Thr Ser Val
705                 710                 715                 720

Asp Ala Tyr Phe Pro Asp Asp Ile Phe Tyr Asp Trp Tyr Thr Gly Ala
            725                 730                 735
```

Val Val Arg Gly His Gly Glu Asn Ile Thr Leu Ser Asn Ile Asn Ile
            740                 745                 750

Thr His Ile Pro Leu His Ile Arg Gly Gly Asn Ile Ile Pro Val Arg
        755                 760                 765

Thr Ser Ser Gly Met Thr Thr Thr Glu Val Arg Lys Gln Gly Phe Glu
    770                 775                 780

Leu Ile Ile Ala Pro Asp Leu Asp Asp Thr Ala Ser Gly Ser Leu Tyr
785                 790                 795                 800

Leu Asp Asp Gly Asp Ser Leu Asn Pro Ser Ser Val Thr Glu Leu Glu
                805                 810                 815

Phe Thr Tyr Ser Lys Gly Glu Leu His Val Lys Gly Thr Phe Gly Gln
            820                 825                 830

Lys Ala Val Pro Lys Val Glu Lys Cys Thr Leu Leu Gly Lys Ser Ala
        835                 840                 845

Arg Thr Phe Lys Gly Phe Ala Leu Asp Ala Pro Val Asn Phe Lys Leu
    850                 855                 860

Lys
865

<210> SEQ ID NO 12
<211> LENGTH: 7124
<212> TYPE: DNA
<213> ORGANISM: Aspergillus niger
<220> FEATURE:
<221> NAME/KEY: misc_feature
<223> OTHER INFORMATION: AgdA genomic DNA including 2kb upstream and
      downstream flanking regions

<400> SEQUENCE: 12
cagtccattg cttgtttaac ggattttgtg acgaattctg ttggtatgta ttctgttgtc    60
gtgataccag gggatgaatg ggcgcaagtg gatataaggt gcggaacttg gggcctttgc   120
gccggagcac atcactgtag gaacaagaaa gaagaaggcg tcgacactta tcgcagggaa   180
gctctctcga gcacttgatc ttacgccgac gacagttgtc gcaggcttgc ttggaggcct   240
tttgtttggt aggggaagga tgagagtcca tttgtatgcg gagacaagtg tgactcccgt   300
cagaacttag cagtagcagc ggcagtggag cgagactctg gagacttcat tgtattttga   360
gaaataacga tactcgtgag acaagtttcg gtggtcaaga tggccacaag gtgagcagtc   420
accgaaaatc atgcgattgc taaggagggg agaccaaag gagagaaatc tggggaaggg   480
cggcgggtaa gcgacaccgt gagaaagtcg gcacctccag gctacccgga ccccgcggta   540
tgagccacct ccattaacct gctacgactg gcctgttcat ttcggcccgt tgctcgagcc   600 aaaggggggta tcacctcgac tggagctact agtcttttag tcccaggatg gcttcctggt   660
ttagcaggtg gaccctccgc ccgagccatg acgcgggtca ggtatactcc agacaggagg   720
ccgaagccat gtccttcaag tgcgagagaa gcgtaggctg aaccatgata tgtcacggag   780
ccatcatcac agatattgcc tcggtatatc cggtagacga ctcgaatcat ttagagactc   840
tttgcgtgta cgtggtgtgg gcatgccatg agttgttggg ccggcctgaa ggatccatca   900
ttgggaccaa gggcatcatc catgcgctac ggagtacttt cggagaatca gcacccctgc   960
acaaagcatt gtcaatgtgt tttcttatgt caaaagctga cagagtctga ggctcgctga  1020
cgatgggatt catgctaatg acggtccgaa agagctttca cgtaacactg gtgaacatcc  1080
cactcgggaa gccgagactt gtgacctact tagtcaaatg agatgattat caaagccatt  1140
aaatgcctcg ctgtcagggg ccctggtaag tgtcttcatt aatcgaaacc catcttcatt  1200

-continued

```
cgtccccgcc ttcagtgctc atcattttag gtttagaagc aagattgagt gccacctgct    1260
ttacaaacca gcatgggtag tctgctgttg aaattcttca ccgggagcat tctggggaag    1320
gtgcaaaagg cggcgcgaag tggtcgggtc gcgattgtag tctggattgg agcacaagaa    1380
tcgtcagagc cgaagcccga actgaggggg tctcggtcat ttatcgggat gagagccaat    1440
cagcgtgcgc tcatcatctg atcgtctggc tgccaggccc ctcaggcatc aatacggtac    1500
tcggcagtat ccactcccgt ttctccggtg caacaaatca tcgttggaga atccccagct    1560
cccccgccaa ctggggtcga tgcttctcca gttgtcctgg tttctcccat gaactcgctt    1620
acgataagct gctgtaccag cccaccagca caacaatatc ttcaatcagg taggtgcttg    1680
ttcgttacct gccccatcct ctcctcttct tcggtcatta tgaactcaat tcggtcgcta    1740
gctttgccga ttctccgcag tccataaaaa tatatctgca tttgccccct acacgtcggg    1800
aattcaccgg cgcaatgagc cttcgggtat ggtcgcacag cgtcatgtca ataggaggct    1860
gctcctagtg gtgatctact agtcgcctca acacagcaat atataaataa caagagcatt    1920
ccttgagcac atctgggtaa tagctgttcc attctcatca aggattacgc gaccgtgcct    1980
cgagcctcct taagcgagcc atggtgaagt tgacgcatct ccttgccaga gcatggcttg    2040
tccctctggc ttatggagcg agccagtcac tcttatccac cactgcccct tcgcagccgc    2100
agtttaccat tcctgcttcc gcagatgtcg gtgcgcagct gattgccaac atcgatgatc    2160
ctcaggctgc cgacgcgcag tcggtttgtc cgggctacaa ggcttcaaaa gtgcagcaca    2220
attcacgtgg attcactgcc agtcttcagc tcgcgggcag gccatgtaac gtatacggca    2280
cagatgttga gtccttgaca ctgtctgtgg agtaccagga ttcggatcga ctgaatattc    2340
agattctccc cactcatgtt gactccacaa acgcttcttg gtactttctt tcggaaaacc    2400
tggtccccag acccaaggct tccctcaatg catctgtatc ccagagcgac ctttttgtgt    2460
catggtcaaa tgagccgtcg ttcaatttca aggtgatccg aaaggctaca ggcgacgcgc    2520
ttttcagtac agaaggcact gtgctcgtat atgagaatca gttcatcgaa tttgtgaccg    2580
cgctccctga agaatataac ttgtatggcc ttggggagca tatcacgcaa ttccgcctcc    2640
agagaaatgc taatctgacc atatatcctt cggatgatgg aacacctatt gaccagtgag    2700
tactgatatc ccgcccgtat cttctggttc tactcttgaa acttactcgt cctagaaacc    2760
tctacggcca acatcccttc tatctggata caagatatta caaggagat aggcagaatg    2820
ggtcttatat tcccgtcaaa agcagcgagg ctgatgcctc gcaagattat atctccctct    2880
ctcatggcgt gtttctgagg aactctcatg gacttgagat actcctccgg tctcaaaaat    2940
tgatctggcg gaccctaggt ggaggaatcg atctcacctt ctactcaggc cccgccccgg    3000
ccgatgttac caggcaatat cttaccagca ctgtgggatt accggccatg cagcaataca    3060
acactcttgg attccaccaa tgtcgttggg gctacaacaa ctggtcggat ctggcggacg    3120
ttgttgcgaa ctttgagaag tttgagatcc cgttggaata tatctggtgc gtattgtact    3180
ggtttatggt atctcaaaac agtctaacag gcacttagga ccgatattga ctacatgcac    3240
ggatatcgca actttgacaa cgatcaacat cgcttttcct acagtgaggg cgatgaattt    3300
ctcagcaagc tacatgagag tggacgctac tatgtaccca ttgttgatgc ggcgctctac    3360
attcctaatc ccgaaaatgc ctctgatgcg taagtgtcta gtgacaaatt atattactgc    3420
ctgtatgcta attagcgata cagatacgct acgtatgaca gaggagctgc ggacgacgtc    3480
ttcctcaaga atcccgatgg tagcctctat attggagccg tttggccagg atatacagtc    3540
ttccccgatt ggcatcatcc caaggcagtt gacttctggg ctaacgagct tgttatctgg    3600
```

```
tcgaagaaag tggcgttcga tggtgtgtgg tacgacatgt ctgaagtttc atccttctgt    3660
gtcgggagct gtggcacagg taacctgact ctgaacccgg cacacccatc gtttcttctc    3720
cccggtgagc ctggtgatat catatatgat tacccagagg ctttcaatat caccaacgct    3780
acagaggcgg cgtcagcttc ggcgggagct tccagtcagg ctgcagcaac cgcgaccacc    3840
acgtcgactt cggtatcata tctgcggaca acgcccacgc ctggtgtccg caatgttgag    3900
cacccaccct atgtgatcaa ccatgaccaa gaaggccatg atctcagtgt ccatgcggtg    3960
tcgccgaatg caacgcatgt tgatggtgtt gaggagtatg atgtgcacgg tctctacgga    4020
catcaaggat tgaacgctac ctaccaaggt ctgcttgagg tctggtctca taagcggcgg    4080
ccatttatta ttggccgctc aaccttcgct ggctctggca aatgggcagg ccactggggc    4140
ggcgacaact attccaaatg gtggtccatg tactactcca tctcgcaagc cctctccttc    4200
tcacttttcg gcattccgat gtttggtgcg gacacctgtg ggtttaacgg aaactccgat    4260
gaggagctct gcaaccgatg gatgcaactg tccgcattct tcccattcta ccgaaaccac    4320
aatgagctct ccacaatccc acaggagcct tatcggtggg cttctgttat tgaagcaacc    4380
aagtccgcca tgagaattcg gtacgccatc ctaccttact tttatacgtt gtttgacctg    4440
gcccacacca cgggctccac tgtaatgcgc gcactttcct gggaattccc taatgaccca    4500
acattggctg cggttgagac tcaattcatg gttgggccgg ccatcatggt ggtcccggta    4560
ttggagcctc tggtcaatac ggtcaagggc gtattcccag gagttggaca tggcgaagtg    4620
tggtacgatt ggtacaccca ggctgcagtt gatgcgaagc ccggggtcaa cacgaccatt    4680
tcggcaccat tgggccacat cccagtttat gtacgaggtg gaaacatctt gccgatgcaa    4740
gagccggcat tgaccactcg tgaagcccgg caaaccccgt gggctttgct agctgcacta    4800
ggaagcaatg gaaccgcgtc ggggcagctc tatctcgatg atggagagag catctacccc    4860
aatgccaccc tccatgtgga cttcacggca tcgcggtcaa gcctgcgctc gtcggctcaa    4920
ggaagatgga aagagaggaa cccgcttgct aatgtgacgg tgctcggagt gaacaaggag    4980
ccctctgcgg tgaccctgaa tggacaggcc gtatttcccg ggtctgtcac gtacaattct    5040
acgtcccagg ttctctttgt tggggggctg caaaacttga cgaagggcgg cgcatgggcg    5100
gaaaactggg tattggaatg gtagtgtcag ccacaagcca ggtgtgcgcg tacagcatgc    5160
aacatgggaa cgatgctctg caatgtagct ctttggttat aattcaaaat tcaacttcca    5220
cctttgtttc accggcggcc acggcattcc tgcatgacta acgttctgta aatggacccg    5280
ataacaccca gcacgttgca gcagagaagg tactctctca cacgcactgc tctttatagt    5340
tgccgagacg gccgccgagg agaaaaccgc cggcctgtgg ccactattcg ctggaaggaa    5400
ccctgccagt cgaacacacc cgcccgtgat cgccaggggc cgatggattt cccccgcat    5460 ccttgtcggt tcatgagtga agactttaaa tcccatctag ctgacggtcg ggtacatcaa    5520
taactggcag cctagtttcc aagacacgga gaagcatgta atcgctattt atagaatgct    5580
gggatcggac ccgtcgaatg gtcttccgat gggaagtgac aactcacatt gtcatgttgg    5640
ccttactcaa tccaacggga tctgacctgc tttggctaac ctagtataaa tcagcatgtc    5700
tctcctttga tacatcggat cgttcctcaa atatagttat atcttcgaaa aattgacaag    5760
aaggatgaca atcttctgt ttctggccat tttcgtggct acagctctgg cagccacgcc    5820
tgcagaatgg cgctcccagt cgatatattt cctgctcacc gatcgctttg cgcgaacgga    5880
taattctacc actgcttctt gtgacttgag cgctcggggtt agtcacagca tgttctagaa    5940
```

```
tctccaattg attcgctgac agatctagca atattgcggt ggatcctggc agggcatcat    6000
caatcaggtc ggtccgtcca tcgttgcagc actatctaca tcaacgtttg tttggcaaat    6060
taacatccat tagctggact atattcaagg aatgggcttt acagcgatct ggatcacacc    6120
cgtaactgca cagatccccc aagatactgg ttacggacag gcatatcacg gatactggca    6180
gcaggacgcg tgagatgcta cctctatcgc ccggatgaat gtatatcctt cttaccatgc    6240
agacagttat gccctgaact cccattatgg tacggcagac gatctcaaag ctctggcttc    6300
agctcttcac tcacggggca tgtatctcat ggtggacgtt gttgccaatc acatggtatg    6360
ttcttagcct cccacgggac cttagcttta tatctgacag cgatagggcc acaatggtac    6420
ggggagctct gtggactaca gtgtttatag gccatttaat tcgcaaaagt actttcacaa    6480
cctctgttgg atctctgatt acaataacca gacaaacgtt gaagactgct ggctaggcga    6540
taacaccgtt gccttgccgg atcttgatac taccagtacg gaggtgaaga atatgtggta    6600
tgactgggtc gagtctctcg tctctaacta ctccggtaat cctacccttta cttcgctatt    6660
ttctgcctct tatgagacaa agactaacaa atatcaagtc gacggcctcc gcgtagacac    6720
agtcaagaac gtacagaaga acttctggcc cggctacaac aatgcttcag gcgtgtactg    6780
tattggagaa gtcttcgatg gggacgcctc atacacctgt ccttatcagg aagacttgga    6840
cggagtcctt aattacccca tgtaagccct acatttaacc ccattgaatg cttgccaacg    6900
acttgcaata ggtactatcc actcctccgg gctttcgaat ccaccaacgg cagtatcagc    6960
gacctctata acatgatcaa caccgtgaaa tccacctgca gagattctac gcttctaggg    7020
accttcgtcg aaaaccacga taacccacgc tttgccaagt aagaatatcc tctccgagtt    7080
caccattaca aacacaagag ctcacctcag aagctacaca agcg                     7124
```

<210> SEQ ID NO 13
<211> LENGTH: 2958
<212> TYPE: DNA
<213> ORGANISM: Aspergillus niger
<220> FEATURE:
<221> NAME/KEY: misc_feature
<223> OTHER INFORMATION: AgdA cDNA

<400> SEQUENCE: 13

```
atggtgaagt tgacgcatct ccttgccaga gcatggcttg tccctctggc ttatggagcg     60
agccagtcac tctatccac cactgccct tcgcagccgc agtttaccat tcctgcttcc     120
gcagatgtcg gtgcgcagct gattgccaac atcgatgatc ctcaggctgc cgacgcgcag    180
tcggtttgtc cgggctacaa ggcttcaaaa gtgcagcaca attcacgtgg attcactgcc    240
agtcttcagc tcgcgggcag gccatgtaac gtatacggca cagatgttga gtccttgaca    300
ctgtctgtgg agtaccagga ttcggatcga ctgaatattc agattctccc cactcatgtt    360
gactccacaa acgcttcttg gtactttctt tcggaaaacc tggtccccag acccaaggct    420
tccctcaatg catctgtatc ccagagcgac ctttttgtgt catggtcaaa tgagccgtcg    480
ttcaatttca aggtgatccg aaaggctaca ggcgacgcgc ttttcagtac agaaggcact    540
gtgctcgtat atgagaatca gttcatcgaa tttgtgaccg cgctccctga gaatataaac    600
ttgtatggcc ttggggagca tatcacgcaa ttccgcctcc agagaaatgc taatctgacc    660
atatatcctt cggatgatgg aacacctatt gaccaaaacc tctacggcca acatcccttc    720
tatctggata caagatatta caagggagat aggcagaatg gtcttatat tcccgtcaaa    780
agcagcgagg ctgatgcctc gcaagattat atctcccctct ctcatggcgt gtttctgagg    840
```

```
aactctcatg gacttgagat actcctccgg tctcaaaaat tgatctggcg gaccctaggt     900
ggaggaatcg atctcacctt ctactcaggc cccgccccgg ccgatgttac caggcaatat     960
cttaccagca ctgtgggatt accggccatg cagcaataca acactcttgg attccaccaa   1020
tgtcgttggg gctacaacaa ctggtcggat ctggcggacg ttgttgcgaa ctttgagaag   1080
tttgagatcc cgttggaata tatctggacc gatattgact acatgcacgg atatcgcaac   1140
tttgacaacg atcaacatcg cttttcctac agtgagggcg atgaatttct cagcaagcta   1200
catgagagtg gacgctacta tgtacccatt gttgatgcgg cgctctacat tcctaatccc   1260
gaaaatgcct ctgatgcata cgctacgtat gacagaggag ctgcggacga cgtcttcctc   1320
aagaatcccg atggtagcct ctatattgga gccgtttggc caggatatac agtcttcccc   1380
gattggcatc atcccaaggc agttgacttc tgggctaacg agcttgttat ctggtcgaag   1440
aaagtggcgt tcgatggtgt gtggtacgac atgtctgaag tttcatcctt ctgtgtcggg   1500
agctgtggca caggtaacct gactctgaac ccggcacacc catcgtttct tctcccggt    1560
gagcctggtg atatcatata tgattaccca gaggctttca atatcaccaa cgctacagag   1620
gcggcgtcag cttcggcggg agcttccagt caggctgcag caaccgcgac caccacgtcg   1680
acttcggtat catatctgcg gacaacgccc acgcctggtg tccgcaatgt tgagcaccca   1740
ccctatgtga tcaaccatga ccaagaaggc catgatctca gtgtccatgc ggtgtcgccg   1800
aatgcaacgc atgttgatgg tgttgaggag tatgatgtgc acggtctcta cggacatcaa   1860
ggattgaacg ctacctacca aggtctgctt gaggtctggt ctcataagcg gcggccattt   1920
attattggcc gctcaacctt cgctggctct ggcaaatggg caggccactg gggcggcgac   1980
aactattcca aatggtggtc catgtactac tccatctcgc aagccctctc cttctcactt   2040
ttcggcattc cgatgtttgg tgcggacacc tgtgggttta acggaaactc cgatgaggag   2100
ctctgcaacc gatggatgca actgtccgca ttcttcccat tctaccgaaa ccacaatgag   2160
ctctccacaa tcccacagga gccttatcgg tgggcttctg ttattgaagc aaccaagtcc   2220
gccatgagaa ttcggtacgc catcctacct tactttata cgttgtttga cctggcccac   2280
accacgggct ccactgtaat gcgcgcactt tcctgggaat tccctaatga cccaacattg   2340
gctgcggttg agactcaatt catggttggg ccggccatca tggtggtccc ggtattggag   2400
cctctggtca atacggtcaa gggcgtattc ccaggagttg acatggcga agtgtggtac   2460
gattggtaca cccaggctgc agttgatgcg aagcccgggg tcaacacgac catttcggca   2520
ccattgggcc acatcccagt ttatgtacga ggtggaaaca tcttgccgat gcaagagccg   2580
gcattgacca ctcgtgaagc ccggcaaacc ccgtgggctt tgctagctgc actaggaagc   2640
aatggaaccg cgtcggggca gctctatctc gatgatggag agagcatcta ccccaatgcc   2700
accctccatg tggacttcac ggcatcgcgg tcaagcctgc gctcgtcggc tcaaggaaga   2760
tggaaagaga ggaacccgct tgctaatgtg acggtgctcg gagtgaacaa ggagccctct   2820
gcggtgaccc tgaatggaca ggccgtattt cccgggtctg tcacgtacaa ttctacgtcc   2880
caggttctct ttgttggggg gctgcaaaac ttgacgaagg cggcgcatg ggcggaaaac    2940
tgggtattgg aatggtag                                                2958
```

<210> SEQ ID NO 14
<211> LENGTH: 985
<212> TYPE: PRT
<213> ORGANISM: Aspergillus niger
<220> FEATURE:
<221> NAME/KEY: misc_feature
<223> OTHER INFORMATION: AgdA protein

<400> SEQUENCE: 14

| | | | | | | | | | | | | | | | |
|---|---|---|---|---|---|---|---|---|---|---|---|---|---|---|---|
| Met | Val | Lys | Leu | Thr | His | Leu | Leu | Ala | Arg | Ala | Trp | Leu | Val | Pro | Leu |
| 1 | | | | 5 | | | | | 10 | | | | | 15 | |
| Ala | Tyr | Gly | Ala | Ser | Gln | Ser | Leu | Leu | Ser | Thr | Thr | Ala | Pro | Ser | Gln |
| | | | 20 | | | | | 25 | | | | | 30 | | |
| Pro | Gln | Phe | Thr | Ile | Pro | Ala | Ser | Ala | Asp | Val | Gly | Ala | Gln | Leu | Ile |
| | | | 35 | | | | | 40 | | | | | 45 | | |
| Ala | Asn | Ile | Asp | Asp | Pro | Gln | Ala | Ala | Asp | Ala | Gln | Ser | Val | Cys | Pro |
| | 50 | | | | | 55 | | | | | 60 | | | | |
| Gly | Tyr | Lys | Ala | Ser | Lys | Val | Gln | His | Asn | Ser | Arg | Gly | Phe | Thr | Ala |
| 65 | | | | | 70 | | | | | 75 | | | | | 80 |
| Ser | Leu | Gln | Leu | Ala | Gly | Arg | Pro | Cys | Asn | Val | Tyr | Gly | Thr | Asp | Val |
| | | | | 85 | | | | | 90 | | | | | 95 | |
| Glu | Ser | Leu | Thr | Leu | Ser | Val | Glu | Tyr | Gln | Asp | Ser | Asp | Arg | Leu | Asn |
| | | | 100 | | | | | 105 | | | | | 110 | | |
| Ile | Gln | Ile | Leu | Pro | Thr | His | Val | Asp | Ser | Thr | Asn | Ala | Ser | Trp | Tyr |
| | | | 115 | | | | | 120 | | | | | 125 | | |
| Phe | Leu | Ser | Glu | Asn | Leu | Val | Pro | Arg | Pro | Lys | Ala | Ser | Leu | Asn | Ala |
| | 130 | | | | | 135 | | | | | 140 | | | | |
| Ser | Val | Ser | Gln | Ser | Asp | Leu | Phe | Val | Ser | Trp | Ser | Asn | Glu | Pro | Ser |
| 145 | | | | | 150 | | | | | 155 | | | | | 160 |
| Phe | Asn | Phe | Lys | Val | Ile | Arg | Lys | Ala | Thr | Gly | Asp | Ala | Leu | Phe | Ser |
| | | | | 165 | | | | | 170 | | | | | 175 | |
| Thr | Glu | Gly | Thr | Val | Leu | Val | Tyr | Glu | Asn | Gln | Phe | Ile | Glu | Phe | Val |
| | | | 180 | | | | | 185 | | | | | 190 | | |
| Thr | Ala | Leu | Pro | Glu | Glu | Tyr | Asn | Leu | Tyr | Gly | Leu | Gly | Glu | His | Ile |
| | | | 195 | | | | | 200 | | | | | 205 | | |
| Thr | Gln | Phe | Arg | Leu | Gln | Arg | Asn | Ala | Asn | Leu | Thr | Ile | Tyr | Pro | Ser |
| | 210 | | | | | 215 | | | | | 220 | | | | |
| Asp | Asp | Gly | Thr | Pro | Ile | Asp | Gln | Asn | Leu | Tyr | Gly | Gln | His | Pro | Phe |
| 225 | | | | | 230 | | | | | 235 | | | | | 240 |
| Tyr | Leu | Asp | Thr | Arg | Tyr | Tyr | Lys | Gly | Asp | Arg | Gln | Asn | Gly | Ser | Tyr |
| | | | | 245 | | | | | 250 | | | | | 255 | |
| Ile | Pro | Val | Lys | Ser | Ser | Glu | Ala | Asp | Ala | Ser | Gln | Asp | Tyr | Ile | Ser |
| | | | 260 | | | | | 265 | | | | | 270 | | |
| Leu | Ser | His | Gly | Val | Phe | Leu | Arg | Asn | Ser | His | Gly | Leu | Glu | Ile | Leu |
| | | | 275 | | | | | 280 | | | | | 285 | | |
| Leu | Arg | Ser | Gln | Lys | Leu | Ile | Trp | Arg | Thr | Leu | Gly | Gly | Gly | Ile | Asp |
| | 290 | | | | | 295 | | | | | 300 | | | | |
| Leu | Thr | Phe | Tyr | Ser | Gly | Pro | Ala | Pro | Ala | Asp | Val | Thr | Arg | Gln | Tyr |
| 305 | | | | | 310 | | | | | 315 | | | | | 320 |
| Leu | Thr | Ser | Thr | Val | Gly | Leu | Pro | Ala | Met | Gln | Gln | Tyr | Asn | Thr | Leu |
| | | | | 325 | | | | | 330 | | | | | 335 | |
| Gly | Phe | His | Gln | Cys | Arg | Trp | Gly | Tyr | Asn | Asn | Trp | Ser | Asp | Leu | Ala |
| | | | 340 | | | | | 345 | | | | | 350 | | |
| Asp | Val | Val | Ala | Asn | Phe | Glu | Lys | Phe | Glu | Ile | Pro | Leu | Glu | Tyr | Ile |
| | | | 355 | | | | | 360 | | | | | 365 | | |
| Trp | Thr | Asp | Ile | Asp | Tyr | Met | His | Gly | Tyr | Arg | Asn | Phe | Asp | Asn | Asp |
| | 370 | | | | | 375 | | | | | 380 | | | | |
| Gln | His | Arg | Phe | Ser | Tyr | Ser | Glu | Gly | Asp | Glu | Phe | Leu | Ser | Lys | Leu |
| 385 | | | | | 390 | | | | | 395 | | | | | 400 |

-continued

His Glu Ser Gly Arg Tyr Tyr Val Pro Ile Val Asp Ala Ala Leu Tyr
               405                 410                 415

Ile Pro Asn Pro Glu Asn Ala Ser Asp Ala Tyr Ala Thr Tyr Asp Arg
           420                 425                 430

Gly Ala Ala Asp Asp Val Phe Leu Lys Asn Pro Asp Gly Ser Leu Tyr
       435                 440                 445

Ile Gly Ala Val Trp Pro Gly Tyr Thr Val Phe Pro Asp Trp His His
   450                 455                 460

Pro Lys Ala Val Asp Phe Trp Ala Asn Glu Leu Val Ile Trp Ser Lys
465                 470                 475                 480

Lys Val Ala Phe Asp Gly Val Trp Tyr Asp Met Ser Glu Val Ser Ser
               485                 490                 495

Phe Cys Val Gly Ser Cys Gly Thr Gly Asn Leu Thr Leu Asn Pro Ala
           500                 505                 510

His Pro Ser Phe Leu Leu Pro Gly Glu Pro Gly Asp Ile Ile Tyr Asp
       515                 520                 525

Tyr Pro Glu Ala Phe Asn Ile Thr Asn Ala Thr Glu Ala Ala Ser Ala
   530                 535                 540

Ser Ala Gly Ala Ser Ser Gln Ala Ala Ala Thr Ala Thr Thr Thr Ser
545                 550                 555                 560

Thr Ser Val Ser Tyr Leu Arg Thr Thr Pro Thr Pro Gly Val Arg Asn
               565                 570                 575

Val Glu His Pro Pro Tyr Val Ile Asn His Asp Gln Glu Gly His Asp
           580                 585                 590

Leu Ser Val His Ala Val Ser Pro Asn Ala Thr His Val Asp Gly Val
       595                 600                 605

Glu Glu Tyr Asp Val His Gly Leu Tyr Gly His Gln Gly Leu Asn Ala
   610                 615                 620

Thr Tyr Gln Gly Leu Leu Glu Val Trp Ser His Lys Arg Arg Pro Phe
625                 630                 635                 640

Ile Ile Gly Arg Ser Thr Phe Ala Gly Ser Gly Lys Trp Ala Gly His
               645                 650                 655

Trp Gly Gly Asp Asn Tyr Ser Lys Trp Trp Ser Met Tyr Tyr Ser Ile
           660                 665                 670

Ser Gln Ala Leu Ser Phe Ser Leu Phe Gly Ile Pro Met Phe Gly Ala
       675                 680                 685

Asp Thr Cys Gly Phe Asn Gly Asn Ser Asp Glu Glu Leu Cys Asn Arg
   690                 695                 700

Trp Met Gln Leu Ser Ala Phe Phe Pro Phe Tyr Arg Asn His Asn Glu
705                 710                 715                 720

Leu Ser Thr Ile Pro Gln Glu Pro Tyr Arg Trp Ala Ser Val Ile Glu
               725                 730                 735

Ala Thr Lys Ser Ala Met Arg Ile Arg Tyr Ala Ile Leu Pro Tyr Phe
           740                 745                 750

Tyr Thr Leu Phe Asp Leu Ala His Thr Thr Gly Ser Thr Val Met Arg
       755                 760                 765

Ala Leu Ser Trp Glu Phe Pro Asn Asp Pro Thr Leu Ala Ala Val Glu
   770                 775                 780

Thr Gln Phe Met Val Gly Pro Ala Ile Met Val Pro Val Leu Glu
785                 790                 795                 800

Pro Leu Val Asn Thr Val Lys Gly Val Phe Pro Gly Val Gly His Gly
               805                 810                 815

Glu Val Trp Tyr Asp Trp Tyr Thr Gln Ala Ala Val Asp Ala Lys Pro

```
            820                 825                 830
Gly Val Asn Thr Thr Ile Ser Ala Pro Leu Gly His Ile Pro Val Tyr
                835                 840                 845

Val Arg Gly Gly Asn Ile Leu Pro Met Gln Glu Pro Ala Leu Thr Thr
850                 855                 860

Arg Glu Ala Arg Gln Thr Pro Trp Ala Leu Leu Ala Ala Leu Gly Ser
865                 870                 875                 880

Asn Gly Thr Ala Ser Gly Gln Leu Tyr Leu Asp Asp Gly Glu Ser Ile
                885                 890                 895

Tyr Pro Asn Ala Thr Leu His Val Asp Phe Thr Ala Ser Arg Ser Ser
                900                 905                 910

Leu Arg Ser Ser Ala Gln Gly Arg Trp Lys Glu Arg Asn Pro Leu Ala
                915                 920                 925

Asn Val Thr Val Leu Gly Val Asn Lys Glu Pro Ser Ala Val Thr Leu
                930                 935                 940

Asn Gly Gln Ala Val Phe Pro Gly Ser Val Thr Tyr Asn Ser Thr Ser
945                 950                 955                 960

Gln Val Leu Phe Val Gly Gly Leu Gln Asn Leu Thr Lys Gly Gly Ala
                965                 970                 975

Trp Ala Glu Asn Trp Val Leu Glu Trp
                980                 985

<210> SEQ ID NO 15
<211> LENGTH: 1816
<212> TYPE: DNA
<213> ORGANISM: Artificial sequence
<220> FEATURE:
<223> OTHER INFORMATION: codon optimised cDNA of Penicillium Chrysogenum
      glucose oxidase

<400> SEQUENCE: 15
atgaagtcca ctattatcac ctccattctc ttctctgtgg ctgccgtcca ggcctatagc      60
ccggccgagc agatcgacgt ccagtctcac ctgctttctg accccaccaa ggtcgaggga     120
gagacttacg actatgtcat tgctggtggt ggtttgactg gtctgaccgt ggctgccaag     180
ctgtctgaaa acccgaagat caaagtcctt gtgattgaga agggattcta cgaatccaac     240
gatggaccga tcatcgagga ccccaacgcc tatggggaga tctttggaac tagtgtggat     300
cagaattatc tcacagttcc cctcatcaac aaccgaactg ggaaattaa gtctggcctc      360 ggtcttggtg ctcgaccttt gatcaacggc gattcctgga cccgccccga caaggtccag     420
atcgactcat gggaaaaggt ctttggcatg agggctgga actgggacaa tgtcttccag      480
tacatgcaga aagctgagcg ctcgcgcccc ccgactgccg cccagattga gccggtcac      540 ttctacgacc tgcctgtca tggaacagac ggaaccgttc atgccggccc tcgcacaac      600 ggcaagcctt ggtccccact gatgcgagcc tcatgaaca ccgtctccgc tttcggtgtc      660
cccgtccaga aggacttcca ctgccggtcac ccccgtggtg tctcgatgat cccgaacaac     720
ctccatgaga accagatccg ggctgatgcc gctcgcgaat ggcttcttcc caactaccag     780
cgcgataacc tgcagatcct gactggccag aaggtcggaa aggttttgtt caaccagacc     840
gcatctggac ctaaggctgt tggtgtgaac ttcggtacca caaggctgt taacttcaat     900 gtctacgcca agcaagaagt tctgttggcc gccggatctg ccatttctcc tttgatcctt     960
gaatactccg gtattggtat caagtccgtc cttgacaagg ccggtgttaa gcagctcctc    1020
gaactccctg ttggtctcaa catgcaagac cagaccacta ccactgttcg gtcccgcgcc    1080
```

-continued

```
aacaacgcac ctggacaagg ccaggccgct tactttgcca acttcaccga ggttctcggc   1140
gaccacgccg cccagggtat taagttgctg gacaccaagc ttgaccagtg ggccgaggag   1200
accgttgccc gcggtggctt ccacaatgtg actgccctca agatccagta tgagaactac   1260
cgtaactggc tccttgatga ggacgttgca tttgccgagc tcttcttcga cactgagggc   1320
aagatcaact ttgatatctg gaatcttatc cccttcactc gcggttccgt ccacatcctc   1380
agcagtgacc cttacctctg gcaatacgca aatgacccca gttcttcat gaacgagctg   1440 gatcttctcg gccaggccgc tgctactaag ctgggtcgtg agctctctag cgctggtgag   1500
atgaagaagt actacgctgg cgagaccatc cccggcgaca acctgcccca ggatgccacc   1560
gtcgagcagt gggaggacta cgtgatgatg aacttccgtc ctaactggca cgctgttagc   1620
acctgctcta tgatgtcccg cgagcttggt ggtgtcgtcg acgctactgc caaggtctac   1680
ggtactcagg gcctccgtgt cattgacgga tctatccctc ccactcaggt gtcctctcac   1740
gttatgaccg ttttctacgg tatggccttg cggatcgccg aatccgtcct tgaagactat   1800
gccaagaaag cttaaa                                                   1816
```

<210> SEQ ID NO 16
<211> LENGTH: 604
<212> TYPE: PRT
<213> ORGANISM: Penicillium chrysogenum
<220> FEATURE:
<221> NAME/KEY: misc_feature
<223> OTHER INFORMATION: Glucose oxidase protein

<400> SEQUENCE: 16

```
Met Lys Ser Thr Ile Ile Thr Ser Ile Leu Phe Ser Val Ala Ala Val
1               5                   10                  15

Gln Ala Tyr Ser Pro Ala Glu Gln Ile Asp Val Gln Ser His Leu Leu
            20                  25                  30

Ser Asp Pro Thr Lys Val Glu Gly Glu Thr Tyr Asp Tyr Val Ile Ala
        35                  40                  45

Gly Gly Gly Leu Thr Gly Leu Thr Val Ala Ala Lys Leu Ser Glu Asn
    50                  55                  60

Pro Lys Ile Lys Val Leu Val Ile Glu Lys Gly Phe Tyr Glu Ser Asn
65                  70                  75                  80

Asp Gly Pro Ile Ile Glu Asp Pro Asn Ala Tyr Gly Glu Ile Phe Gly
                85                  90                  95

Thr Ser Val Asp Gln Asn Tyr Leu Thr Val Pro Leu Ile Asn Asn Arg
            100                 105                 110

Thr Gly Glu Ile Lys Ser Gly Leu Gly Leu Gly Gly Ser Thr Leu Ile
        115                 120                 125

Asn Gly Asp Ser Trp Thr Arg Pro Asp Lys Val Gln Ile Asp Ser Trp
    130                 135                 140

Glu Lys Val Phe Gly Met Glu Gly Trp Asn Trp Asp Asn Val Phe Gln
145                 150                 155                 160

Tyr Met Gln Lys Ala Glu Arg Ser Arg Pro Thr Ala Ala Gln Ile
                165                 170                 175

Glu Ala Gly His Phe Tyr Asp Pro Ala Cys His Gly Thr Asp Gly Thr
            180                 185                 190

Val His Ala Gly Pro Arg Asp Asn Gly Lys Pro Trp Ser Pro Leu Met
        195                 200                 205

Arg Ala Leu Met Asn Thr Val Ser Ala Phe Gly Val Pro Val Gln Lys
    210                 215                 220
```

Asp Phe His Cys Gly His Pro Arg Gly Val Ser Met Ile Pro Asn Asn
225                 230                 235                 240

Leu His Glu Asn Gln Ile Arg Ala Asp Ala Arg Glu Trp Leu Leu
            245                 250                 255

Pro Asn Tyr Gln Arg Asp Asn Leu Gln Ile Leu Thr Gly Gln Lys Val
            260                 265                 270

Gly Lys Val Leu Phe Asn Gln Thr Ala Ser Gly Pro Lys Ala Val Gly
        275                 280                 285

Val Asn Phe Gly Thr Asn Lys Ala Val Asn Phe Asn Val Tyr Ala Lys
290                 295                 300

Gln Glu Val Leu Leu Ala Ala Gly Ser Ala Ile Ser Pro Leu Ile Leu
305                 310                 315                 320

Glu Tyr Ser Gly Ile Gly Ile Lys Ser Val Leu Asp Lys Ala Gly Val
                325                 330                 335

Lys Gln Leu Leu Glu Leu Pro Val Gly Leu Asn Met Gln Asp Gln Thr
                340                 345                 350

Thr Thr Thr Val Arg Ser Arg Ala Asn Asn Ala Pro Gly Gln Gly Gln
            355                 360                 365

Ala Ala Tyr Phe Ala Asn Phe Thr Glu Val Leu Gly Asp His Ala Ala
370                 375                 380

Gln Gly Ile Lys Leu Leu Asp Thr Lys Leu Asp Gln Trp Ala Glu Glu
385                 390                 395                 400

Thr Val Ala Arg Gly Phe His Asn Val Thr Ala Leu Lys Ile Gln
                405                 410                 415

Tyr Glu Asn Tyr Arg Asn Trp Leu Leu Asp Glu Asp Val Ala Phe Ala
            420                 425                 430

Glu Leu Phe Phe Asp Thr Glu Gly Lys Ile Asn Phe Asp Ile Trp Asn
            435                 440                 445

Leu Ile Pro Phe Thr Arg Gly Ser Val His Ile Leu Ser Ser Asp Pro
        450                 455                 460

Tyr Leu Trp Gln Tyr Ala Asn Asp Pro Lys Phe Phe Met Asn Glu Leu
465                 470                 475                 480

Asp Leu Leu Gly Gln Ala Ala Thr Lys Leu Gly Arg Glu Leu Ser
                485                 490                 495

Ser Ala Gly Glu Met Lys Lys Tyr Tyr Ala Gly Glu Thr Ile Pro Gly
            500                 505                 510

Asp Asn Leu Pro Gln Asp Ala Thr Val Glu Gln Trp Glu Asp Tyr Val
            515                 520                 525

Met Met Asn Phe Arg Pro Asn Trp His Ala Val Ser Thr Cys Ser Met
530                 535                 540

Met Ser Arg Glu Leu Gly Gly Val Val Asp Ala Thr Ala Lys Val Tyr
545                 550                 555                 560

Gly Thr Gln Gly Leu Arg Val Ile Asp Gly Ser Ile Pro Pro Thr Gln
                565                 570                 575

Val Ser Ser His Val Met Thr Val Phe Tyr Gly Met Ala Leu Arg Ile
            580                 585                 590

Ala Glu Ser Val Leu Glu Asp Tyr Ala Lys Lys Ala
            595                 600

<210> SEQ ID NO 17
<211> LENGTH: 12018
<212> TYPE: DNA
<213> ORGANISM: Aspergillus niger
<220> FEATURE:
<221> NAME/KEY: misc_feature
<223> OTHER INFORMATION: AgsE genomic DNA including 2kb upstream and downstream flanking regions

<400> SEQUENCE: 17

```
tttcatttct tgcctttct tttcttttt accaattttt ccctctttgc agttggaggc      60
ccgaaatcaa cgccacggaa gttggcggat tgatgatgat tgggataata ctgttggccc     120
caaaaataca cacacagaca cacacatacc atattcagga acaaacacac caccaaaccc    180
gctgcatgca tgggatggct cacctccccc ttctgcgagt tacgggcagc agataatgta    240
tacgtctgat cctttacacc agacgaacta agtatacaa aaaaaaaaac gactaccgga    300
ctaccaccac ccctattacg gtatcacaac catcaacttc tctcaagtcg tatactacta    360
gtagactagt caaatcccgg tccctccgcc accaatcggg agggtccgtc cttatcagac    420
ccaaaatttc ctcccaaaaa aattgagaga aaacgagcaa cttgatgaca gtaagacatc    480
acctgcacta ttgtgtagag tgtcttagaa gagggccaat aaagttttt cgttaccgag    540
attggctgca cgccaccgta ttgctgcctc ttcaggtatc gtttcgcttg ggcgtgaata    600
cgatctggct gattgattgt attggccccg aaaatacctt tagaagcagc agcagcagca    660
gcagaagggg tctgttgctt tacctctttc ccatggcacg gatataggcg atgggaacaa    720
taaggaagtc ctcggagggg ccacgaaggg tccagtcttc ggggggggct taaaagggag    780
ggactatatc ttaatgggga ttggtgaggg cctggcggta tcaagtgggc ggaaagaacc    840
cttctttcaa gacatccagt gatccagtcc aactgcccct tgggctccac cttaaactgc    900
tttccggtcc gagaggaaac ctaactaacg gctcccgaat agcctactta ctatacgaga    960
attggctcat attttccat aggatggctg tcggaccacc caatggtccg cttccgttat    1020
tcatattttt tttttattca ctcttgtcca ttctgaattt tcaattttc atttcatact    1080
tatttttaaa ttccccttt ggactttgca ccgcactgcc gcggtctagt cctcttctga    1140
gcaggcaaaa agtattccgt catagccaaa gggaaccgcc cctcccactc gctctggaca    1200
aggctagagt ccctccggcg tggcttcgat atctttctta cccggggaac aattcctata    1260
cgagtgagct ggcaccggga agccattcag agtggttctc cagtcagctt ggggggttatt    1320
attagcaaaa tacacataga cgagacaaga cgagacgtct agtctgcttc tgtttctttt    1380
ttttcatttc atcgtttctc ccctccctcg atccactatc gcggatatcg atgttgtgcc    1440
cccccagtc cagcctctca ttgctgagcc tcagcatcgc tgctagctaa ttaccttact    1500
agttggagtg tgattagctt ttttctccat ttggatttct tgcctttgtt ccccatcatc    1560
tcccctctga cactttctct tcctcctatt cctcgtatca tctttcctct ctctctctct    1620
ctctttctct cttccacttt ctcctctctc gcttgatccc tcttatctct gatctcatgc    1680
atcgtttctt gttttagttg ttgttgcatt gtgattcccc atagatttca ctcgttaacg    1740
aagcgtgcct gtgtttctct cgttatctgc accctatcta tcgctcgtta tcagtcccat    1800
ctatccactc aaccgactat cattgagtga cctgcacccc cagcgaagag agatcgcaat    1860
caatctggtg acgagtcaga acccattctt tcccctccag tctttggcga actccataac    1920
cgcatcgatc tggctcaacg ttgtgttcct ggtttgttga ccggtggtca tcccgggtcg    1980
ccgcgacctt cccacccagc atgaagtggg ctatttccgg cacgctgctc gcctgtttcg    2040
caacaactgc aacggcctgg ccttacgacg agtccctcgt cgactacaac ttcaatcaga    2100
accagtccgc tacgaacccg gcggactatt ggggaacatg gcccaatcat accgggggact    2160
acttccccct cccggacaat tggcgcttcc ccgtctacac cctctttctc gaccgcttcg    2220
```

-continued

```
tcaacggtga ccccacaaac gacaacatca atggcaccct gttcgaacat gacctccgct      2280
cgaatcagat gcgccatggt ggcgatgttg ccggcctgct ggatacccttg gattacttgc      2340 agggcatggg aatcaaggtc ggtccctgtg gcttgtccga tgctgcgatc aattactgac      2400
gatggtttag ggtctctatc ttgccggaac aatcctcatg aaccagccct ggggatctga      2460
cggttattcg gctttggaca cgacattgtt ggatcaacac tatggtaacc tgcagacgtg      2520
gcgcaatgcc atcacggaaa ttcacaagcg cgggatgtat gtcatcttcg ataacaccat      2580
cgcaacgtaa gtttgccgct gccttttccc ctctttccta cccaacaaac taacctgcaa      2640
tttttaggat gggtgatttg atcggatttg atggctatct gaacaccacc accccttct      2700 ccgtgaagga acaccaaacg gtgtggaaga ctgaccgccg ctatgtggac ttcgacattg      2760
gcaatgacta caacgagacg tgcgactacc cccgcttctg gttcgaggat ggctaccccg      2820
ttcaagcgtc agtcaccgag gagcttgtcg gatgttacaa cagtgatttc gaccagtacg      2880
gtgatattga ggcctttggt gtcttccccg attggcaacg tcagctggca aaattcgcct      2940
ccgttcagga tcgactccgt gaatgggttc cctccgtgcg cgagcgtttg atccgccact      3000
cctgcatcat tattcagtcg ctcgatattg acggtttccg gtacgacaag gcgactcagg      3060
caaccgtcga cgccctcgga gatatgtcca atgcgtaccg cgagtgcgcc cgcgccgtag      3120
gaaaagagaa cttcttcatt gcgggcgaaa tcacgggtgg taataccttt ggttccatct      3180
acttgggccg aggaagacag cccaaccagt tccctgactc ggcggaggca gccatgaagc      3240
tgaccaacac ttccgacgcc cagtatttcc tgcgtgaagt gggacatgag gcgattgatg      3300
gtgcagcctt ccactactcc atttaccgag cgctgacccg cttcctgggc atggatggta      3360
acttggctgc cggttacgat gtgccagtcg actgggttga tgcctggaat ctcatgctgc      3420
agtccaacga tctggtcaat gcgaatacag gcaagttcga ccccgccac atgtacgggg      3480 ctaccaacca ggatgtcttc cgttggccca cggtggaaaa gggcgtggag cgtcagttgc      3540
ttggattgta catcacgact cttctgctcc ccggaattcc gctccttctc tggggcgagg      3600
aacaggcgtt ttacgtactg gatgccacgg catcgaacta catctacggt cggcaggcca      3660
tgtctcctgc caccgcatgg agggatcatg gctgtttctc cttggaatcg tctcagtact      3720
ataattggcc cattgagtcc ggccgtcagg gctgccacga ccccacggtg gcctacgatc      3780
atcgtgaccc gtctcatccc gtgcgcaata tcattaagca tatgtatcag atgcgcgaac      3840
agttccccgt cctcaatgac ggctatacta ttcaaaagct ctcgaaccac accgaggacg      3900
tgtactatct cggttccaac ggcacagcca ccgagaccgg actctggtcg attcttcgtg      3960
atgtgaacgc ggatgtgcag gatttgggct ccgatgcgaa gaaccagcct gtctggctgg      4020
tttaccacaa cacgaaccgc accattgatt acaagtttga ctgctcggat aatgatacag      4080
ctctgattgc ccccttcgat agtggcacct gggtcaaaaa cctgttccac ccgtatgacg      4140
agcaccagct gatcgattcc cccaccaagt tgggattgaa cggatcaact gcatacagtg      4200
gctgcttggc taatatgacc atgtccgcct atgaattccg ggcctacgtg cctaaaaccc      4260
gctttactaa acccaggccg atgattacaa agttcactcc gggacacgat gtcccgatcc      4320
gctcgaccgt ggccccgaac gcagacgaga acgtggaggt cgaaatttac ttctccgaag      4380
aaatggattg cgactcggtg acaaagtcca ttacccttc gtcatcgacc gaaattggaa      4440 aggcccctc tgtcgattct ggcagtgtca actgcaagtc agtccccgcc actaacacca      4500
gctgaccgcc ccagattccc ggggtgtgga tgtgggcggc caacctgaca ggtgtgtaca      4560
acggcattca tcgtctcaca gtcaacaatg tcagcacaga gagtgggaac gcaaccacca      4620
```

```
acgccgtcga ccatttcctc ttccgcatcg gccagattga taatccgatg attttcagca      4680
gtgcgaacta ttcaactagt ttgctccata aggaatccaa cggcacccct ttcatccagc      4740
accacgccgc gggtgctgat aagtatcgct attctacgaa ttggggtacc actttctccg      4800
attggattga ctacaggggc ggaaatgaca ctattgagga actcgaatgg tcgggaacca      4860
agaagcagtc atggaaagga accacgttc gcgtggagta ttggagtcgt tggaccggca       4920
gcagcgatta cgtccaagag ggagacgcgg gctggaacga gaatgttcca cgccgtttcc      4980
ctcacgtctt cttcaacgga ccctacaacc agtatgggta tgatgcaggt ctggacaacg      5040
tggtccgcca ggacagcgtt gacggtctct ggaaatatca tttcaccgcg gaatggcctg      5100
ctcaagctca attgaacatt tggggtatga accctgatgg ggagcctgac cagagttggg      5160
tcctgggaga tgccgataat gattcggttc tcgatcgcat gccgccctct tcgctgtccg      5220
cgacattgat taacatcact gaacaccccc cctctcccta catttcgtgg aatatcttca      5280
ttgatgacgg gaccatgcgc ttccagctgt tccccgtcgg gcatcagaat actcagatcg      5340
ccatgtatgt gctcttttgg atcatccccg tcatcacggg cgcagccggt gtgtgggctt      5400
tcatgaagtc tttctacaag gtcaaattca accaggttgg tgtgagcgaa aaacaccaga      5460
tgatcccatt ggccttgcgg cggaagttca agcgcaatcg caatcgtggc ggtgatgagg      5520
aaaactcaaa ccctctcatg cgtctggcga acaagtccgg gttcctccag actgacacgg      5580
cgattggtgg tgctgctagc ggcaagcgtc gcatggtcct gatcgccacc atggagtacg      5640
acattgagga ttgggccatc aagatcaaga ttggtggtct tggtgtcatg gcgcaactca      5700
tgggtaagac tctgggtcat caagacttga tctgggtggt gccttgcgtt gggggtgtcg      5760 attacccccgt ggacaaaccc gcagagccca tgcatgtcac cattcttggc aattcgtacg      5820
aggtccaggt ccagtatcac gtcttgaata acatcaccta tgttctgctg gatgcccctg      5880
tgttccgtca acagtctaag tcagagcctt acccggctcg catggacgac ctgaacagcg      5940
ccatttacta ctcggcctgg aatcagtgca ttgcggaagc ctgcaagaga ttccctatcg      6000
acctgtatca tatcaacgac taccatggtt ccctggctcc actgtatcta cttcctgaca      6060
cagtacctgc ctgtctttcc ctgcataacg ccgagttcca aggtttgtgg cccatgcgga      6120
cgcagaaaga aaaggaggaa gtttgctccg tgttcaatct ggatatcgag accgtgaggc      6180
attacgtgca gtttggagag gtgttcaact tgctccactc gggtgctagt tatctccgtg      6240
ttcaccaaca aggtttcggt gctgttggtg tgtctaagaa gtacggaaag cggtcctacg      6300
cgcgttaccc catttctctgg ggtctccgca aggttggaaa cctacctaac cctgatccgt      6360
ctgatgtcgg tgagtggagc aaggaacagg ccagcgccat gggtgacaat gtgagcgtgg      6420
acccgactta tgaagccggt cgaggcgacc tcaagcgtca agctcaggag tgggccggtc      6480
ttgaacagaa ccctgacgcc gatttgcttg tcttcgttgg tcgttggtcg atgcagaagg      6540
gtgttgattt gatcgccgac gtcatgcctg ctgtcctgga agcacgcccc aatgttcagc      6600
tcatttgtgt tggaccagtt atcgatctct acggtaaatt cgcggccctc aaactcgatc      6660
acatgatgaa ggtctacccc ggacgagtgt tctctagacc tgagttcacg gcattgcccc      6720
cctacatctt ctctggtgct gaattcgcgc tgattccctc tcgtgacgag cccttcggtc      6780
tggtcgccgt cgagttcgga cgtaagggag ctctgggtat cggtgcccgg gttggtggtc      6840
tcggtcagat gccaggttgg tggtacaatg tggaatcgac agctacctcc catttgctcg      6900
ttcagttcaa gctggctatc gacgcggctc tcagttcgaa aacggaaact cgtgctatga      6960
```

```
tgcgtgcccg gtccgccaaa cagcgcttcc cggtcgccca gtgggtggaa gacttggaga    7020
tcctgcaaac caccgccatc caagtgcaca acaaggaatt ggttaaacat aacggtcgac    7080
ccttcacccc gtctggaact accacgccgg gtggcatctt aagccagccg tcaagtccac    7140
taatgccccc tggaatgcag actcccttgg ctcattctcg ggaaagcagc tattctaacc    7200
tgaaccgtct cagtgaatat gtcacagatc cgaaaacaaa ctacagtcga acatcagcc    7260
ccagtgggac ggaaaagccg cggtccggcc tgcaacgaca gctttctctt ggtgttcgct    7320
caggacctgg tcatcaagag cgccgtggcc gtcgtggacg ccagcgcgac agcatccccg    7380
aacacgaaga caccgcaggg gccatgaccg acgtcgaaga agaccacgag acattgggg     7440
atcagcagga tgcggacgac gagtacactc tcaccccggc tcaggtcgag aaggacgtc    7500
gcttgcaggc tgtccagcag cagggagtgg gtatgccgac gagtccgggc gtccgccgtt    7560
atagtcaaga ctccttgcat ccgcgacagc ttcctagcag ccctggcccc gtcccacctc    7620
ctacacagag cctccttccg ccacccaggc ttggggatgc cggtagccga ctcagtagcg    7680
cgtctgtcct gtccctggat tcggtcgttg gtaccaagac ggacttcaag ctccagaagg    7740
ttgacccctt ctttacggat tctactggcg agtactacaa ggcattcgac aagaggctgg    7800
tcggcttgaa cggtcgaac tccgaatccc agctttgcat tgaggaatat ctcatcaaga    7860
gtgagaagga atggttcgac aagttccgcg atgcccgact gggtcgtcta aaatcccccg    7920
cgtcgtctgt cttccgggac aagcatggtg cctcccctgt tggctcctac tacgatgata    7980
cgggctcccg ggtgagtggt gactatgacc gggagtcccg cgacacggaa gatgacgagt    8040
tcctcctggg caaggactac gtgcctccga cgggtctgcg caagtggatg cagattcgtg    8100
ttggagactg gccagtctac tcgttattcc ttgccttggg tcagatcatt gcagccaact    8160
cttatcaggt gaccttgctt accggtgagg ttggtgagac ggccgagaag ctctatggta    8220
tcgcaaccac ctacctgatc acctcgatcc tttggtggct tgtgttccgt tacttcaaat    8280
cggtggtgtg cctctcggct ccctggttct tctatggcct tgccttcctt ctgatcggct    8340
ccgctcactt tgaacccaat tcattcaacc ggggttggat ccagaacatc ggaagtggat    8400
gttacgccgc tgcctcgtct agcggttcca tcttcttcgc cttgaacttt ggtgacgaag    8460
gtggtgcgcc ggtcgaaacc tggatcttcc gggcttgtct cattcagggt atccagtcgg    8520
cttatatcat cggactgtgg tattgggggtt ccactctgac caaggcatcc agccagggtc    8580
tgttgacctc gacgaacaac atcgccaata gctggaagat gacgtgagta cattgaaccc    8640
tctgattgtt catcaatcag ccagtcattc catcttgtga cccgctaaca ctgatctcct    8700
ctagtgccat ctgttacccg attgcaatct tcctctgggc tgttggattg ctgcttctct    8760
ttggacttcc taactactat cgccaaaccc cgggcaaagt ggcctccttt tacaagtccg    8820
tattccgccg caagatcgtc ctctggaact tcgttgccgt catcctgcaa aacttcttcc    8880
tcagcgcacc gtacgccgc aactgggggct gtaagtctaa cttttccctgc cacatcgtgt    8940
cgaattgata agctaactct agtccgcagt ccttggtct tccaatcacg ccaaggcctg    9000
gcaaatcgtt attctctgta tcgtcttcta cgggttcgtc tgggcgggct tcctgttcgt    9060
cgtcagccgc tatttcaagt cccacagctg gttcctgccc gtgtttgcgt gcggacttgg    9120
agcacctcgc ttcattcaaa tctggtgggg tgtctcgggc atcggttact tccttccctg    9180
ggtctccgga ggctatctcg gcggagcttt ggcctcgagg agtctctggc tctggctggg    9240
cgtgttggat tccatccagg gtctcggggtt cggtatcatc ctcctgcaga ccctcacccg    9300
catgcacatg ctgttcaccc tgatctgctc gcaggtgctt ggttccattg ccaccatctg    9360
```

```
tgcgcgggcg tttgccccga ataacgtcgg gcccggccct gtgtcgccgg accctacctt   9420
tggaggaagt gcagtggcca atgcgtggtt ctgggtggcc ctgttttgtc agctgttggt   9480
gtgtgctggc ttcctcctct tcttccggaa agagcagctt ccaaaccttg aacgcctta   9540 atgatgtggt ggtgcgcttg ggcaccaccg ggcatgaaca tttaacatac gtcccaccat   9600
tccttccttc cttccctccc tacctacgcc ccttggatat aattttactg tctgtcataa   9660
tataatctct cctgtatgta tatagaagtt cgcattacga tctgaatgat gtccaggtcg   9720
ttctcagcca atacaatttt gggattggaa aaatccctg cagattcatc tgctgtcaat   9780
atcttccacc gcgtgatagt gttcaaaagg tttcaatgta gatggtatat tgtctaaaga   9840
gtacttgaga gataggctgt agtcgatcac ctgggttggg tgcagattag tgaggacggc   9900
tatgcctgcg ataacccagt acgtactcga ttgctgcctc aggtcccaat acttacccag   9960
ggaacaccaa aatacaataa atactttgta acagaattat aataataacc ttcaataagt  10020
atgaaataat aataatcgaa aagggaataa gagattagtc aaaagaaaa ggaaaaaaaa  10080 aaaaaaaagg aaaccaaaat ccgaaaggca atcccgaagc aactcccgct tcggccggaa  10140
ctatccctga tcgggacaac cggggctcc accgcgtgcc ttccgggcga ggcagacgaa  10200
ctaataatat tgagaatgcg ggagggagtg ggaagttaga gagcgagaga cactctggaa  10260
caggagttcc cccctccctc tcttctctct tctctctctt cttctcttca tcttcttact  10320
tccgtctact ttcttcctca ctgctactat tgattccttg actccacacc taacactgct  10380
gtccccatca cacacataca tacatacact gcttttcttc attaactcta ttgatcatct  10440
acgatgaggc atcttgctac ttgatgagct catcgctctt accatgatgg aagaaatgga  10500
agttgaaaga tgaaaatgca tcgacattgg ctgacactcg cggttcgctg aatacaataa  10560
caagaacgaa acaacagatg gactgaaccc gacccgaacc ccaatctgaa acgaaactcc  10620
ttcccttctt cctcctaaac atccgtcttg aacgatgtga gccgcgcctt gattgcctcc  10680
tccgactcgt cggtatccaa ctcccgaaga acaccgcttc caacatcata aatcaacccg  10740
tgaacctgca acccacgctc ctggatcgct tccaacacca cgctcttctc cttcaacagc  10800
ttgacaccct ccaagacatt cagctcgacc agcttgaggt tcgcctggtc agccggcagc  10860
gagttcagca gatccaggtt cttcgcccgg agctggcgca ggggaagcaa ccaggggtcc  10920
aggattccca actgcttgtt acccagggca gcagcaacac cgccgcagct ggtgtgaccg  10980
cagaggacta catggttgac gcgcaggtaa cggaccgcgt actcgatcac ggcagacgag  11040
ctgaggtcgc ccgcgtgcag gacgttggca atgttgcggt ggacgaagac atcgcccggc  11100
ttaagaccaa ggagagtggt ttcggggcat cgggaatcgg agcagccgat ccagagaatc  11160
tcgggctgct ggccgttcgc gagcgtgggg aacagtgagg ggtcttcctt ggagatctgg  11220
gctgcccagt cttgttctg gtgcagagcg gaggtgaaac ggtctgagtc tgtattagca  11280
cacgctggtg gcttggtggt ggaaaagcag gcggcttgtc gtggtggaaa aaaggagaca  11340
cgctgggagg gaagaggaag gctggctcga gaacttggct gcgcccccga ccggggagag  11400
gtatatattc cgaccctgga atacatccgc tgcagtcgcg aaacaagcct tgtggactcc  11460
atgatggtgt gaagagggta tgaagacaac agaattgacg gaaaatgcag caccacgagg  11520
atgagtcact gccaggggaa ccccgaaaag gaacggaaac cacaaatgaa agcgcaagga  11580
tatcaatacg ttttgcaaat tcgcatacga tgaagcaagc acagtgatac agaaacgggg  11640
gcaaaacgac acgctgaggg ttcggtggca gggaagttga gggaaaagat gaggaaaagg  11700
```

| | |
|---|---|
| taaaatctgt gggccgccgc cgctttgcaa gtctatccag aaacgccaag aatggatggt | 11760 |
| tctgttctgc tggtgctgat gctcacgtac ctgtagcagt gggcgccatg atagctgatg | 11820 |
| ttcaagtgag atatcgcagt gtgcttgtcg acagtctgt tggattcaag atactgagta | 11880 |
| ttttgtgttg gctacgaggc tcccctttct ttctttgccc ccgccggca attccttggg | 11940 |
| gattctcgtc ggcaatgttc accccaacc atgcaaacag tgcaaacacc ccaactcacc | 12000 |
| ggacacccaa aggcgcca | 12018 |

```
<210> SEQ ID NO 18
<211> LENGTH: 7281
<212> TYPE: DNA
<213> ORGANISM: Aspergillus niger
<220> FEATURE:
<221> NAME/KEY: misc_feature
<223> OTHER INFORMATION: AgsE cDNA

<400> SEQUENCE: 18
```

| | |
|---|---|
| atgaagtggg ctatttccgg cacgctgctc gcctgtttcg caacaactgc aacggcctgg | 60 |
| ccttacgacg agtccctcgt cgactacaac ttcaatcaga accagtccgc tacgaacccg | 120 |
| gcggactatt ggggaacatg gcccaatcat accggggact acttcccctc cccgacaat | 180 |
| tggcgcttcc ccgtctacac cctctttctc gaccgcttcg tcaacggtga ccccacaaac | 240 |
| gacaacatca atggcaccct gttcgaacat gacctccgct cgaatcagat gcgccatggt | 300 |
| ggcgatgttg ccggcctgct ggataccttg gattacttgc agggcatggg aatcaagggt | 360 |
| ctctatcttg ccggaacaat cctcatgaac cagccctggg gatctgacgg ttattcggct | 420 |
| ttggacacga cattgttgga tcaacactat ggtaacctgc agacgtggcg caatgccatc | 480 |
| acggaaattc acaagcgcgg gatgtatgtc atcttcgata caccatcgc aacgatgggt | 540 |
| gatttgatcg gatttgatgg ctatctgaac accaccaccc ccttctccgt gaaggaacac | 600 |
| caaacggtgt ggaagactga ccgccgctat gtggacttcg acattggcaa tgactacaac | 660 |
| gagacgtgcg actaccccg cttctggttc gaggatggct accccgttca agcgtcagtc | 720 |
| accgaggagc ttgtcggatg ttacaacagt gatttcgacc agtacggtga tattgaggcc | 780 |
| tttggtgtct tccccgattg gcaacgtcag ctggcaaaat tcgcctccgt tcaggatcga | 840 |
| ctccgtgaat gggttccctc cgtgcgcgag cgtttgatcc gccactcctg catcattatt | 900 |
| cagtcgctcg atattgacgg tttccggtac gacaaggcga ctcaggcaac cgtcgacgcc | 960 |
| ctcggagata tgtccaatgc gtaccgcgag tgcgcccgcg ccgtaggaaa agagaacttc | 1020 |
| ttcattgcgg gcgaaatcac gggtggtaat acctttggtt ccatctactt gggccgagga | 1080 |
| agacagccca accagttccc tgactcggcg gaggcagcca tgaagctgac caacacttcc | 1140 |
| gacgcccagt atttcctgcg tgaagtggga catgaggcga ttgatggtgc agccttccac | 1200 |
| tactccattt accgagcgct gacccgcttc ctgggcatgg atggtaactt ggctgccggt | 1260 |
| tacgatgtgc cagtcgactg ggttgatgcc tggaatctca tgctgcagtc caacgatctg | 1320 |
| gtcaatgcga atacaggcaa gttcgacccc cgccacatgt acgggctac caaccaggat | 1380 |
| gtcttccgtt ggcccacggt ggaaaagggc gtggagcgtc agttgcttgg attgtacatc | 1440 |
| acgactcttc tgctccccgg aattccgctc cttctctggg gcgaggaaca ggcgttttac | 1500 |
| gtactggatg ccacggcatc gaactacatc tacggtcggc aggccatgtc tcctgccacc | 1560 |
| gcatggaggg atcatggctg tttctccttg gaatcgtctc agtactataa ttggcccatt | 1620 |
| gagtccggcc gtcagggctg ccacgacccc acggtggcct acgatcatcg tgaccgtctct | 1680 |

```
catcccgtgc gcaatatcat taagcatatg tatcagatgc gcgaacagtt ccccgtcctc    1740
aatgacggct atactattca aaagctctcg aaccacaccg aggacgtgta ctatctcggt    1800
tccaacggca cagccaccga gaccggactc tggtcgattc ttcgtgatgt gaacgcggat    1860
gtgcaggatt tgggctccga tgcgaagaac cagcctgtct ggctggttta ccacaacacg    1920
aaccgcacca ttgattacaa gtttgactgc tcggataatg atacagctct gattgccccc    1980
ttcgatagtg gcacctgggt caaaaacctg ttccacccgt atgacgagca ccagctgatc    2040
gattccccca ccaagttggg attgaacgga tcaactgcat acagtggctg cttggctaat    2100
atgaccatgt ccgcctatga attccgggcc tacgtgccta aacccgctt tactaaaccc    2160
aggccgatga ttacaaagtt cactccggga cacgatgtcc cgatccgctc gaccgtggcc    2220
ccgaacgcag acgagaacgt ggaggtcgaa atttacttct ccgaagaaat ggattgcgac    2280
tcggtgacaa agtccattac cctttcgtca tcgaccgaaa ttggaaaggc ccctctgtc    2340
gattctggca gtgtcaactg caagtcagtc cccgccacta acaccagctg gaccggccag    2400
attcccgggg tgtggatgtg ggcggccaac ctgacaggtg tgtacaacgg cattcatcgt    2460
ctcacagtca acaatgtcag cacagagagt gggaacgcaa ccaccaacgc cgtcgaccat    2520
ttcctcttcc gcatcggcca gattgataat ccgatgattt tcagcagtgc gaactattca    2580
actagtttgc tccataagga atccaacggc accctttca tccagcacca cgccgcgggt    2640
gctgataagt atcgctattc tacgaattgg ggtaccactt tctccgattg gattgactac    2700
aggggcggaa atgacactat tgaggaactc gaatggtcgg gaaccaagaa gcagtcatgg    2760
aaaggaaacc acgttcgcgt ggagtattgg agtcgttgga ccggcagcag cgattacgtc    2820
caagagggag acgcgggctg gaacgagaat gttccacgcc gtttccctca cgtcttcttc    2880
aacgacccct acaaccagta tgggtatgat gcaggtctgg acaacgtggt ccgccaggac    2940
agcgttgacg gtctctggaa atatcatttc accgcggaat ggcctgctca agctcaattg    3000
aacatttggg gtatgaaccc tgatggggag cctgaccaga gttgggtcct gggagatgcc    3060
gataatgatt cggttctcga tcgcatgccg ccctcttcgc tgtccgcgac attgattaac    3120
atcactgaac cccccccctc tccctacatt tcgtggaata tcttcattga tgacgggacc    3180
atgcgcttcc agctgttccc cgtcgggcat cagaatactc agatcgccat gtatgtgctc    3240
ttttggatca tccccgtcat cacgggcgca gccggtgtgt gggctttcat gaagtctttc    3300
tacaaggtca aattcaacca ggttggtgtg agcgaaaaac accagatgat cccattggcc    3360
ttgcggcgga agttcaagcg caatcgcaat cgtggcggtg atgaggaaaa ctcaaaccct    3420
ctcatgcgtc tggcgaacaa gtccgggttc ctccagactg acacggcgat tggtggtgct    3480
gctagcggca agcgtcgcat ggtcctgatc gccaccatgg agtacgacat tgaggattgg    3540
gccatcaaga tcaagattgg tggtcttggt gtcatggcgc aactcatggg taagactctg    3600
ggtcatcaag acttgatctg ggtggtgcct tgcgttgggg gtgtcgatta ccccgtggac    3660
aaacccgcag agcccatgca tgtcaccatt cttggcaatt cgtacgaggt ccaggtccag    3720
tatcacgtct tgaataacat caccctatgtt ctgctggatg ccctgtgtt ccgtcaacag    3780
tctaagtcag agccttaccc ggctcgcatg gacgacctga acagcgccat ttactactcg    3840
gcctggaatc agtgcattgc ggaagcctgc aagagattcc ctatcgacct gtatcatatc    3900
aacgactacc atggttccct ggctccactg tatctactc ctgacacagt acctgcctgt    3960
cttttccctgc ataacgccga gttccaaggt ttgtggccca tgcggacgca gaaagaaaag    4020
gaggaagttt gctccgtgtt caatctggat atcgagaccg tgaggcatta cgtgcagttt    4080
```

```
ggagaggtgt tcaacttgct ccactcgggt gctagttatc tccgtgttca ccaacaaggt   4140
ttcggtgctg ttggtgtgtc taagaagtac ggaaagcggt cctacgcgcg ttaccccatt   4200
ttctggggtc tccgcaaggt tggaaaccta cctaaccctg atccgtctga tgtcggtgag   4260
tggagcaagg aacaggccag cgccatgggt gacaatgtga gcgtggaccc gacttatgaa   4320
gccggtcgag gcgacctcaa gcgtcaagct caggagtggg ccggtcttga acagaaccct   4380
gacgccgatt tgcttgtctt cgttggtcgt tggtcgatgc agaagggtgt tgatttgatc   4440
gccgacgtca tgcctgctgt cctggaagca cgcccaatg ttcagctcat ttgtgttgga   4500
ccagttatcg atctctacgg taaattcgcg gccctcaaac tcgatcacat gatgaaggtc   4560
taccccggac gagtgttctc tagacctgag ttcacggcat gcccccccta catcttctct   4620
ggtgctgaat tcgcgctgat tccctctcgt gacgagccct tcggtctggt cgccgtcgag   4680
ttcggacgta agggagctct gggtatcggt gcccggttg gtggtctcgg tcagatgcca   4740
ggttggtggt acaatgtgga atcgacagct acctcccatt tgctcgttca gttcaagctg   4800
gctatcgacg cggctctcag ttcgaaaacg gaaactcgtg ctatgatgcg tgcccggtcc   4860
gccaaacagc gcttcccggt cgcccagtgg gtggaagact ggagatcct gcaaaccacc   4920 gccatccaag tgcacaacaa ggaattggtt aaacataacg gtcgacccdt caccccgtct   4980
ggaactacca cgccgggtgg catcttaagc cagccgtcaa gtccactaat gcccctgga   5040 atgcagactc ccttggctca ttctcgggaa agcagctatt ctaacctgaa ccgtctcagt   5100
gaatatgtca cagatccgaa aacaaactac agtcgagaca tcagccccag tgggacggaa   5160
aagccgcggt ccggcctgca acgacagctt tctcttggtg ttcgctcagg acctggtcat   5220
caagagcgcc gtggccgtcg tggacgccag cgcgacagca tccccgaaca cgaagcacc   5280 gcagggcca tgaccgacgt cgaagaagac cacgaggaca ttggggatca gcaggatgcg   5340
gacgacgagt acactctcac cccggctcag gtcgaggaag acgtcgctt gcaggctgtc   5400 cagcagcagg gagtgggtat gccgacgagt ccggcgtcc gccgttatag tcaagactcc   5460
ttgcatccgc gacagcttcc tagcagccct ggcccgtcc cacctcctac acagagcctc   5520
cttccgccac ccaggcttgg ggatgccggt agccgactca gtagcgcgtc tgtcctgtcc   5580
ctggattcgg tcgttggtac caagacggac ttcaagctcc agaaggttga cccccttcttt   5640 acggattcta ctggcgagta ctacaaggca ttcgacaaga ggctggtcgg cttgaacggc   5700
tcgaactccg aatcccagct ttgcattgag gaatatctca tcaagagtga aaggaatgg   5760 ttcgacaagt tccgcgatgc ccgactgggt cgtctaaaat cccccgcgtc gtctgtcttc   5820
cgggacaagc atggtgcctc ccctgttggc tcctactacg atgatacggg ctcccgggtg   5880
agtggtgact atgaccggga gtcccgcgac acgaagatg acgagttcct cctgggcaag   5940
gactacgtgc ctccgacggg tctgcgcaag tggatgcaga ttcgtgttgg agactggcca   6000
gtctactcgt tattccttgc cttgggtcag atcattgcag ccaactctta tcaggtgacc   6060
ttgcttaccg gtgaggttgg tgagacggcc gagaagctct atggtatcgc aaccacctac   6120
ctgatcacct cgatccttg gtggcttgtg ttccgttact tcaaatcggt ggtgtgcctc   6180
tcggctccct ggttcttcta tggccttgcc ttccttctga tcggctccgc tcactttgaa   6240
cccaattcat tcaaccgggg ttggatccag aacatcggaa gtggatgtta cgccgctgcc   6300
tcgtctagcg gttccatctt cttcgccttg aactttggtg acgaaggtgg tgcgccggtc   6360
gaaacctgga tcttccgggc ttgtctcatt cagggtatcc agtcggctta tatcatcgga   6420
```

```
ctgtggtatt ggggttccac tctgaccaag gcatccagcc agggtctgtt gacctcgacg    6480
aacaacatcg ccaatagctg gaagatgact gccatctgtt acccgattgc aatcttcctc    6540
tgggctgttg gattgctgct tctctttgga cttcctaact actatcgcca aaccccgggc    6600
aaagtggcct cctttacaa gtccgtattc cgccgcaaga tcgtcctctg gaacttcgtt    6660
gccgtcatcc tgcaaaactt cttcctcagc gcaccgtacg gccgcaactg gggcttcctt    6720
tggtcttcca atcacgccaa ggcctggcaa atcgttattc tctgtatcgt cttctacggg    6780
ttcgtctggg cgggcttcct gttcgtcgtc agccgctatt tcaagtccca cagctggttc    6840
ctgcccgtgt ttgcgtgcgg acttggagca cctcgcttca ttcaaatctg gtggggtgtc    6900
tcgggcatcg gttacttcct tccctgggtc tccggaggct atctcggcgg agctttggcc    6960
tcgaggagtc tctggctctg gctgggcgtg ttggattcca tccagggtct cgggttcggt    7020
atcatcctcc tgcagaccct caccccgcatg cacatgctgt tcaccctgat ctgctcgcag    7080
gtgcttggtt ccattgccac catctgtgcg cgggcgtttg ccccgaataa cgtcgggccc    7140
ggccctgtgt cgccggaccc tacctttgga ggaagtgcag tggccaatgc gtggttctgg    7200
gtggccctgt tttgtcagct gttgattagt gaggacggct atgcctgcga taacccaaat    7260
tataataata accttcaata a                                              7281
```

<210> SEQ ID NO 19
<211> LENGTH: 2426
<212> TYPE: PRT
<213> ORGANISM: Aspergillus niger
<220> FEATURE:
<221> NAME/KEY: misc_feature
<223> OTHER INFORMATION: AgsE protein

<400> SEQUENCE: 19

```
Met Lys Trp Ala Ile Ser Gly Thr Leu Leu Ala Cys Phe Ala Thr Thr
 1               5                  10                  15

Ala Thr Ala Trp Pro Tyr Asp Glu Ser Leu Val Asp Tyr Asn Phe Asn
            20                  25                  30

Gln Asn Gln Ser Ala Thr Asn Pro Ala Asp Tyr Trp Gly Thr Trp Pro
        35                  40                  45

Asn His Thr Gly Asp Tyr Phe Pro Ser Pro Asp Asn Trp Arg Phe Pro
    50                  55                  60

Val Tyr Thr Leu Phe Leu Asp Arg Phe Val Asn Gly Asp Pro Thr Asn
65                  70                  75                  80

Asp Asn Ile Asn Gly Thr Leu Phe Glu His Asp Leu Arg Ser Asn Gln
                85                  90                  95

Met Arg His Gly Gly Asp Val Ala Gly Leu Leu Asp Thr Leu Asp Tyr
            100                 105                 110

Leu Gln Gly Met Gly Ile Lys Gly Leu Tyr Leu Ala Gly Thr Ile Leu
        115                 120                 125

Met Asn Gln Pro Trp Gly Ser Asp Gly Tyr Ser Ala Leu Asp Thr Thr
    130                 135                 140

Leu Leu Asp Gln His Tyr Gly Asn Leu Gln Thr Trp Arg Asn Ala Ile
145                 150                 155                 160

Thr Glu Ile His Lys Arg Gly Met Tyr Val Ile Phe Asn Thr Ile
                165                 170                 175

Ala Thr Met Gly Asp Leu Ile Gly Phe Asp Gly Tyr Leu Asn Thr Thr
            180                 185                 190

Thr Pro Phe Ser Val Lys Glu His Gln Thr Val Trp Lys Thr Asp Arg
        195                 200                 205
```

```
Arg Tyr Val Asp Phe Asp Ile Gly Asn Asp Tyr Asn Glu Thr Cys Asp
    210                 215                 220
Tyr Pro Arg Phe Trp Phe Glu Asp Gly Tyr Pro Val Gln Ala Ser Val
225                 230                 235                 240
Thr Glu Glu Leu Val Gly Cys Tyr Asn Ser Asp Phe Asp Gln Tyr Gly
                245                 250                 255
Asp Ile Glu Ala Phe Gly Val Phe Pro Asp Trp Gln Arg Gln Leu Ala
            260                 265                 270
Lys Phe Ala Ser Val Gln Asp Arg Leu Arg Glu Trp Val Pro Ser Val
        275                 280                 285
Arg Glu Arg Leu Ile Arg His Ser Cys Ile Ile Gln Ser Leu Asp
    290                 295                 300
Ile Asp Gly Phe Arg Tyr Asp Lys Ala Thr Gln Ala Thr Val Asp Ala
305                 310                 315                 320
Leu Gly Asp Met Ser Asn Ala Tyr Arg Glu Cys Ala Arg Ala Val Gly
                325                 330                 335
Lys Glu Asn Phe Phe Ile Ala Gly Glu Ile Thr Gly Gly Asn Thr Phe
            340                 345                 350
Gly Ser Ile Tyr Leu Gly Arg Gly Arg Gln Pro Asn Gln Phe Pro Asp
        355                 360                 365
Ser Ala Glu Ala Ala Met Lys Leu Thr Asn Thr Ser Asp Ala Gln Tyr
    370                 375                 380
Phe Leu Arg Glu Val Gly His Glu Ala Ile Asp Gly Ala Ala Phe His
385                 390                 395                 400
Tyr Ser Ile Tyr Arg Ala Leu Thr Arg Phe Leu Gly Met Asp Gly Asn
                405                 410                 415
Leu Ala Ala Gly Tyr Asp Val Pro Val Asp Trp Val Asp Ala Trp Asn
            420                 425                 430
Leu Met Leu Gln Ser Asn Asp Leu Val Asn Ala Asn Thr Gly Lys Phe
        435                 440                 445
Asp Pro Arg His Met Tyr Gly Ala Thr Asn Gln Asp Val Phe Arg Trp
    450                 455                 460
Pro Thr Val Glu Lys Gly Val Glu Arg Gln Leu Leu Gly Leu Tyr Ile
465                 470                 475                 480
Thr Thr Leu Leu Leu Pro Gly Ile Pro Leu Leu Leu Trp Gly Glu Glu
                485                 490                 495
Gln Ala Phe Tyr Val Leu Asp Ala Thr Ala Ser Asn Tyr Ile Tyr Gly
            500                 505                 510
Arg Gln Ala Met Ser Pro Ala Thr Ala Trp Arg Asp His Gly Cys Phe
        515                 520                 525
Ser Leu Glu Ser Ser Gln Tyr Tyr Asn Trp Pro Ile Glu Ser Gly Arg
    530                 535                 540
Gln Gly Cys His Asp Pro Thr Val Ala Tyr Asp His Arg Asp Pro Ser
545                 550                 555                 560
His Pro Val Arg Asn Ile Ile Lys His Met Tyr Gln Met Arg Glu Gln
                565                 570                 575
Phe Pro Val Leu Asn Asp Gly Tyr Thr Ile Gln Lys Leu Ser Asn His
            580                 585                 590
Thr Glu Asp Val Tyr Tyr Leu Gly Ser Asn Gly Thr Ala Thr Glu Thr
        595                 600                 605
Gly Leu Trp Ser Ile Leu Arg Asp Val Asn Ala Asp Val Gln Asp Leu
    610                 615                 620
```

-continued

Gly Ser Asp Ala Lys Asn Gln Pro Val Trp Leu Val Tyr His Asn Thr
625                 630                 635                 640

Asn Arg Thr Ile Asp Tyr Lys Phe Asp Cys Ser Asp Asn Asp Thr Ala
            645                 650                 655

Leu Ile Ala Pro Phe Asp Ser Gly Thr Trp Val Lys Asn Leu Phe His
        660                 665                 670

Pro Tyr Asp Glu His Gln Leu Ile Asp Ser Pro Thr Lys Leu Gly Leu
    675                 680                 685

Asn Gly Ser Thr Ala Tyr Ser Gly Cys Leu Ala Asn Met Thr Met Ser
690                 695                 700

Ala Tyr Glu Phe Arg Ala Tyr Val Pro Lys Thr Arg Phe Thr Lys Pro
705                 710                 715                 720

Arg Pro Met Ile Thr Lys Phe Thr Pro Gly His Asp Val Pro Ile Arg
            725                 730                 735

Ser Thr Val Ala Pro Asn Ala Asp Glu Asn Val Glu Val Glu Ile Tyr
        740                 745                 750

Phe Ser Glu Glu Met Asp Cys Asp Ser Val Thr Lys Ser Ile Thr Leu
    755                 760                 765

Ser Ser Ser Thr Glu Ile Gly Lys Ala Pro Ser Val Asp Ser Gly Ser
770                 775                 780

Val Asn Cys Lys Ser Val Pro Ala Thr Asn Thr Ser Trp Thr Gly Gln
785                 790                 795                 800

Ile Pro Gly Val Trp Met Trp Ala Ala Asn Leu Thr Gly Val Tyr Asn
            805                 810                 815

Gly Ile His Arg Leu Thr Val Asn Asn Val Ser Thr Glu Ser Gly Asn
        820                 825                 830

Ala Thr Thr Asn Ala Val Asp His Phe Leu Phe Arg Ile Gly Gln Ile
    835                 840                 845

Asp Asn Pro Met Ile Phe Ser Ser Ala Asn Tyr Ser Thr Ser Leu Leu
850                 855                 860

His Lys Glu Ser Asn Gly Thr Leu Phe Ile Gln His His Ala Ala Gly
865                 870                 875                 880

Ala Asp Lys Tyr Arg Tyr Ser Thr Asn Trp Gly Thr Thr Phe Ser Asp
            885                 890                 895

Trp Ile Asp Tyr Arg Gly Gly Asn Asp Thr Ile Glu Glu Leu Glu Trp
        900                 905                 910

Ser Gly Thr Lys Lys Gln Ser Trp Lys Gly Asn His Val Arg Val Glu
    915                 920                 925

Tyr Trp Ser Arg Trp Thr Gly Ser Ser Asp Tyr Val Gln Glu Gly Asp
930                 935                 940

Ala Gly Trp Asn Glu Asn Val Pro Arg Arg Phe Pro His Val Phe Phe
945                 950                 955                 960

Asn Gly Pro Tyr Asn Gln Tyr Gly Tyr Asp Ala Gly Leu Asp Asn Val
            965                 970                 975

Val Arg Gln Asp Ser Val Asp Gly Leu Trp Lys Tyr His Phe Thr Ala
        980                 985                 990

Glu Trp Pro Ala Gln Ala Gln Leu Asn Ile Trp Gly Met Asn Pro Asp
    995                 1000                1005

Gly Glu Pro Asp Gln Ser Trp Val Leu Gly Asp Ala Asp Asn Asp
    1010                1015                1020

Ser Val Leu Asp Arg Met Pro Pro Ser Ser Leu Ser Ala Thr Leu
    1025                1030                1035

Ile Asn Ile Thr Glu His Pro Pro Ser Pro Tyr Ile Ser Trp Asn

-continued

```
            1040                1045                1050

Ile Phe Ile Asp Asp Gly Thr Met Arg Phe Gln Leu Phe Pro Val
        1055                1060                1065

Gly His Gln Asn Thr Gln Ile Ala Met Tyr Val Leu Phe Trp Ile
        1070                1075                1080

Ile Pro Val Ile Thr Gly Ala Ala Gly Val Trp Ala Phe Met Lys
        1085                1090                1095

Ser Phe Tyr Lys Val Lys Phe Asn Gln Val Gly Val Ser Glu Lys
        1100                1105                1110

His Gln Met Ile Pro Leu Ala Leu Arg Arg Lys Phe Lys Arg Asn
        1115                1120                1125

Arg Asn Arg Gly Gly Asp Glu Glu Asn Ser Asn Pro Leu Met Arg
        1130                1135                1140

Leu Ala Asn Lys Ser Gly Phe Leu Gln Thr Asp Thr Ala Ile Gly
        1145                1150                1155

Gly Ala Ala Ser Gly Lys Arg Arg Met Val Leu Ile Ala Thr Met
        1160                1165                1170

Glu Tyr Asp Ile Glu Asp Trp Ala Ile Lys Ile Lys Ile Gly Gly
        1175                1180                1185

Leu Gly Val Met Ala Gln Leu Met Gly Lys Thr Leu Gly His Gln
        1190                1195                1200

Asp Leu Ile Trp Val Val Pro Cys Val Gly Gly Val Asp Tyr Pro
        1205                1210                1215

Val Asp Lys Pro Ala Glu Pro Met His Val Thr Ile Leu Gly Asn
        1220                1225                1230

Ser Tyr Glu Val Gln Val Gln Tyr His Val Leu Asn Asn Ile Thr
        1235                1240                1245

Tyr Val Leu Leu Asp Ala Pro Val Phe Arg Gln Gln Ser Lys Ser
        1250                1255                1260

Glu Pro Tyr Pro Ala Arg Met Asp Asp Leu Asn Ser Ala Ile Tyr
        1265                1270                1275

Tyr Ser Ala Trp Asn Gln Cys Ile Ala Glu Ala Cys Lys Arg Phe
        1280                1285                1290

Pro Ile Asp Leu Tyr His Ile Asn Asp Tyr His Gly Ser Leu Ala
        1295                1300                1305

Pro Leu Tyr Leu Leu Pro Asp Thr Val Pro Ala Cys Leu Ser Leu
        1310                1315                1320

His Asn Ala Glu Phe Gln Gly Leu Trp Pro Met Arg Thr Gln Lys
        1325                1330                1335

Glu Lys Glu Glu Val Cys Ser Val Phe Asn Leu Asp Ile Glu Thr
        1340                1345                1350

Val Arg His Tyr Val Gln Phe Gly Glu Val Phe Asn Leu Leu His
        1355                1360                1365

Ser Gly Ala Ser Tyr Leu Arg Val His Gln Gln Gly Phe Gly Ala
        1370                1375                1380

Val Gly Val Ser Lys Lys Tyr Gly Lys Arg Ser Tyr Ala Arg Tyr
        1385                1390                1395

Pro Ile Phe Trp Gly Leu Arg Lys Val Gly Asn Leu Pro Asn Pro
        1400                1405                1410

Asp Pro Ser Asp Val Gly Glu Trp Ser Lys Glu Gln Ala Ser Ala
        1415                1420                1425

Met Gly Asp Asn Val Ser Val Asp Pro Thr Tyr Glu Ala Gly Arg
        1430                1435                1440
```

Gly Asp Leu Lys Arg Gln Ala Gln Glu Trp Ala Gly Leu Glu Gln
    1445                1450                1455

Asn Pro Asp Ala Asp Leu Leu Val Phe Val Gly Arg Trp Ser Met
    1460                1465                1470

Gln Lys Gly Val Asp Leu Ile Ala Asp Val Met Pro Ala Val Leu
    1475                1480                1485

Glu Ala Arg Pro Asn Val Gln Leu Ile Cys Val Gly Pro Val Ile
    1490                1495                1500

Asp Leu Tyr Gly Lys Phe Ala Ala Leu Lys Leu Asp His Met Met
    1505                1510                1515

Lys Val Tyr Pro Gly Arg Val Phe Ser Arg Pro Glu Phe Thr Ala
    1520                1525                1530

Leu Pro Pro Tyr Ile Phe Ser Gly Ala Glu Phe Ala Leu Ile Pro
    1535                1540                1545

Ser Arg Asp Glu Pro Phe Gly Leu Val Ala Val Glu Phe Gly Arg
    1550                1555                1560

Lys Gly Ala Leu Gly Ile Gly Ala Arg Val Gly Gly Leu Gly Gln
    1565                1570                1575

Met Pro Gly Trp Trp Tyr Asn Val Glu Ser Thr Ala Thr Ser His
    1580                1585                1590

Leu Leu Val Gln Phe Lys Leu Ala Ile Asp Ala Ala Leu Ser Ser
    1595                1600                1605

Lys Thr Glu Thr Arg Ala Met Met Arg Ala Arg Ser Ala Lys Gln
    1610                1615                1620

Arg Phe Pro Val Ala Gln Trp Val Glu Asp Leu Glu Ile Leu Gln
    1625                1630                1635

Thr Thr Ala Ile Gln Val His Asn Lys Glu Leu Val Lys His Asn
    1640                1645                1650

Gly Arg Pro Phe Thr Pro Ser Gly Thr Thr Thr Pro Gly Gly Ile
    1655                1660                1665

Leu Ser Gln Pro Ser Ser Pro Leu Met Pro Pro Gly Met Gln Thr
    1670                1675                1680

Pro Leu Ala His Ser Arg Glu Ser Ser Tyr Ser Asn Leu Asn Arg
    1685                1690                1695

Leu Ser Glu Tyr Val Thr Asp Pro Lys Thr Asn Tyr Ser Arg Asp
    1700                1705                1710

Ile Ser Pro Ser Gly Thr Glu Lys Pro Arg Ser Gly Leu Gln Arg
    1715                1720                1725

Gln Leu Ser Leu Gly Val Arg Ser Gly Pro Gly His Gln Glu Arg
    1730                1735                1740

Arg Gly Arg Arg Gly Arg Gln Arg Asp Ser Ile Pro Glu His Glu
    1745                1750                1755

Asp Thr Ala Gly Ala Met Thr Asp Val Glu Glu Asp His Glu Asp
    1760                1765                1770

Ile Gly Asp Gln Gln Asp Ala Asp Asp Glu Tyr Thr Leu Thr Pro
    1775                1780                1785

Ala Gln Val Glu Glu Gly Arg Arg Leu Gln Ala Val Gln Gln Gln
    1790                1795                1800

Gly Val Gly Met Pro Thr Ser Pro Gly Val Arg Arg Tyr Ser Gln
    1805                1810                1815

Asp Ser Leu His Pro Arg Gln Leu Pro Ser Ser Pro Gly Pro Val
    1820                1825                1830

-continued

```
Pro Pro Pro Thr Gln Ser Leu Leu Pro Pro Arg Leu Gly Asp
    1835              1840              1845

Ala Gly Ser Arg Leu Ser Ser Ala Ser Val Leu Ser Leu Asp Ser
    1850              1855              1860

Val Val Gly Thr Lys Thr Asp Phe Lys Leu Gln Lys Val Asp Pro
    1865              1870              1875

Phe Phe Thr Asp Ser Thr Gly Glu Tyr Tyr Lys Ala Phe Asp Lys
    1880              1885              1890

Arg Leu Val Gly Leu Asn Gly Ser Asn Ser Glu Ser Gln Leu Cys
    1895              1900              1905

Ile Glu Glu Tyr Leu Ile Lys Ser Glu Lys Glu Trp Phe Asp Lys
    1910              1915              1920

Phe Arg Asp Ala Arg Leu Gly Arg Leu Lys Ser Pro Ala Ser Ser
    1925              1930              1935

Val Phe Arg Asp Lys His Gly Ala Ser Pro Val Gly Ser Tyr Tyr
    1940              1945              1950

Asp Asp Thr Gly Ser Arg Val Ser Gly Asp Tyr Asp Arg Glu Ser
    1955              1960              1965

Arg Asp Thr Glu Asp Asp Glu Phe Leu Leu Gly Lys Asp Tyr Val
    1970              1975              1980

Pro Pro Thr Gly Leu Arg Lys Trp Met Gln Ile Arg Val Gly Asp
    1985              1990              1995

Trp Pro Val Tyr Ser Leu Phe Leu Ala Leu Gly Gln Ile Ile Ala
    2000              2005              2010

Ala Asn Ser Tyr Gln Val Thr Leu Leu Thr Gly Glu Val Gly Glu
    2015              2020              2025

Thr Ala Glu Lys Leu Tyr Gly Ile Ala Thr Thr Tyr Leu Ile Thr
    2030              2035              2040

Ser Ile Leu Trp Trp Leu Val Phe Arg Tyr Phe Lys Ser Val Val
    2045              2050              2055

Cys Leu Ser Ala Pro Trp Phe Phe Tyr Gly Leu Ala Phe Leu Leu
    2060              2065              2070

Ile Gly Ser Ala His Phe Glu Pro Asn Ser Phe Asn Arg Gly Trp
    2075              2080              2085

Ile Gln Asn Ile Gly Ser Gly Cys Tyr Ala Ala Ala Ser Ser Ser
    2090              2095              2100

Gly Ser Ile Phe Phe Ala Leu Asn Phe Gly Asp Glu Gly Gly Ala
    2105              2110              2115

Pro Val Glu Thr Trp Ile Phe Arg Ala Cys Leu Ile Gln Gly Ile
    2120              2125              2130

Gln Ser Ala Tyr Ile Ile Gly Leu Trp Tyr Trp Gly Ser Thr Leu
    2135              2140              2145

Thr Lys Ala Ser Ser Gln Gly Leu Leu Thr Ser Thr Asn Asn Ile
    2150              2155              2160

Ala Asn Ser Trp Lys Met Thr Ala Ile Cys Tyr Pro Ile Ala Ile
    2165              2170              2175

Phe Leu Trp Ala Val Gly Leu Leu Leu Phe Gly Leu Pro Asn
    2180              2185              2190

Tyr Tyr Arg Gln Thr Pro Gly Lys Val Ala Ser Phe Tyr Lys Ser
    2195              2200              2205

Val Phe Arg Arg Lys Ile Val Leu Trp Asn Phe Val Ala Val Ile
    2210              2215              2220

Leu Gln Asn Phe Phe Leu Ser Ala Pro Tyr Gly Arg Asn Trp Gly
```

```
                2225                2230                2235
Phe Leu Trp Ser Ser Asn His Ala Lys Ala Trp Gln Ile Val Ile
    2240                2245                2250

Leu Cys Ile Val Phe Tyr Gly Phe Val Trp Ala Gly Phe Leu Phe
    2255                2260                2265

Val Val Ser Arg Tyr Phe Lys Ser His Ser Trp Phe Leu Pro Val
    2270                2275                2280

Phe Ala Cys Gly Leu Gly Ala Pro Arg Phe Ile Gln Ile Trp Trp
    2285                2290                2295

Gly Val Ser Gly Ile Gly Tyr Phe Leu Pro Trp Val Ser Gly Gly
    2300                2305                2310

Tyr Leu Gly Gly Ala Leu Ala Ser Arg Ser Leu Trp Leu Trp Leu
    2315                2320                2325

Gly Val Leu Asp Ser Ile Gln Gly Leu Gly Phe Gly Ile Ile Leu
    2330                2335                2340

Leu Gln Thr Leu Thr Arg Met His Met Leu Phe Thr Leu Ile Cys
    2345                2350                2355

Ser Gln Val Leu Gly Ser Ile Ala Thr Ile Cys Ala Arg Ala Phe
    2360                2365                2370

Ala Pro Asn Asn Val Gly Pro Gly Pro Val Ser Pro Asp Pro Thr
    2375                2380                2385

Phe Gly Gly Ser Ala Val Ala Asn Ala Trp Phe Trp Val Ala Leu
    2390                2395                2400

Phe Cys Gln Leu Leu Ile Ser Glu Asp Gly Tyr Ala Cys Asp Asn
    2405                2410                2415

Pro Asn Tyr Asn Asn Asn Leu Gln
    2420                2425

<210> SEQ ID NO 20
<211> LENGTH: 2407
<212> TYPE: PRT
<213> ORGANISM: Aspergillus niger
<220> FEATURE:
<221> NAME/KEY: misc_feature
<223> OTHER INFORMATION: AgsE mature protein

<400> SEQUENCE: 20

Trp Pro Tyr Asp Glu Ser Leu Val Asp Tyr Asn Phe Asn Gln Asn Gln
1               5                   10                  15

Ser Ala Thr Asn Pro Ala Asp Tyr Trp Gly Thr Trp Pro Asn His Thr
            20                  25                  30

Gly Asp Tyr Phe Pro Ser Pro Asp Asn Trp Arg Phe Pro Val Tyr Thr
        35                  40                  45

Leu Phe Leu Asp Arg Phe Val Asn Gly Asp Pro Thr Asn Asp Asn Ile
    50                  55                  60

Asn Gly Thr Leu Phe Glu His Asp Leu Arg Ser Asn Gln Met Arg His
65                  70                  75                  80

Gly Gly Asp Val Ala Gly Leu Leu Asp Thr Leu Asp Tyr Leu Gln Gly
                85                  90                  95

Met Gly Ile Lys Gly Leu Tyr Leu Ala Gly Thr Ile Leu Met Asn Gln
            100                 105                 110

Pro Trp Gly Ser Asp Gly Tyr Ser Ala Leu Asp Thr Thr Leu Leu Asp
        115                 120                 125

Gln His Tyr Gly Asn Leu Gln Thr Trp Arg Asn Ala Ile Thr Glu Ile
    130                 135                 140
```

```
His Lys Arg Gly Met Tyr Val Ile Phe Asp Asn Thr Ile Ala Thr Met
145                 150                 155                 160

Gly Asp Leu Ile Gly Phe Asp Gly Tyr Leu Asn Thr Thr Thr Pro Phe
                165                 170                 175

Ser Val Lys Glu His Gln Thr Val Trp Lys Thr Asp Arg Arg Tyr Val
            180                 185                 190

Asp Phe Asp Ile Gly Asn Asp Tyr Asn Glu Thr Cys Asp Tyr Pro Arg
                195                 200                 205

Phe Trp Phe Glu Asp Gly Tyr Pro Val Gln Ala Ser Val Thr Glu Glu
        210                 215                 220

Leu Val Gly Cys Tyr Asn Ser Asp Phe Asp Gln Tyr Gly Asp Ile Glu
225                 230                 235                 240

Ala Phe Gly Val Phe Pro Asp Trp Gln Arg Gln Leu Ala Lys Phe Ala
                245                 250                 255

Ser Val Gln Asp Arg Leu Arg Glu Trp Val Pro Ser Val Arg Glu Arg
            260                 265                 270

Leu Ile Arg His Ser Cys Ile Ile Gln Ser Leu Asp Ile Asp Gly
            275                 280                 285

Phe Arg Tyr Asp Lys Ala Thr Gln Ala Thr Val Asp Ala Leu Gly Asp
    290                 295                 300

Met Ser Asn Ala Tyr Arg Glu Cys Ala Arg Ala Val Gly Lys Glu Asn
305                 310                 315                 320

Phe Phe Ile Ala Gly Glu Ile Thr Gly Gly Asn Thr Phe Gly Ser Ile
                325                 330                 335

Tyr Leu Gly Arg Gly Arg Gln Pro Asn Gln Phe Pro Asp Ser Ala Glu
            340                 345                 350

Ala Ala Met Lys Leu Thr Asn Thr Ser Asp Ala Gln Tyr Phe Leu Arg
        355                 360                 365

Glu Val Gly His Glu Ala Ile Asp Gly Ala Ala Phe His Tyr Ser Ile
        370                 375                 380

Tyr Arg Ala Leu Thr Arg Phe Leu Gly Met Asp Gly Asn Leu Ala Ala
385                 390                 395                 400

Gly Tyr Asp Val Pro Val Asp Trp Val Asp Ala Trp Asn Leu Met Leu
                405                 410                 415

Gln Ser Asn Asp Leu Val Asn Ala Asn Thr Gly Lys Phe Asp Pro Arg
            420                 425                 430

His Met Tyr Gly Ala Thr Asn Gln Asp Val Phe Arg Trp Pro Thr Val
        435                 440                 445

Glu Lys Gly Val Glu Arg Gln Leu Leu Gly Leu Tyr Ile Thr Thr Leu
450                 455                 460

Leu Leu Pro Gly Ile Pro Leu Leu Leu Trp Gly Glu Glu Gln Ala Phe
465                 470                 475                 480

Tyr Val Leu Asp Ala Thr Ala Ser Asn Tyr Ile Tyr Gly Arg Gln Ala
                485                 490                 495

Met Ser Pro Ala Thr Ala Trp Arg Asp His Gly Cys Phe Ser Leu Glu
            500                 505                 510

Ser Ser Gln Tyr Tyr Asn Trp Pro Ile Glu Ser Gly Arg Gln Gly Cys
        515                 520                 525

His Asp Pro Thr Val Ala Tyr Asp His Arg Asp Pro Ser His Pro Val
        530                 535                 540

Arg Asn Ile Ile Lys His Met Tyr Gln Met Arg Glu Gln Phe Pro Val
545                 550                 555                 560

Leu Asn Asp Gly Tyr Thr Ile Gln Lys Leu Ser Asn His Thr Glu Asp
```

```
            565                 570                 575
Val Tyr Tyr Leu Gly Ser Asn Gly Thr Ala Thr Glu Thr Gly Leu Trp
            580                 585                 590

Ser Ile Leu Arg Asp Val Asn Ala Asp Val Gln Asp Leu Gly Ser Asp
            595                 600             605

Ala Lys Asn Gln Pro Val Trp Leu Val Tyr His Asn Thr Asn Arg Thr
610                 615                 620

Ile Asp Tyr Lys Phe Asp Cys Ser Asp Asn Asp Thr Ala Leu Ile Ala
625                 630                 635                 640

Pro Phe Asp Ser Gly Thr Trp Val Lys Asn Leu Phe His Pro Tyr Asp
                645                 650                 655

Glu His Gln Leu Ile Asp Ser Pro Thr Lys Leu Gly Leu Asn Gly Ser
                660                 665                 670

Thr Ala Tyr Ser Gly Cys Leu Ala Asn Met Thr Met Ser Ala Tyr Glu
                675                 680                 685

Phe Arg Ala Tyr Val Pro Lys Thr Arg Phe Thr Lys Pro Arg Pro Met
            690                 695                 700

Ile Thr Lys Phe Thr Pro Gly His Asp Val Pro Ile Arg Ser Thr Val
705                 710                 715                 720

Ala Pro Asn Ala Asp Glu Asn Val Glu Val Glu Ile Tyr Phe Ser Glu
                725                 730                 735

Glu Met Asp Cys Asp Ser Val Thr Lys Ser Ile Thr Leu Ser Ser Ser
                740                 745                 750

Thr Glu Ile Gly Lys Ala Pro Ser Val Asp Ser Gly Ser Val Asn Cys
            755                 760                 765

Lys Ser Val Pro Ala Thr Asn Thr Ser Trp Thr Gly Gln Ile Pro Gly
770                 775                 780

Val Trp Met Trp Ala Ala Asn Leu Thr Gly Val Tyr Asn Gly Ile His
785                 790                 795                 800

Arg Leu Thr Val Asn Asn Val Ser Thr Glu Ser Gly Asn Ala Thr Thr
                805                 810                 815

Asn Ala Val Asp His Phe Leu Phe Arg Ile Gly Gln Ile Asp Asn Pro
                820                 825                 830

Met Ile Phe Ser Ser Ala Asn Tyr Ser Thr Ser Leu Leu His Lys Glu
            835                 840                 845

Ser Asn Gly Thr Leu Phe Ile Gln His His Ala Gly Ala Asp Lys
            850                 855                 860

Tyr Arg Tyr Ser Thr Asn Trp Gly Thr Thr Phe Ser Asp Trp Ile Asp
865                 870                 875                 880

Tyr Arg Gly Gly Asn Asp Thr Ile Glu Glu Leu Glu Trp Ser Gly Thr
                885                 890                 895

Lys Lys Gln Ser Trp Lys Gly Asn His Val Arg Val Glu Tyr Trp Ser
                900                 905                 910

Arg Trp Thr Gly Ser Ser Asp Tyr Val Gln Glu Gly Asp Ala Gly Trp
            915                 920                 925

Asn Glu Asn Val Pro Arg Arg Phe Pro His Val Phe Phe Asn Gly Pro
            930                 935                 940

Tyr Asn Gln Tyr Gly Tyr Asp Ala Gly Leu Asp Asn Val Val Arg Gln
945                 950                 955                 960

Asp Ser Val Asp Gly Leu Trp Lys Tyr His Phe Thr Ala Glu Trp Pro
                965                 970                 975

Ala Gln Ala Gln Leu Asn Ile Trp Gly Met Asn Pro Asp Gly Glu Pro
            980                 985                 990
```

-continued

```
Asp Gln Ser Trp Val Leu Gly Asp Ala Asp Asn Asp Ser Val Leu Asp
        995                 1000                1005

Arg Met Pro Pro Ser Ser Leu Ser Ala Thr Leu Ile Asn Ile Thr
    1010                1015                1020

Glu His Pro Pro Ser Pro Tyr Ile Ser Trp Asn Ile Phe Ile Asp
    1025                1030                1035

Asp Gly Thr Met Arg Phe Gln Leu Phe Pro Val Gly His Gln Asn
    1040                1045                1050

Thr Gln Ile Ala Met Tyr Val Leu Phe Trp Ile Ile Pro Val Ile
    1055                1060                1065

Thr Gly Ala Ala Gly Val Trp Ala Phe Met Lys Ser Phe Tyr Lys
    1070                1075                1080

Val Lys Phe Asn Gln Val Gly Val Ser Glu Lys His Gln Met Ile
    1085                1090                1095

Pro Leu Ala Leu Arg Arg Lys Phe Lys Arg Asn Arg Asn Arg Gly
    1100                1105                1110

Gly Asp Glu Glu Asn Ser Asn Pro Leu Met Arg Leu Ala Asn Lys
    1115                1120                1125

Ser Gly Phe Leu Gln Thr Asp Thr Ala Ile Gly Gly Ala Ala Ser
    1130                1135                1140

Gly Lys Arg Arg Met Val Leu Ile Ala Thr Met Glu Tyr Asp Ile
    1145                1150                1155

Glu Asp Trp Ala Ile Lys Ile Lys Ile Gly Gly Leu Gly Val Met
    1160                1165                1170

Ala Gln Leu Met Gly Lys Thr Leu Gly His Gln Asp Leu Ile Trp
    1175                1180                1185

Val Val Pro Cys Val Gly Gly Val Asp Tyr Pro Val Asp Lys Pro
    1190                1195                1200

Ala Glu Pro Met His Val Thr Ile Leu Gly Asn Ser Tyr Glu Val
    1205                1210                1215

Gln Val Gln Tyr His Val Leu Asn Asn Ile Thr Tyr Val Leu Leu
    1220                1225                1230

Asp Ala Pro Val Phe Arg Gln Gln Ser Lys Ser Glu Pro Tyr Pro
    1235                1240                1245

Ala Arg Met Asp Asp Leu Asn Ser Ala Ile Tyr Tyr Ser Ala Trp
    1250                1255                1260

Asn Gln Cys Ile Ala Glu Ala Cys Lys Arg Phe Pro Ile Asp Leu
    1265                1270                1275

Tyr His Ile Asn Asp Tyr His Gly Ser Leu Ala Pro Leu Tyr Leu
    1280                1285                1290

Leu Pro Asp Thr Val Pro Ala Cys Leu Ser Leu His Asn Ala Glu
    1295                1300                1305

Phe Gln Gly Leu Trp Pro Met Arg Thr Gln Lys Glu Lys Glu Glu
    1310                1315                1320

Val Cys Ser Val Phe Asn Leu Asp Ile Glu Thr Val Arg His Tyr
    1325                1330                1335

Val Gln Phe Gly Glu Val Phe Asn Leu Leu His Ser Gly Ala Ser
    1340                1345                1350

Tyr Leu Arg Val His Gln Gln Gly Phe Gly Ala Val Gly Val Ser
    1355                1360                1365

Lys Lys Tyr Gly Lys Arg Ser Tyr Ala Arg Tyr Pro Ile Phe Trp
    1370                1375                1380
```

-continued

| | | | | | | | | | | |
|---|---|---|---|---|---|---|---|---|---|---|
| Gly | Leu | Arg | Lys | Val | Gly | Asn | Leu | Pro | Asn | Pro | Asp | Pro | Ser | Asp |
| | 1385 | | | | 1390 | | | | 1395 | | | | | |
| Val | Gly | Glu | Trp | Ser | Lys | Glu | Gln | Ala | Ser | Ala | Met | Gly | Asp | Asn |
| | 1400 | | | | 1405 | | | | 1410 | | | | | |
| Val | Ser | Val | Asp | Pro | Thr | Tyr | Glu | Ala | Gly | Arg | Gly | Asp | Leu | Lys |
| | 1415 | | | | 1420 | | | | 1425 | | | | | |
| Arg | Gln | Ala | Gln | Glu | Trp | Ala | Gly | Leu | Glu | Gln | Asn | Pro | Asp | Ala |
| | 1430 | | | | 1435 | | | | 1440 | | | | | |
| Asp | Leu | Leu | Val | Phe | Val | Gly | Arg | Trp | Ser | Met | Gln | Lys | Gly | Val |
| | 1445 | | | | 1450 | | | | 1455 | | | | | |
| Asp | Leu | Ile | Ala | Asp | Val | Met | Pro | Ala | Val | Leu | Glu | Ala | Arg | Pro |
| | 1460 | | | | 1465 | | | | 1470 | | | | | |
| Asn | Val | Gln | Leu | Ile | Cys | Val | Gly | Pro | Val | Ile | Asp | Leu | Tyr | Gly |
| | 1475 | | | | 1480 | | | | 1485 | | | | | |
| Lys | Phe | Ala | Ala | Leu | Lys | Leu | Asp | His | Met | Met | Lys | Val | Tyr | Pro |
| | 1490 | | | | 1495 | | | | 1500 | | | | | |
| Gly | Arg | Val | Phe | Ser | Arg | Pro | Glu | Phe | Thr | Ala | Leu | Pro | Pro | Tyr |
| | 1505 | | | | 1510 | | | | 1515 | | | | | |
| Ile | Phe | Ser | Gly | Ala | Glu | Phe | Ala | Leu | Ile | Pro | Ser | Arg | Asp | Glu |
| | 1520 | | | | 1525 | | | | 1530 | | | | | |
| Pro | Phe | Gly | Leu | Val | Ala | Val | Glu | Phe | Gly | Arg | Lys | Gly | Ala | Leu |
| | 1535 | | | | 1540 | | | | 1545 | | | | | |
| Gly | Ile | Gly | Ala | Arg | Val | Gly | Leu | Gly | Gln | Met | Pro | Gly | Trp |
| | 1550 | | | | 1555 | | | | 1560 | | | | | |
| Trp | Tyr | Asn | Val | Glu | Ser | Thr | Ala | Thr | Ser | His | Leu | Leu | Val | Gln |
| | 1565 | | | | 1570 | | | | 1575 | | | | | |
| Phe | Lys | Leu | Ala | Ile | Asp | Ala | Ala | Leu | Ser | Ser | Lys | Thr | Glu | Thr |
| | 1580 | | | | 1585 | | | | 1590 | | | | | |
| Arg | Ala | Met | Met | Arg | Ala | Arg | Ser | Ala | Lys | Gln | Arg | Phe | Pro | Val |
| | 1595 | | | | 1600 | | | | 1605 | | | | | |
| Ala | Gln | Trp | Val | Glu | Asp | Leu | Glu | Ile | Leu | Gln | Thr | Thr | Ala | Ile |
| | 1610 | | | | 1615 | | | | 1620 | | | | | |
| Gln | Val | His | Asn | Lys | Glu | Leu | Val | Lys | His | Asn | Gly | Arg | Pro | Phe |
| | 1625 | | | | 1630 | | | | 1635 | | | | | |
| Thr | Pro | Ser | Gly | Thr | Thr | Pro | Gly | Gly | Ile | Leu | Ser | Gln | Pro |
| | 1640 | | | | 1645 | | | | 1650 | | | | | |
| Ser | Ser | Pro | Leu | Met | Pro | Pro | Gly | Met | Gln | Thr | Pro | Leu | Ala | His |
| | 1655 | | | | 1660 | | | | 1665 | | | | | |
| Ser | Arg | Glu | Ser | Ser | Tyr | Ser | Asn | Leu | Asn | Arg | Leu | Ser | Glu | Tyr |
| | 1670 | | | | 1675 | | | | 1680 | | | | | |
| Val | Thr | Asp | Pro | Lys | Thr | Asn | Tyr | Ser | Arg | Asp | Ile | Ser | Pro | Ser |
| | 1685 | | | | 1690 | | | | 1695 | | | | | |
| Gly | Thr | Glu | Lys | Pro | Arg | Ser | Gly | Leu | Gln | Arg | Gln | Leu | Ser | Leu |
| | 1700 | | | | 1705 | | | | 1710 | | | | | |
| Gly | Val | Arg | Ser | Gly | Pro | Gly | His | Gln | Glu | Arg | Arg | Gly | Arg | Arg |
| | 1715 | | | | 1720 | | | | 1725 | | | | | |
| Gly | Arg | Gln | Arg | Asp | Ser | Ile | Pro | Glu | His | Glu | Asp | Thr | Ala | Gly |
| | 1730 | | | | 1735 | | | | 1740 | | | | | |
| Ala | Met | Thr | Asp | Val | Glu | Glu | Asp | His | Glu | Asp | Ile | Gly | Asp | Gln |
| | 1745 | | | | 1750 | | | | 1755 | | | | | |
| Gln | Asp | Ala | Asp | Asp | Glu | Tyr | Thr | Leu | Thr | Pro | Ala | Gln | Val | Glu |
| | 1760 | | | | 1765 | | | | 1770 | | | | | |
| Glu | Gly | Arg | Arg | Leu | Gln | Ala | Val | Gln | Gln | Gly | Val | Gly | Met |

-continued

```
                1775                1780                1785
Pro Thr Ser Pro Gly Val Arg Arg Tyr Ser Gln Asp Ser Leu His
    1790                1795                1800

Pro Arg Gln Leu Pro Ser Ser Pro Gly Pro Val Pro Pro Pro Thr
    1805                1810                1815

Gln Ser Leu Leu Pro Pro Pro Arg Leu Gly Asp Ala Gly Ser Arg
    1820                1825                1830

Leu Ser Ser Ala Ser Val Leu Ser Leu Asp Ser Val Val Gly Thr
    1835                1840                1845

Lys Thr Asp Phe Lys Leu Gln Lys Val Asp Pro Phe Phe Thr Asp
    1850                1855                1860

Ser Thr Gly Glu Tyr Tyr Lys Ala Phe Asp Lys Arg Leu Val Gly
    1865                1870                1875

Leu Asn Gly Ser Asn Ser Glu Ser Gln Leu Cys Ile Glu Glu Tyr
    1880                1885                1890

Leu Ile Lys Ser Glu Lys Glu Trp Phe Asp Lys Phe Arg Asp Ala
    1895                1900                1905

Arg Leu Gly Arg Leu Lys Ser Pro Ala Ser Ser Val Phe Arg Asp
    1910                1915                1920

Lys His Gly Ala Ser Pro Val Gly Ser Tyr Tyr Asp Asp Thr Gly
    1925                1930                1935

Ser Arg Val Ser Gly Asp Tyr Asp Arg Glu Ser Arg Asp Thr Glu
    1940                1945                1950

Asp Asp Glu Phe Leu Leu Gly Lys Asp Tyr Val Pro Pro Thr Gly
    1955                1960                1965

Leu Arg Lys Trp Met Gln Ile Arg Val Gly Asp Trp Pro Val Tyr
    1970                1975                1980

Ser Leu Phe Leu Ala Leu Gly Gln Ile Ile Ala Ala Asn Ser Tyr
    1985                1990                1995

Gln Val Thr Leu Leu Thr Gly Glu Val Gly Glu Thr Ala Glu Lys
    2000                2005                2010

Leu Tyr Gly Ile Ala Thr Thr Tyr Leu Ile Thr Ser Ile Leu Trp
    2015                2020                2025

Trp Leu Val Phe Arg Tyr Phe Lys Ser Val Val Cys Leu Ser Ala
    2030                2035                2040

Pro Trp Phe Phe Tyr Gly Leu Ala Phe Leu Leu Ile Gly Ser Ala
    2045                2050                2055

His Phe Glu Pro Asn Ser Phe Asn Arg Gly Trp Ile Gln Asn Ile
    2060                2065                2070

Gly Ser Gly Cys Tyr Ala Ala Ala Ser Ser Ser Gly Ser Ile Phe
    2075                2080                2085

Phe Ala Leu Asn Phe Gly Asp Glu Gly Gly Ala Pro Val Glu Thr
    2090                2095                2100

Trp Ile Phe Arg Ala Cys Leu Ile Gln Gly Ile Gln Ser Ala Tyr
    2105                2110                2115

Ile Ile Gly Leu Trp Tyr Trp Gly Ser Thr Leu Thr Lys Ala Ser
    2120                2125                2130

Ser Gln Gly Leu Leu Thr Ser Thr Asn Asn Ile Ala Asn Ser Trp
    2135                2140                2145

Lys Met Thr Ala Ile Cys Tyr Pro Ile Ala Ile Phe Leu Trp Ala
    2150                2155                2160

Val Gly Leu Leu Leu Leu Phe Gly Leu Pro Asn Tyr Tyr Arg Gln
    2165                2170                2175
```

-continued

```
Thr Pro Gly Lys Val Ala Ser Phe Tyr Lys Ser Val Phe Arg Arg
    2180            2185            2190

Lys Ile Val Leu Trp Asn Phe Val Ala Val Ile Leu Gln Asn Phe
    2195            2200            2205

Phe Leu Ser Ala Pro Tyr Gly Arg Asn Trp Gly Phe Leu Trp Ser
    2210            2215            2220

Ser Asn His Ala Lys Ala Trp Gln Ile Val Ile Leu Cys Ile Val
    2225            2230            2235

Phe Tyr Gly Phe Val Trp Ala Gly Phe Leu Phe Val Val Ser Arg
    2240            2245            2250

Tyr Phe Lys Ser His Ser Trp Phe Leu Pro Val Phe Ala Cys Gly
    2255            2260            2265

Leu Gly Ala Pro Arg Phe Ile Gln Ile Trp Trp Gly Val Ser Gly
    2270            2275            2280

Ile Gly Tyr Phe Leu Pro Trp Val Ser Gly Gly Tyr Leu Gly Gly
    2285            2290            2295

Ala Leu Ala Ser Arg Ser Leu Trp Leu Trp Leu Gly Val Leu Asp
    2300            2305            2310

Ser Ile Gln Gly Leu Gly Phe Gly Ile Ile Leu Leu Gln Thr Leu
    2315            2320            2325

Thr Arg Met His Met Leu Phe Thr Leu Ile Cys Ser Gln Val Leu
    2330            2335            2340

Gly Ser Ile Ala Thr Ile Cys Ala Arg Ala Phe Ala Pro Asn Asn
    2345            2350            2355

Val Gly Pro Gly Pro Val Ser Pro Asp Pro Thr Phe Gly Gly Ser
    2360            2365            2370

Ala Val Ala Asn Ala Trp Phe Trp Val Ala Leu Phe Cys Gln Leu
    2375            2380            2385

Leu Ile Ser Glu Asp Gly Tyr Ala Cys Asp Asn Pro Asn Tyr Asn
    2390            2395            2400

Asn Asn Leu Gln
    2405
```

AMYLASE-DEFICIENT STRAIN

CROSS REFERENCE TO RELATED APPLICATIONS

This application is a §371 National Stage Application of PCT/EP2013/065347, filed Jul. 19 2013, which claims priority to EP 12177173.7, filed Jul. 19, 2012, EP 12177171.1, filed Jul. 19, 2012, U.S. 61/673,589, filed Jul. 19, 2012 and U.S. 61/673,607, filed Jul 19, 2012.

BACKGROUND

Field of the Invention

The present invention relates to a mutant microbial host cell which has been modified, preferably in its genome, to result in a deficiency in the production of a polypeptide having amylase activity, to a method to produce the mutant microbial host cell and to a method to produce a compound of interest using said mutant microbial host cell.

Description of Related Art

An ever increasing number of products is produced by microbial fermentation at industrial scale. Such products range from primary and secondary metabolites, such as e.g. citric acid and antibiotics, respectively, to proteins, enzymes and even complete microorganisms, e.g. in the form of bakers yeast or biomass.

Different host cell types may be used for different production processes. For example: mammalian cell lines are used for antibody production; fungal cells are preferred organisms for production of polypeptides and secondary metabolites; bacterial cells are preferred for small metabolite and antibiotic production; and plant cells are preferred for taste and flavor compounds. An important aspect in the production of valuable products by microbial fermentation is optimization of the productivity of the microbial cells.

Recombinant techniques are widely employed for optimization of the productivity of such cells and/or the processes in which they are used. This can involve a multitude of options.

Some techniques will aim at the over expression of a gene of interest coding for the product or coding for a compound related to the production of the product by the host cell. Gene expression can be modulated in several ways. For example the gene of interest can be placed in the host cell under the expression control of a strong promoter, or it can be placed under the control of a promoter activated by a transcriptional activator which activator can be up-regulated or down-regulated. In yet an alternative approach gene expression can be improved by increasing the copy number of the gene of interest in the host cell used to express the gene. Yet other approaches aiming at improving the productivity of a compound of interest by a host cell can involve deletion or inactivation of competing pathways, changing compartmentalization of enzymes, increasing protein or metabolite secretion, increasing organelle content and the like.

Another important aspect in the production of valuable products by microbial fermentation is the quality and purity of said products after the fermentation and in the final product formulation. These will depend on the specific product quality demands and the final application of the product. Most commercial products produced by microbial fermentation have requirements in their physical appearance (color, odor). Also impurities related to the process (e.g., the presence of unfermented sugar from the media) and the microorganism used (e.g., metabolites produced during the fermentation) can influence the quality of the product. Dealing with these issues requires incorporating purification steps after recovery of the product from the fermentation broth.

If the valuable product is secreted into the nutrient medium, the product can be isolated directly from the medium. If the product is not secreted, it can be isolated from cell lysates. The product may be isolated from the nutrient medium by conventional procedures including, but not limited to, centrifugation, filtration, extraction, spray drying, evaporation, or precipitation. A variety of procedures known in the art including, but not limited to, chromatography (e. g., ion exchange, affinity, hydrophobic, chromatofocusing, and size exclusion), electrophoretic procedures (e.g., preparative isoelectric focusing), differential solubility (e. g., ammonium sulfate precipitation), or extraction (see, e.g., *Protein Purification*, J.-C. Janson and Lars Ryden, editors, VCH Publishers, New York, 1989) can be used at this purpose. The use of several purification steps however will increase production costs. In case the product is an enzyme the presence of other enzyme activities, derived from the production microorganism, should be avoided as it can interfere with the application or, more commonly, negatively affect the product stability.

There is therefore a need to develop microorganisms used to express useful products that combine the capacity for expression of commercial quantities thereof while being deficient in the production of enzymes that can complicate recovery, downstream processing or compromise final purity of the products and/or be detrimental in product applications.

SUMMARY

The present invention relates to a mutant microbial host cell which has been modified, preferably in its genome, to result in a deficiency in the production of a polypeptide having amylase activity, preferably α-amylase activity, selected from the group consisting of:

a. a polypeptide according to SEQ ID NO: 3 or 7 or a polypeptide at least 70% identical thereto;
b. a mature polypeptide comprised in SEQ ID NO: 3 or 7 or a polypeptide at least 70% identical thereto;
c. a polypeptide encoded by a polynucleotide according to SEQ ID NO: 1, 2, 5 or 6 or encoded by a polynucleotide at least 70% identical to SEQ ID NO: 1, 2, 5 or 6;
d. a polypeptide encoded by a polynucleotide capable of hybridising to a polynucleotide according to SEQ ID NO: 1, 2, 5 or 6 or capable of hybridising to the complementary strand of SEQ ID NO: 1, 2, 5 or 6;

if compared with a parent microbial host cell which has not been modified and measured under the same conditions.

The present invention further relates to a method of producing a mutant microbial host cell according to the invention comprising the steps of:

a. providing a parent microbial host cell;
b. modifying the parent microbial host cell, preferably modifying the genome of the parent microbial host cell to yield a mutant host cell which is deficient in the production of a polypeptide having amylase activity, preferably α-amylase activity, selected from the group consisting of:
   i. a polypeptide according to SEQ ID NO: 3 or 7 or a polypeptide at least 70% identical thereto;
   ii. a mature polypeptide comprised in SEQ ID NO: 3 or 7 or a polypeptide at least 70% identical thereto;

iii. a polypeptide encoded by a polynucleotide according to SEQ ID NO: 1, 2, 5 or 6 or encoded by a polynucleotide at least 70% identical to SEQ ID NO: 1, 2, 5 or 6;

iv. a polypeptide encoded by a polynucleotide capable of hybridising to a polynucleotide according to SEQ ID NO: 1, 2, 5 or 6 or capable of hybridising to the complementary strand of a polynucleotide according to SEQ ID NO: 1, 2, 5 or 6;

if compared with the parent microbial host cell and measured under the same conditions.

The invention relates as well to a method for the production of a compound of interest by microbial fermentation comprising:

a. providing a mutant microbial host cell according to the invention or produced according to a method for producing a mutant microbial host cell according to the invention capable of expressing the compound of interest, b. culturing said microbial host cell under conditions conducive to the expression of the compound of interest, c. optionally isolating the compound of interest from the culture medium.

BRIEF DESCRIPTION OF THE SEQUENCE LISTING

Figure 1:
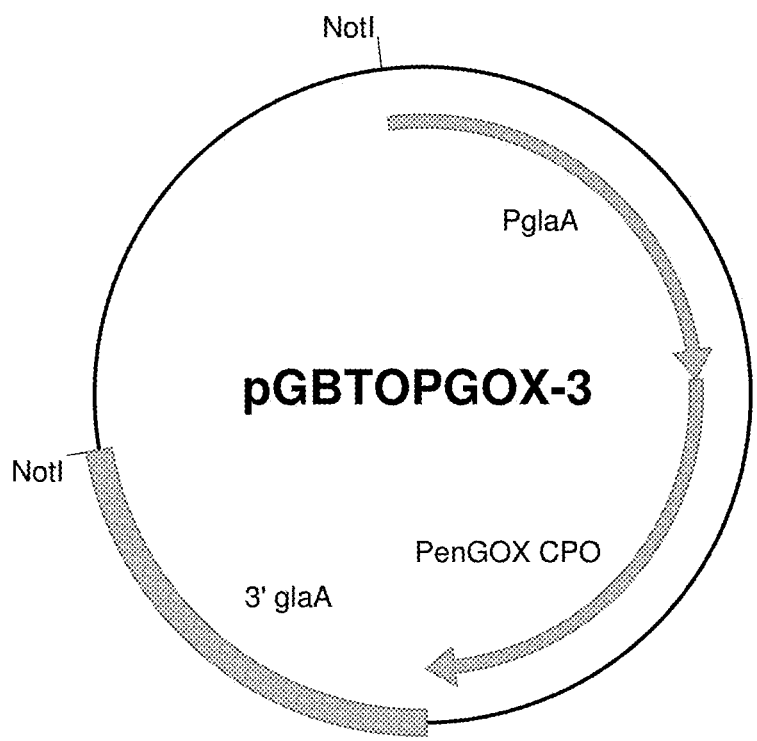
FIG. 1 depicts pGBTOPGOX-3, the pGBTOP-12 based plasmid used for expression of the *Penicillium chrysogenum* glucose oxidase enzyme gene with a layout for expression driven by the glucoamylase promoter and targeted integration in the adapted BamHI amplicon.

SEQ ID NO: 1 sets out the genomic sequence of the amyC amylase gene from *Aspergillus niger*, including 2 kb upstream and downstream flanking regions. The genomic sequence comprises the cDNA sequence according to SEQ ID NO: 2.

SEQ ID NO: 2 sets out the cDNA sequence of the amyC amylase gene (short sequence) from *A. niger*.

SEQ ID NO: 3 sets out the amino acid sequence of the amyC amylase protein (short sequence) from *A. niger*.

SEQ ID NO: 4 sets out the amino acid sequence of the AmyC mature amylase protein (short sequence) corresponding to amino acid 17-493 of SEQ ID NO: 3.

SEQ ID NO: 5 sets out the genomic sequence of the amyC amylase gene (long sequence) from *Aspergillus niger*, including 2 kb upstream and downstream flanking regions. The genomic sequence comprises the cDNA sequence according to SEQ ID NO: 6.

SEQ ID NO: 6 sets out the cDNA sequence of the amyC amylase gene (long sequence) from *A. niger*.

SEQ ID NO: 7 sets out the amino acid sequence of the amyC amylase protein (long sequence) from *A. niger*.

SEQ ID NO: 8 sets out the amino acid sequence of the AmyC mature amylase protein (long sequence) corresponding to amino acid 17-524 of SEQ ID NO: 7.

SEQ ID NO: 9 sets out the genomic sequence of the agdB gene from *Aspergillus niger*, including 2 kb upstream and downstream flanking regions. The genomic sequence comprises the cDNA sequence according to SEQ ID NO: 10.

SEQ ID NO: 10 sets out the cDNA sequence of the agdB gene from *A. niger*.

SEQ ID NO: 11 sets out the amino acid sequence of the agdB protein from *A. niger*.

SEQ ID NO: 12 sets out the genomic sequence of the agdA gene from *Aspergillus niger*, including 2 kb upstream and downstream flanking regions. The genomic sequence comprises the cDNA sequence according to SEQ ID NO: 13.

SEQ ID NO: 13 sets out the cDNA sequence of the agdA gene from *A. niger*.

SEQ ID NO: 14 sets out the amino acid sequence of the agdA protein from *A. niger*.

SEQ ID NO: 15 sets out the codon pair optimized cDNA sequence of the glucose oxidase from *Penicillium chrysogenum*.

SEQ ID NO: 16 sets out the amino acid sequence of the glucose oxidase from *Penicillium chrysogenum*.

SEQ ID NO: 17 sets out the genomic sequence of the agsE gene from *Aspergillus niger*, including 2 kb upstream and downstream flanking regions. The genomic sequence comprises the cDNA sequence according to SEQ ID NO: 18.

SEQ ID NO: 18 sets out the cDNA sequence of the agsE gene from *A. niger*.

SEQ ID NO: 19 sets out the amino acid sequence of the AgsE protein from *A. niger*.

SEQ ID NO: 20 sets out the amino acid sequence of the mature AgsE protein corresponding to amino acid 20-2426 of SEQ ID NO: 19.

All nucleotide sequences for *A. niger* genes and protein sequences and their genomic context can be derived from public databases available for example from the NCBI at http://www.ncbi.nlm.nih.gov/ or EMBL (http://www.ebi.ac.uk/embl/). For example the genome sequence of CBS 513.88 at EMBL has accession numbers no. AM269948-AM270415.

DETAILED DESCRIPTION OF A PREFERRED EMBODIMENT

The present invention relates to a mutant microbial host cell which has a deficiency in the production of the amyC amylase protein. Such a mutant microbial cell is modified, preferably in its genome, to result in a deficiency in the production of a polypeptide having amylase activity, preferably α-amylase activity, selected from the group consisting of:

a. a polypeptide according to SEQ ID NO: 3 or 7 or a polypeptide at least 70% identical thereto;

b. a mature polypeptide comprised in SEQ ID NO: 3 or 7 or a polypeptide at least 70% identical thereto;

c. a polypeptide encoded by a polynucleotide according to SEQ ID NO: 1, 2, 5 or 6 or encoded by a polynucleotide at least 70% identical to SEQ ID NO: 1, 2, 5 or 6;

d. a polypeptide encoded by a polynucleotide capable of hybridising to a polynucleotide according to SEQ ID NO: 1, 2, 5 or 6 or capable of hybridising to the complementary strand of a polynucleotide according to SEQ ID NO: 1, 2, 5 or 6;

if compared with a parent microbial host cell which has not been modified and measured under the same conditions.

It has been surprisingly found that when the mutant microbial host cell according to the invention and which is capable of expressing a compound of interest is used in a method to produce a compound of interest, for example an enzyme, the amylase side activity in the compound of interest is considerably lowered. This is very advantageous when the compound of interest is an enzyme used in specific (food) applications, e.g. in those applications wherein uncontrolled degradation of starch components is not desirable (e.g. preparation of baked products, mayonnaise light, etcetera).

In particular, it has been found that when a mutant microbial host cell according to the invention (and which is capable of expressing a compound of interest is used in a method to produce a compound of interest, for example an enzyme) also comprises disruptions in the most important and abundant amylases (glucoamylase glaA, alpha-amylase amyBII and ΔamyBI and acid stable alpha-amylase amyA) the effect of the disruption of AmyC is especially dramatic. This is surprising since other amy disruptions showed no pronounced effect on alpha-amylase activity (when used in combination with disruptions to glucoamylase glaA, alpha-amylase amyBII and ΔamyBI and acid stable alpha-amylase amyA).

This means that specifically amyC (An04g06930) disruption results in an important reduction in alpha-amylase activity, especially in the context of a mutant microbial host cell which also has disruptions to glucoamylase glaA, alpha-amylase amyBII and ΔamyBI and acid stable alpha-amylase amyA.

Within the context of the present invention "measured under the same conditions" or "analysed under the same conditions" means that the mutated microbial host cell and the parent microbial host cell are cultivated under the same conditions and that the amount and/or activity of the polypeptide in which the mutant microbial host cell is deficient, if compared to the parent microbial host cell, is measured in the microbial host cell and in the parent host cell, respectively, using the same conditions, preferably by using the same assay and/or methodology, more preferably within the same experiment.

A "mutant microbial host cell" is herewith defined as a microbial host cell derived from a parent host cell and which has been modified, preferably in its genome, if compared to the parent host cell to obtain a different genotype and/or a different phenotype if compared to the parent host cell from which it is derived.

The modification can either be effected by
a) subjecting the parent microbial host cell to recombinant genetic manipulation techniques; and/or
b) subjecting the parent microbial host cell to (classical) mutagenesis; and/or
c) subjecting the parent microbial host cell to an inhibiting compound or composition.

A "mutant microbial host cell which has been modified, preferably in its genome, to result in a deficiency in the production of a product", for example of a product such as a polypeptide having amylase activity according to SEQ ID NO: 3 or 7, is herein defined as a mutant microbial host cell which has been modified, preferably in its genome, to result in a phenotypic feature wherein the cell: a) produces less of the product or produces substantially no product and/or b) produces a product having a decreased activity or decreased specific activity or a product having no activity or no specific activity and combinations of one or more of these possibilities as compared to the parent microbial host cell that has not been modified, when analysed under the same conditions.

In the context of the present invention a polypeptide having amylase activity, preferably α-amylase activity is a polypeptide selected from the group consisting of:
a. a polypeptide according to SEQ ID NO: 3 or 7 or a polypeptide at least 70% identical to either thereto;
b. a mature polypeptide comprised in SEQ ID NO: 3 or 7 or a polypeptide at least 70% identical to either thereto;
c. a polypeptide encoded by a polynucleotide according to SEQ ID NO: 1, 2, 5 or 6 or encoded by a polynucleotide at least 70% identical to SEQ ID NO: 1, 2, 5 or 6;
d. a polypeptide encoded by a polynucleotide capable of hybridising to a polynucleotide according to SEQ ID NO: 1, 2, 5 or 6 or to the complementary strand of a polynucleotide according to SEQ ID NO: 1, 2, 5 or 6.

The polypeptide having amylase activity, preferably having α-amylase activity as defined herein is preferably an acid stable α-amylase. In one embodiment the polypeptide having α-amylase activity has a temperature optimum, as measured according to the Megazyme CERALPHA alpha-amylase assay kit, Megazyme International Ireland Ltd., Co. Wicklow, Ireland, at pH 4, of 45-57° C., more preferably of 48-54° C., even more preferably of about 50° C. Preferably the polypeptide having α-amylase activity has a pH optimum, as measured at 50° C. according to the Megazyme CERALPHA alpha-amylase assay kit, Megazyme International Ireland Ltd., Co. Wicklow, Ireland, of 3.8-5, more preferably of 4-4.5.

A polypeptide according to SEQ ID NO: 3 or 7 corresponds to the amylase AmyC from *Aspergillus niger* (Yuan X.-L., van der Kaaij R. M., van den Hondel C. A. M. J. J., Punt P. J., van der Marel M. J. E. C., Dijkhuizen L., Ram A. F. J. *Mol. Genet. Genomics* (2008) 279: 545-561). The polypeptide according to SEQ ID NO: 3 or 7 is encoded by the amylase gene amyC (genomic DNA as depicted in SEQ ID NO: 1 and 5, cDNA as depicted in SEQ ID NO: 2 or SEQ ID NO: 6). The two genomic sequences, SEQ ID NO: 1 and 5 are identical. However, two different cDNAs and consequently two different polypeptides have been identified: a short form (cDNA=SEQ ID NO: 2 and polypeptide=SEQ ID NO: 3); and a long form (cDNA=SEQ ID NO: 6 and polypeptide=SEQ ID NO: 7).

In the context of the present invention a polypeptide having amylase activity, preferably having α-amylase activity, which is at least 70% identical to either of SEQ ID NO: 3 or SEQ ID NO: 7 is a polypeptide characterised by an amino acid sequence comprising one or more substitutions, deletions, and/or insertions of one or more amino acids if compared to the polypeptide of SEQ ID NO: 3 or 7, wherein the polypeptide which is at least 70% identical to SEQ ID NO: 3 or 7 has more or less (α-)amylase activity than the polypeptide according to SEQ ID NO:3 or 7. The polypeptide which is at least 70% identical to SEQ ID NO: 3 or 7 may e.g. be a natural variant, an orthologue or an in vitro generated variant of SEQ ID NO: 3 or 7 obtained using methods well known in the art such as e.g. classical mutagenesis, site-directed mutagenesis, DNA shuffling and in silico design. In the context of the present invention the polypeptide which is at least 70% identical to SEQ ID NO: 3 or 7 has preferably between 20% and 400% amylase activity if compared to SEQ ID NO:3 or 7 and measured under the same conditions, more preferably between 40 and 350% amylase activity, even more preferably between 50 and 300% amylase activity, between 70 and 250% amylase activity, between 80 and 200% amylase activity, most preferably approximately 100% amylase activity of the polypeptide according to SEQ ID NO: 3 or 7. With amylase activity it is herewith intended preferably α-amylase activity. For the measurement of amylase activity in the polypeptide according to SEQ ID NO: 3 or 7 and in the polypeptide at least 70% identical thereto any method known in the art for the measurement of said activity can be used. The only requirement is that the measurement of amylase activity in the polypeptide according to SEQ ID NO: 3 or 7 and in the polypeptide at least 70% identical thereto is preferably performed using the same method and/or assay and under the same conditions, preferably within the same experiment. Alpha-amylase activity may be measured according to methods known to those skilled in the art; e.g. it may be measured according to the well-established Ceralpha method (McCleary, B. V., McNally, M., Monaghan, D. & Mugford, D. C. (2002). "Measurement of α-amylase activity in white wheat flour, milled malt, and microbial enzyme preparations using the Ceralpha Assay". Collaborative study. *J. AOAC International*, 85, 1096-1102) using a Megazyme CERALPHA alpha-amylase assay kit, Megazyme International Ireland Ltd., Co. Wicklow, Ireland). In the experimental section a setup using the Megazyme CERALPHA α-amylases assay kit was used allowing a more sensitive determination of alpha-amylase activity. Other suitable methods for the determination of α-amylase are the well-known AACC method 22-01 (AACC. 1983 *Approved Methods of the American Association of* Cereal Chemists, 8th Edition. St. Paul, Minn.: American association of Cereal Chemists), the ASBC (International method) and the Farrand method.

Preferably the polypeptide having (α)-amylase activity is at least 80% identical to SEQ ID NO: 3 or 7, more preferably at least 85% identical to SEQ ID NO: 3 or 7, even more preferably at least 90% identical to SEQ ID NO: 3 or 7, most preferably at least 91%, for example at least 92%, 93%, 94%, at least 95% identical, at least 96%, 97%, 98%, at least 99% identical to SEQ ID NO: 3 or 7. Preferably the polypeptide having (α)-amylase activity is a polypeptide according to SEQ ID NO: 3 or 7. Preferably sequence identity is measured over the whole polypeptide sequence length.

The polypeptide which production the mutant microbial host cell according to the invention is deficient in, may be a mature polypeptide comprised in SEQ ID NO: 3 or 7. A mature polypeptide is defined herein as a polypeptide in its final form after translation, post-translational modifications, such as N-terminal processing, C-terminal processing, glycosylation, phosphorylation, secretion and optional removal of leader sequences by (proteolytic) cleavage. Signal peptides, propeptides and prepropeptides are in the art sometimes referred to as "leader sequences". The term "propeptide" is defined herein as a peptide fused in frame to the N-terminus of a polypeptide having biological activity. The resulting polypeptide is known as a propolypeptide which is lacking the polypeptide biological activity and can be converted into a mature, biologically active, polypeptide by catalytic or autocatalytic cleavage of the propeptide from the propolypeptide. A signal peptide and propeptide together are herein referred to as a "prepropeptide". The "signal sequence" is defined herein as a peptide being fused in frame to the N-terminus of a propeptide and the propeptide being fused in frame to the N-terminus of a polypeptide having biological activity. In some cases the propeptide is lacking and the signal sequence is fused in frame to the N-terminus of the polypeptide. The function of the signal sequence is to direct the polypeptide into the cell secretory pathway.

Therefore SEQ ID NO: 3 or 7 may be the sequence translated from the mRNA and prior to post translational modifications. SEQ ID NO: 3 or 7 may comprise additional amino acids at either the C-terminus and/or the N-terminus if compared to the mature polypeptide comprised therein. SEQ ID NO: 3 or 7 may e.g. comprise the mature polypeptide linked in frame to its signal peptide, propeptide and/or prepropeptide. In a preferred embodiment the mature polypeptide comprised in SEQ ID NO: 3 corresponds to amino acids 17-493 of SEQ ID NO: 3 and is set out in SEQ ID NO: 4. Therefore in one embodiment the mutant microbial host cell according to the invention is deficient in a polypeptide which is the mature polypeptide according to SEQ ID NO: 4. In another preferred embodiment the mature polypeptide comprised in SEQ ID NO: 7 corresponds to amino acids 17-524 of SEQ ID NO: 7 and is set out in SEQ ID NO: 8. Therefore in one embodiment the mutant microbial host cell according to the invention is deficient in a polypeptide which is the mature polypeptide according to SEQ ID NO: 8.

In the context of the present invention the polypeptide which production the mutant microbial cell is deficient in may be a polypeptide at least 70% identical to the mature polypeptide comprised in SEQ ID NO: 3 or 7 and having amylase activity, preferably α-amylase activity as defined herein. Preferably the polypeptide is at least 80% identical to the mature polypeptide as defined herein, more preferably at least 85% identical to the mature polypeptide as defined herein, even more preferably at least 90% identical to the mature polypeptide as defined herein, most preferably at least 91%, for example at least 92%, 93%, 94%, at least 95% identical, at least 96%, 97%, 98%, at least 99% identical to the mature polypeptide as defined herein. Preferably the polypeptide is the mature polypeptide according to SEQ ID NO: 4 or 8. Preferably sequence identity is measured over the whole polypeptide sequence length.

In the context of the present invention a polynucleotide according to SEQ ID NO: 1, 2 5 or 6 or a polynucleotide at least 70% identical to SEQ ID NO: 1, 2, 5 or 6 is a polynucleotide coding for a polypeptide having amylase activity, preferably α-amylase activity as defined herein, according to SEQ ID NO: 3 or 7, for a mature polypeptide comprised in SEQ ID NO: 3 or 7, for a polypeptide according to SEQ ID NO: 4 or 8 or for a polypeptide having amylase activity, preferably α-amylase activity, and having at least 70% identity to SEQ ID NO: 3 or 7, for a polypeptide having at least 70% identity to a mature polypeptide comprised in SEQ ID NO: 3 or 7, for a polypeptide having at least 70% identity to a mature polypeptide according to SEQ ID NO: 4 or 8 as defined above. In the context of the present invention a polynucleotide at least 70% identical to SEQ ID NO: 1, 2, 5 or 6 is a polynucleotide characterised by an nucleotide sequence comprising one or more substitutions, deletions, and/or insertions of one or more nucleotides if compared to the polynucleotide of SEQ ID NO: 1, 2, 5 or 6. Preferably the polynucleotide is at least 80% identical to SEQ ID NO: 1, 2, 5 or 6, more preferably at least 85% identical to SEQ ID NO: 1, 2, 5 or 6, even more preferably at least 90% identical to SEQ ID NO: 1, 2, 5 or 6, most preferably at least 91%, 92%, 93%, 94%, at least 95% identical, at least 96%, 97%, 98%, at least 99% identical to SEQ ID NO: 1, 2, 5 or 6. Preferably the polynucleotide is a polynucleotide according to SEQ ID NO:1, 2, 5 or 6.

For the purpose of this invention, it is defined here that in order to determine the percentage of sequence identity of two amino acid sequences or of two nucleic acid sequences, the sequences are aligned for optimal comparison purposes. In order to optimize the alignment between the two sequences gaps may be introduced in any of the two sequences that are compared. Such alignment can be carried out over the full length of the sequences being compared. Alternatively, the alignment may be carried out over a shorter length, for example over about 20, about 50, about 100 or more nucleic acids/based or amino acids. The sequence identity is the percentage of identical matches between the two sequences over the reported aligned region.

A comparison of sequences and determination of percentage of sequence identity between two sequences can be accomplished using a mathematical algorithm. The skilled person will be aware of the fact that several different computer programs are available to align two sequences and determine the identity between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley). The percentage of sequence identity between two amino acid sequences or between two nucleotide sequences may be determined using the Needleman and Wunsch algorithm for the alignment of two sequences. (Needleman, S. B. and Wunsch, C. D. (1970) J. Mol. Biol. 48, 443-453). Both amino acid sequences and nucleotide sequences can be aligned by the algorithm. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, P. Longden, I. and Bleasby, A. Trends in Genetics 16, (6) pp 276-277, http://emboss.bioinformatics.nl/). For protein sequences EBLOSUM62 is used for the substitution matrix. For nucleotide sequence, EDNAFULL is used. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms.

After alignment by the program NEEDLE as described above the percentage of sequence identity between a query sequence and a sequence of the invention is calculated as follows: Number of corresponding positions in the alignment showing an identical amino acid or identical nucleotide in both sequences divided by the total length of the alignment after subtraction of the total number of gaps in the alignment. The identity defined as herein can be obtained from NEEDLE by using the NOBRIEF option and is labeled in the output of the program as "longest-identity".

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., XBLAST and NBLAST) can be used. See the homepage of the National Center for Biotechnology Information at http://www.ncbi.nlm.nih.gov/.

In the context of the present invention a polypeptide having amylase activity preferably α-amylase activity may be a polypeptide encoded by a polynucleotide capable of hybridising to a polynucleotide according to SEQ ID NO: 1, 2, 5 or 6 or capable of hybridising to the complementary strand of a polynucleotide according to SEQ ID NO: 1, 2, 5 or 6, preferably it is capable of hybridising under low stringency conditions, more preferably it is capable of hybridising under medium stringency conditions, even more preferably it is capable of hybridising under high stringency conditions to the complementary strand of a polynucleotide according to SEQ ID NO: 1, 2, 5 or 6.

As used herein, the term "hybridizing" is intended to describe conditions for hybridization and washing under which polynucleotide sequences at least about 60%, 65%, 80%, 85%, 90%, preferably at least 93%, more preferably at least 95% and most preferably at least 98% identical to each other typically remain hybridized to the complement of each other. As used herein, the term "hybridization" means the pairing of substantially complementary strands of oligomeric compounds. One mechanism of pairing involves hydrogen bonding, which may be Watson-Crick, Hoogsteen or reversed Hoogsteen hydrogen bonding, between complementary nucleotide bases (nucleotides) of the strands of oligomeric compounds. For example, adenine and thymine are complementary nucleic acids which pair through the formation of hydrogen bonds. Hybridization can occur under varying circumstances. "Stringency hybridization" or "hybridizes under low stringency, medium stringency, high stringency, or very high stringency conditions" is used herein to describe conditions for hybridization and washing, more specifically conditions under which an oligomeric compound will hybridize to its target sequence, but to a minimal number of other sequences. So, the oligomeric compound will hybridize to the target sequence to a detectably greater degree than to other sequences. Guidance for performing hybridization reactions can be found in Current Protocols in Molecular Biology, John Wiley & Sons, N.Y. (1989), 6.3.1-6:3.6.

The skilled artisan will know which conditions to apply for low, medium and high stringency hybridisation conditions. Additional guidance regarding such conditions is readily available in the art, for example, in Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.).

Stringency conditions are sequence-dependent and will be different in different circumstances. Longer sequences hybridize specifically at higher temperatures. Generally, stringency conditions are selected to be about 5° C. lower than the thermal melting point ($T_m$) for the oligomeric compound at a defined ionic strength and pH. The $T_m$ is the temperature (under defined ionic strength and pH) at which 50% of an oligomeric compound hybridizes to a perfectly matched probe. Stringency conditions may also be achieved with the addition of destabilizing agents such as formamide.

Examples of specific hybridization conditions are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and 4) very high stringency hybridization conditions are 0.5M sodium phosphate, 7% SDS at 65° C., followed by one or more washes at 0.2×SSC, 1% SDS at 65° C.

Within the context of the present invention the mutant microbial host cell is deficient in the production of a polypeptide having amylase activity, preferably α-amylase activity as defined herein when the host cell comprises a modification, preferably in its genome, which results in a reduced or no production of the polypeptide having amylase activity, preferably α-amylase activity as defined herein if compared to the parent microbial host cell that has not been modified, when analysed under the same conditions and/or comprises a modification which results in a polypeptide derived from the polypeptide having amylase activity, preferably α-amylase activity as described herein with decreased or no (α)-amylase activity if compared to the parent microbial host cell that has not been modified, when analysed under the same conditions. Therefore a mutant microbial host cell as defined herein is deficient in the production of a polypeptide having amylase activity, preferably α-amylase activity as described herein when a) it produces less polypeptide having amylase activity, preferably α-amylase activity as defined herein or it produces no polypeptide having amylase activity, preferably α-amylase activity as defined herein if compared with the parent microbial host cell which has not been modified and measured under the same conditions; and/or b) it produces a polypeptide derived from the polypeptide having amylase activity, preferably α-amylase activity as defined herein with decreased or no (α-)amylase activity if compared to the parent microbial host cell that has not been modified, when analysed under the same conditions.

In one embodiment the mutant microbial host cell produces 1% less polypeptide having amylase activity, preferably α-amylase activity as defined herein if compared with the parent microbial host cell which has not been modified and measured under the same conditions, at least 5% less, at least 10% less, at least 20% less, at least 30% less, at least 40% less, at least 50% less, at least 60% less, at least 70% less, at least 80% less, at least 90% less, at least 91% less, at least 92% less, at least 93% less, at least 94% less at least 95% less, at least 96% less, at least 97% less, at least 98% less, at least 99% less, or at least 99.9% less. Preferably the mutant microbial host cell produces substantially no polypeptide having amylase activity, preferably α-amylase activity as described herein if compared with the parent microbial host cell which has not been modified and measured under the same conditions.

In one embodiment the mutant microbial host cell produces a polypeptide derived from the polypeptide having amylase activity, preferably α-amylase activity as defined herein with 1% less (α-)amylase activity, if compared with the parent microbial host cell which has not been modified and measured under the same conditions, at least 5% less activity, at least 10% less activity, at least 20% less activity, at least 30% less activity, at least 40% less activity, at least 50% less activity, at least 60% less activity, at least 70% less activity, at least 80% less activity, at least 90% less activity, at least 91% less activity, at least 92% less activity, at least 93% less activity, at least 94% less activity, at least 95% less activity, at least 96% less activity, at least 97% less activity, at least 98% less activity, at least 99% less activity, or at least 99.9% less activity. Preferably the mutant microbial host cell produces a polypeptide derived from a polypeptide having amylase activity, preferably α-amylase activity as described herein with substantially no (α-)amylase activity if compared with the parent microbial host cell which has not been modified and analysed under the same conditions.

Deficiency of a mutant microbial host cell according to the invention in the production of a polypeptide having amylase activity as defined herein may be measured by determining the amount and/or (specific) activity of polypeptide having amylase activity, preferably α-amylase activity as defined above produced by the mutated microbial host cell and/or it may be measured by determining the amount of mRNA transcribed from a polynucleotide encoding the polypeptide as described above and/or it may be measured by gene or genome sequencing if compared to the parent host cell which has not been modified.

A modification in the genome can be determined by comparing the DNA sequence of the mutant microbial host cell to the sequence of the parent (non-modified) microbial host cell. Sequencing of DNA and genome sequencing can be done using standard methods known to the person skilled in the art, for example using Sanger sequencing technology and/or next generation sequencing technologies such as Illumina GA2, Roche 454, etc. as reviewed in Elaine R. Mardis (2008), Next-Generation DNA Sequencing Methods, Annual Review of Genomics and Human Genetics, 9: 387-402. (doi:10.1146/annurev.genom 0.9.081307.164359)

Deficiency in the production of the polypeptide having amylase activity preferably α-amylase activity as described herein can be measured using any assay available to the skilled person, such as α-amylase activity measurement as described herein, transcriptional profiling, Northern blotting RT-PCR, Q-PCR and Western blotting. In particular quantifying the amount of mRNA present in a cell may for example be achieved by northern blotting (in Molecular Cloning: A Laboratory Manual, Sambrook et al., New York: Cold Spring Harbour Press, 1989). Quantifying the amount of polypeptide having amylase activity, preferably α-amylase activity described herein present in a cell may for example be achieved by western blotting. The difference in mRNA amount may also be quantified by DNA array analysis (Eisen, M. B. and Brown, P. O. DNA arrays for analysis of gene expression. Methods Enzymol. 1999:303: 179-205).

A modification, preferably in the genome, is construed as one or more modifications.

The modification, preferably in the genome, can either be effected by a) subjecting the parent microbial host cell to recombinant genetic manipulation techniques; and/or b) subjecting the parent microbial host cell to (classical) mutagenesis; and/or c) subjecting the parent microbial host cell to an inhibiting compound or composition.

Modification of a genome of a (mutant) microbial host cell is herein defined as any event resulting in a change in a polynucleotide sequence in the genome of the cell.

In a preferred embodiment the mutant microbial host cell according to the invention has a modification, preferably in its genome comprising:

a) a modification which results in a reduced or no production of a polypeptide as defined herein if compared to the parent microbial host cell that has not been modified, when analysed under the same conditions and/or b) modification which results in a polypeptide derived from a polypeptide as defined herein with decreased or no (enzymatic) activity as defined herein if compared to the parent microbial host cell that has not been modified, when analysed under the same conditions.

In a preferred embodiment the mutant microbial host cell according to the invention has a modification, preferably in its genome comprising:

a) a modification which results in a reduced or no production of a polypeptide having amylase activity, preferably α-amylase activity as defined herein if compared to the parent microbial host cell that has not been modified, when analysed under the same conditions and/or b) a modification which results in a polypeptide derived from a polypeptide having amylase activity, preferably α-amylase activity as defined herein with decreased or no (α-)amylase activity as defined herein if compared to the parent microbial host cell that has not been modified, when analysed under the same conditions.

Modification can be introduced by classical strain improvement, random mutagenesis followed by selection. Modification can also be introduced by site-directed mutagenesis.

Modification may be accomplished by the introduction (insertion), substitution (replacement) or removal (deletion) of one or more nucleotides in a polynucleotide sequence. A full or partial deletion of a polynucleotide coding for the polypeptide having amylase activity preferably α-amylase activity as defined herein may be achieved. In alternative a polynucleotide coding for the polypeptide as defined herein may be partially or fully replaced with a polynucleotide sequence which does not code for a polypeptide having amylase activity preferably α-amylase activity as defined herein or which code for a partially or fully inactive form of a polypeptide as defined herein. In yet another alternative one or more nucleotides can be inserted into the polynucleotide encoding a polypeptide having amylase activity, preferably α-amylase activity as defined herein resulting in the disruption of said polynucleotide and consequent partial or full inactivation of the polypeptide as defined herein coded by the disrupted polynucleotide.

In one embodiment the mutant microbial host cell according to the invention comprises a modification in its genome selected from a) a full or partial deletion of a polynucleotide as defined herein, b) a full or partial replacement of a polynucleotide as defined herein with a polynucleotide sequence which does not code for a polypeptide as defined herein or which code for a partially or fully inactive form of a polypeptide as defined herein c) a disruption of a polynucleotide as defined herein by the insertion of one or more nucleotides in the polynucleotide sequence and consequent partial or full inactivation of the polypeptide as defined herein coded by the disrupted polynucleotide.

This modification may for example be in a coding sequence or a regulatory element required for the transcription or translation of the polynucleotide as described above. For example, nucleotides may be inserted or removed so as to result in the introduction of a stop codon, the removal of a start codon or a change or a frame-shift of the open reading frame of a coding sequence. The modification of a coding sequence or a regulatory element thereof may be accomplished by site-directed or random mutagenesis, DNA shuffling methods, DNA reassembly methods, gene synthesis (see for example *Young and Dong*, (2004), *Nucleic Acids Research* 32, (7) electronic access http://nar.oupjournals.org/cgi/reprint/32/7/e59 or Gupta et al. (1968), *Proc. Natl. Acad. Sci USA*, 60: 1338-1344; Scarpulla et al. (1982), *Anal. Biochem.* 121: 356-365; Stemmer et al. (1995), *Gene* 164: 49-53), or PCR generated mutagenesis in accordance with methods known in the art. Examples of random mutagenesis procedures are well known in the art, such as for example chemical (NTG for example) mutagenesis or physical (UV for example) mutagenesis. Examples of site-directed mutagenesis procedures are the QuickChange™ site-directed mutagenesis kit (Stratagene Cloning Systems, La Jolla, Calif.), the 'The Altered Sites® II in vitro Mutagenesis Systems' (Promega Corporation) or by overlap extension using PCR as described in Gene. 1989 Apr. 15; 77(1):51-9. (Ho S N, Hunt H D, Horton R M, Pullen J K, Pease L R "Site-directed mutagenesis by overlap extension using the polymerase chain reaction") or using PCR as described in *Molecular Biology: Current Innovations and Future Trends*. (Eds. A. M. Griffin and H. G. Griffin. ISBN 1-898486-01-8; 1995 Horizon Scientific Press, PO Box 1, Wymondham, Norfolk, U.K.).

Preferred methods of modification are based on recombinant genetic manipulation techniques such as partial or complete gene replacement or partial or complete gene deletion.

For example, in case of replacement of a polynucleotide, nucleic acid construct or expression cassette, an appropriate DNA sequence may be introduced at the target locus to be replaced. The appropriate DNA sequence is preferably present on a cloning vector. Preferred integrative cloning vectors comprise a DNA fragment, which is homologous to the polynucleotide and/or has homology to the polynucleotides flanking the locus to be replaced for targeting the integration of the cloning vector to this pre-determined locus. In order to promote targeted integration, the cloning vector is preferably linearized prior to transformation of the cell. Preferably, linearization is performed such that at least one but preferably either end of the cloning vector is flanked by sequences homologous to the DNA sequence (or flanking sequences) to be replaced. This process is called homologous recombination and this technique may also be used in order to achieve (partial) gene deletion.

For example a polynucleotide corresponding to the endogenous polynucleotide may be replaced by a defective polynucleotide, that is a polynucleotide that fails to produce a (fully functional) polypeptide. By homologous recombination, the defective polynucleotide replaces the endogenous polynucleotide. It may be desirable that the defective polynucleotide also encodes a marker, which may be used for selection of transformants in which the nucleic acid sequence has been modified.

Alternatively or in combination with other mentioned techniques, a technique based on in vivo recombination of cosmids in *E. coli* can be used, as described in: *A rapid method for efficient gene replacement in the filamentous fungus Aspergillus nidulans* (2000) Chaveroche, M-K., Ghico, J-M. and d'Enfert C; *Nucleic acids Research, vol* 28, no 22.

Alternatively, modification, wherein said host cell produces less of or no protein such as the polypeptide having amylase activity, preferably α-amylase activity as described herein and encoded by a polynucleotide as described herein, may be performed by established anti-sense techniques using a nucleotide sequence complementary to the nucleic acid sequence of the polynucleotide. More specifically, expression of the polynucleotide by a host cell may be reduced or eliminated by introducing a nucleotide sequence complementary to the nucleic acid sequence of the polynucleotide, which may be transcribed in the cell and is capable of hybridizing to the mRNA produced in the cell. Under conditions allowing the complementary anti-sense nucleotide sequence to hybridize to the mRNA, the amount of protein translated is thus reduced or eliminated. An example of expressing an antisense-RNA is shown in Appl. Environ. Microbiol. 2000 February; 66(2):775-82. (*Characterization of a foldase, protein disulfide isomerase A, in the protein secretory pathway of Aspergillus niger*. Ngiam C, Jeenes D J, Punt P J, Van Den Hondel C A, Archer D B) or (Zrenner R, Willmitzer L, Sonnewald U. *Analysis of the expression of potato uridinediphosphate-glucose pyrophosphorylase and its inhibition by antisense RNA. Planta.* (1993); 190(2):247-52).

In one embodiment the mutant microbial host cell according to the invention is a mutant microbial host cell wherein the modification which results in a reduced or no production of a polypeptide as defined herein is due to a reduced production of the mRNA encoding said polypeptide if compared with a parent microbial host cell which has not been modified and measured under the same conditions.

A modification which results in a reduced amount of the mRNA transcribed from the polynucleotide encoding for the polypeptide having amylase activity, preferably α-amylase activity as described above may be obtained via the RNA interference (RNAi) technique (FEMS Microb. Lett. 237 (2004): 317-324). In this method identical sense and anti-sense parts of the nucleotide sequence, which expression is to be affected, are cloned behind each other with a nucleotide spacer in between, and inserted into an expression vector. After such a molecule is transcribed, formation of small nucleotide fragments will lead to a targeted degradation of the mRNA, which is to be affected. The elimination of the specific mRNA can be to various extents. The RNA interference techniques described in WO2008/053019, WO2005/05672A1, WO2005/026356A1, Oliveira et al., "*Efficient cloning system for construction of gene silencing vectors in Aspergillus niger*" (2008) *Appl. Microbiol. and Biotechnol.* 80 (5): 917-924 and/or Barnes et al., "siRNA as a molecular tool for use in *Aspergillus niger*" (2008) *Biotechnology Letters* 30 (5): 885-890 may be used at this purpose.

A modification which results in a polypeptide with decreased or no amylase activity preferably with decreased or no α-amylase activity as defined herein can be obtained by different methods, for example by an antibody directed against such a polypeptide or a chemical inhibitor or a protein inhibitor or a physical inhibitor (Tour O. et al, (2003) Nat. Biotech: Genetically targeted chromophore-assisted light inactivation. Vol. 21. no. 12:1505-1508) or peptide inhibitor or an anti-sense molecule or RNAi molecule (R. S. Kamath_et al, (2003) Nature: Systematic functional analysis of the *Caenorhabditis elegans* genome using RNAi. vol. 421, 231-237).

In addition of the above-mentioned techniques or as an alternative, it is also possible to inhibiting the activity of a polypeptide as defined herein, or to re-localize the polypeptide as defined herein by means of alternative signal sequences (Ramon de Lucas, J., Martinez O, Perez P., Isabel Lopez, M., Valenciano, S. and Laborda, F. The *Aspergillus nidulans* carnitine carrier encoded by the acuH gene is exclusively located in the mitochondria. FEMS Microbiol Lett. 2001 Jul. 24; 201(2):193-8) or retention signals (Derkx, P. M. and Madrid, S. M. The foldase CYPB is a component of the secretory pathway of *Aspergillus niger* and contains the endoplasmic reticulum retention signal HEEL. Mol. Genet. Genomics. 2001 December; 266(4): 537-545), or by targeting the polypeptide to a peroxisome which is capable of fusing with a membrane-structure of the cell involved in the secretory pathway of the cell, leading to secretion outside the cell of the polypeptide (e.g. as described in WO2006/040340).

Alternatively or in combination with above-mentioned techniques, inhibition of polypeptide having amylase activity preferably α-amylase activity as defined herein can also be obtained, e.g. by UV or chemical mutagenesis (Mattern, I. E., van Noort J. M., van den Berg, P., Archer, D. B., Roberts, I. N. and van den Hondel, C. A., Isolation and characterization of mutants of *Aspergillus niger* deficient in extracellular proteases. Mol Gen Genet. 1992 August; 234 (2):332-6) or by the use of inhibitors inhibiting enzymatic activity of a polypeptide as described herein (e.g. nojirimycin, which function as inhibitor for β-glucosidases (Carrel F. L. Y. and Canevascini G. *Canadian Journal of Microbiology* (1991) 37(6): 459-464; Reese E. T., Parrish F. W. and Ettlinger M. *Carbohydrate Research* (1971) 381-388)).

In an embodiment according to the invention the modification in the genome of the mutant microbial host cell according to the invention is a modification in at least one position of a polynucleotide as defined above encoding for the polypeptide having amylase activity, preferably α-amylase activity as defined above.

In the context of the present invention the "parent microbial host cell" and the "mutant microbial host cell" may be any type of host cell. The specific embodiments of the mutant microbial host cell are hereafter described. It will be clear to those skilled in the art that embodiments applicable to the mutant microbial host cell are as well applicable to the parent microbial host cell unless otherwise indicated.

The mutant microbial host cell according to the present invention may be a prokaryotic cell. Preferably, the prokaryotic host cell is bacterial cell. The term "bacterial cell" includes both Gram-negative and Gram-positive microorganisms. Suitable bacteria may be selected from e.g. *Escherichia, Anabaena, Caulobactert, Gluconobacter, Rhodobacter, Pseudomonas, Paracoccus, Bacillus, Brevibacterium, Corynebacterium, Rhizobium (Sinorhizobium), Flavobacterium, Klebsiella, Enterobacter, Lactobacillus, Lactococcus, Methylobacterium, Staphylococcus* or *Streptomyces*. Preferably, the bacterial cell is selected from the group consisting of *B. subtilis, B. amyloliquefaciens, B. licheniformis, B. puntis, B. megaterium, B. halodurans, B. pumilus, G. oxydans, Caulobactert crescentus* CB 15, *Methylobacterium extorquens, Rhodobacter sphaeroides, Pseudomonas zeaxanthinifaciens, Paracoccus denitrificans, E. coli, C. glutamicum, Staphylococcus carnosus, Streptomyces lividans, Sinorhizobium melioti* and *Rhizobium radiobacter*.

According to an embodiment, the mutant microbial host cell according to the invention is a eukaryotic host cell. Preferably, the eukaryotic cell is a mammalian, insect, plant, fungal, or algal cell. Preferred mammalian cells include e.g. Chinese hamster ovary (CHO) cells, COS cells, 293 cells, PerC6 cells, and hybridomas. Preferred insect cells include e.g. Sf9 and Sf21 cells and derivatives thereof. More preferably, the eukaryotic cell is a fungal cell, i.e. a yeast cell, such as *Candida, Hansenula, Kluyveromyces, Pichia, Sac-* charomyces, Schizosaccharomyces, or Yarrowia strain. More preferably from Kluyveromyces lactis, S. cerevisiae, Hansenula polymorpha, Yarrowia lipolytica and Pichia pastoris, or a filamentous fungal cell. Most preferably, the eukaryotic cell is a filamentous fungal cell.

Filamentous fungi include all filamentous forms of the subdivision Eumycota and Oomycota (as defined by Hawksworth et al., In, Ainsworth and Bisby's Dictionary of The Fungi, 8th edition, 1995, CAB International, University Press, Cambridge, UK). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. Filamentous fungal strains include, but are not limited to, strains of Acremonium, Agaricus, Aspergillus, Aureobasidium, Chrysosporium, Coprinus, Cryptococcus, Filibasidium, Fusarium, Humicola, Magnaporthe, Mucor, Myceliophthora, Neocallimastix, Neurospora, Paecilomyces, Penicillium, Piromyces, Panerochaete, Pleurotus, Schizophyllum, Talaromyces, Rasamsonia, Thermoascus, Thielavia, Tolypocladium, and Trichoderma.

Preferred filamentous fungal cells belong to a species of an Acremonium, Aspergillus, Chrysosporium, Myceliophthora, Penicillium, Talaromyces, Rasamsonia, Thielavia, Fusarium or Trichoderma genus, and most preferably a species of Aspergillus niger, Acremonium alabamense, Aspergillus awamori, Aspergillus foetidus, Aspergillus sojae, Aspergillus fumigatus, Talaromyces emersonii, Rasamsonia emersonii, Aspergillus oryzae, Chrysosporium lucknowense, Fusarium oxysporum, Myceliophthora thermophila, Trichoderma reesei, Thielavia terrestris or Penicillium chrysogenum. A more preferred host cell belongs to the genus Aspergillus, more preferably the host cell belongs to the species Aspergillus niger. When the host cell according to the invention is an Aspergillus niger host cell, the host cell preferably is CBS 513.88, CBS124.903 or a derivative thereof.

Several strains of filamentous fungi are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), Agricultural Research Service Patent Culture Collection, Northern Regional Research Center (NRRL), and All-Russian Collection of Microorganisms of Russian Academy of Sciences, (abbreviation in Russian—VKM, abbreviation in English—RCM), Moscow, Russia. Useful strains in the context of the present invention may be Aspergillus niger CBS 513.88, CBS124.903, Aspergillus oryzae ATCC 20423, IFO 4177, ATCC 1011, CBS205.89, ATCC 9576, ATCC14488-14491, ATCC 11601, ATCC12892, P. chrysogenum CBS 455.95, P. chrysogenum Wisconsin54-1255 (ATCC28089), Penicillium citrinum ATCC 38065, Penicillium chrysogenum P2, Thielavia terrestris NRRL8126, Talaromyces emersonii CBS 124.902, Acremonium chrysogenum ATCC 36225 or ATCC 48272, Trichoderma reesei ATCC 26921 or ATCC 56765 or ATCC 26921, Aspergillus sojae ATCC11906, Myceliophthora thermophila C1, Garg 27K, VKM-F 3500 D, Chrysosporium lucknowense C1, Garg 27K, VKM-F 3500 D, ATCC44006 and derivatives thereof.

According to one embodiment of the invention, when the mutant microbial host cell according to the invention is a filamentous fungal host cell the mutant microbial host cell may further comprise one or more modifications in its genome such that the mutant microbial host cell is deficient in the production of at least one product selected from glucoamylase (glaA), acid stable alpha-amylase (amyA), neutral alpha-amylase (amyBI and amyBII), oxalic acid hydrolase (oahA), a toxin, preferably ochratoxin and/or fumonisin, a protease transcriptional regulator prtT, PepA, a product encoded by the gene hdfA and/or hdfB, a non-ribosomal peptide synthase npsE if compared to a parent host cell and measured under the same conditions.

Oxalic acid hydrolase (oahA) is a component of the synthesis pathway of oxalic acid in many host cells. A host cell deficient in oahA will be deficient in oxalic acid. Oxalic acid is an unwanted by-product in many applications such as food-applications. Furthermore, oxalic acid lowers the pH of the medium cultivations of host cell producing this component, resulting in lowered yields; i.e. yield is increased in oxalic acid deficient host cells. It is therefore advantageous if the microbial host cell according to the invention is deficient in oahA. OahA deficient host cells and preferred methods of producing said host cells are extensively described in WO 2000/50576 and WO2004/070022. A preferred method to produce an oahA deficient host cell is the recombinant method of disruption described in WO 2000/50576. Preferably, the mutant microbial host cell according to the invention is deficient in oahA. Preferably, the oahA is a fungal oahA. More preferably, the oahA is the oahA from Aspergillus. Even more preferably the oahA is the oahA from Aspergillus niger. Even more preferably the oahA is the oahA from Aspergillus niger CBS 513.88. Most preferably, the oahA comprises the sequence of An10g00820.

prtT is a transcriptional activator of proteases in eukaryotic cells. Several fungal transcriptional activators of proteases have been recently described in WO 00/20596, WO 01/68864, WO 2006/040312 and WO 2007/062936. These transcriptional activators were isolated from Aspergillus niger (A. niger), Aspergillus fumigatus (A. fumigatus), Penicillium chrysogenum (P. chrysogenum) and Aspergillus oryzae (A. oryzae). These transcriptional activators of protease genes can be used to improve a method for producing a polypeptide in a fungal cell, wherein the polypeptide is sensitive for protease degradation. When the microbial host cell according to the invention is deficient in prtT, the host cell will produce less proteases that are under transcriptional control of prtT. It is therefore advantageous when the host cell according to the invention is deficient in prtT. prtT deficient hosts and preferred methods to produce these hosts are extensively described in WO 01/68864, WO 2006/040312. WO 01/68864 and WO 2006/040312 describe recombinant and classic methods to disrupt the prtT coding sequence. WO 2007/062936 describes disruption of the prtT binding site in a protease promoter. Disruption of the binding site impedes binding of prtT to the binding site. Consequently, the transcription of the protease is not activated by prtT and less protease is produced.

Preferably, the mutant microbial host cell according to the invention comprises a polynucleotide encoding prtT, said polynucleotide comprising a modification, wherein the host cell is deficient in the production of prtT compared to a parent cell it originates from when cultivated under comparable conditions. Preferably, the prtT is a fungal prtT. More preferably, the prtT is the prtT from Aspergillus. Even more preferably the prtT is the prtT from Aspergillus niger. Even more preferably the prtT is the prtT from Aspergillus niger CBS 513.88. Most preferably, the prtT comprises the sequence of An04g06940.

The term "glucoamylase" (glaA) is identical to the term "amyloglucosidase" and is defined herein as an enzyme having dextrin 6-alpha-D-glucanohydrolase activity which catalyses the endo hydrolysis of 1,6-alpha-D-glucoside linkages at points of branching in chains of 1,4-linked alpha-D-glucose residues and terminal 1,4-linked alpha-D-glucose residues. Glucoamylase activity can be measured as AGIU/ml by determining the liberation of paranitrofenol from the substrate p-nitrophenyl-a-D-glucopyranoside (Sigma). This results in a yellow colour, whose absorbance can be measured at 405 nm using a spectrophotometer. 1 AGIU is the quantity of enzyme, which produces 1 µmole of glucose per minute at pH 4.3 and 60° C. from a soluble starch substrate. In WO98/46772 additional details of the assay can be found.

Preferably, the mutant microbial host cell according to the invention comprises a polynucleotide encoding glaA, said polynucleotide comprising a modification, wherein the host cell is deficient in the production of glaA compared to a parent cell it originates from when cultivated under comparable conditions. Preferably, the glaA is a fungal glaA. More preferably, the glaA is the glaA from *Aspergillus*. Even more preferably the glaA is the glaA from *Aspergillus niger*. Even more preferably the glaA is the glaA from *Aspergillus niger* CBS 513.88. Most preferably, the glaA comprises the sequence of An03g06550.

The term "alpha-amylase" is defined herein as 1, 4-alpha-D-glucan glucanohydrolase activity which catalyzes the endohydrolysis of polysaccharides with three or more alpha-1, 4-linked glucose units in the presence of water to maltooligosaccharides. To determine the (neutral) alpha-amylase activity, the Megazyme cereal alpha-amylase kit is used (Megazyme, CERALPHA alpha amylase assay kit, catalogus. ref. K-CERA, year 2000-2001), according a protocol of the supplier. The measured activity is based on hydrolysis of non-reducing-endblocked ρ-nitrophenyl maltoheptaoside in the presence of excess glucoamylase and α-glucosidase at a pH of 7.0. The amount of formed ρ-nitrophenol is a measure for alpha-amylase activity present in a sample.

The term "acid stable alpha-amylase" (amyA) is defined herein as an enzyme having alpha-amylase activity with optimal activity in the acid pH range. To determine the acid stable alpha-amylase activity, also the Megazyme cereal alpha-amylase kit is used (Megazyme, CERALPHA alpha amylase assay kit, catalogus. ref. K-CERA, year 2000-2001), according a protocol of the supplier but at an acid pH. The measured activity is based on hydrolysis of non-reducing-endblocked ρ-nitrophenyl maltoheptaoside in the presence of excess glucoamylase and α-glucosidase at a pH of 4.5. The amount of formed ρ-nitrophenol is a measure for acid stable alpha-amylase activity present in a sample.

Preferably, the host cell according to the invention comprises a polynucleotide encoding AmyA, said polynucleotide comprising a modification, wherein the host cell is deficient in amyA compared to the parent cell it originates from when cultivated under comparable conditions. Preferably, the amyA is a fungal amyA. More preferably, the amyA is the amyA from *Aspergillus*. Even more preferably the amyA is the amyA from *Aspergillus niger*. Even more preferably the amyA is the amyA from *Aspergillus niger* CBS 513.88. Most preferably, the amyA comprises the sequence of An11g03340.

The term "neutral alpha-amylase activity" (amy) is defined herein as an enzyme having alpha-amylase activity with optimal activity in the neutral pH range.

Preferably, the host cell according to the invention comprises a polynucleotide encoding AmyB, said polynucleotide comprising a modification, wherein the host cell is deficient in amyBI and/or amyBII compared to the parent cell it originates from when cultivated under comparable conditions. More preferably, the microbiaol host cell according to the invention is deficient in amyBI and amy BII. Preferably, the amyB a is a fungal amyB. More preferably, the amyB is the amyB from *Aspergillus*. Even more preferably the amyB is the amyBI from *Aspergillus niger*. Even more preferably the amyB is the amyBI from *Aspergillus niger* CBS 513.88. Most preferably, the amyBI comprises the sequence of An12g06930. Even more preferably the amyB is the amyBII from *Aspergillus niger*. Even more preferably the amyB is the amyBII from *Aspergillus niger* CBS 513.88. Most preferably, the amyBII comprises the sequence of An05g02100.

The term toxin associated polynucleotide is defined herein as a gene cluster, a multitude of genes, a gene or part thereof encoding a compound, or biochemical pathway responsible for the biosynthesis or secretion of at least one toxin or toxin intermediate compound. Said compound may e.g. be a polypeptide, which may be an enzyme.

A number of host cells, especially fungi, which are used as host cells in the production of polypeptides of interest possesses genes encoding enzymes involved in the biosynthesis of various toxins. For example, cyclopiazonic acid, kojic acid, 3-nitropropionic acid and aflatoxins are known toxins, which are formed in, e.g., *Aspergillus flavus*. Similarly, trichothecenes are formed in a number of fungi, e.g., in *Fusarium* sp. such as *Fusarium venenatum* and in *Trichoderma* and ochratoxin may be produced by *Aspergillus*. Recently, sequencing of the genome of an industrial *Aspergillus niger* host strain revealed a fumonisin gene cluster (Pel et al., "Genome sequencing and analysis of the versatile cell factory *Aspergillus niger* CBS 513.88". Nat Biotechnol. 2007 February; 25 (2):221-231). The formation of such toxins during the fermentation of compounds of interest is highly undesirable as these toxins may present a health hazard to operators, customers and the environment. Consequently, a toxin deficient host cell enables toxin-free production of a compound of interest. The toxin-free compound is easier to produce since no toxin has to be removed from the product. Furthermore, the regulatory approval procedure for the compound is easier.

Preferably, the mutant microbial host cell according to the invention comprises a toxin associated polynucleotide encoding a compound (which may e.g. be a polypeptide which may be an enzyme) or biochemical pathway, said toxin associated polynucleotide comprising a modification, wherein the host cell is deficient in the production of said toxin or a toxin intermediate compound compared to the parent cell it originates from when cultivated under comparable conditions. Preferably, the toxin or toxin intermediate compound is a fungal toxin or toxin intermediate compound. More preferably, the toxin or toxin intermediate compound is a toxin or toxin intermediate compound from *Aspergillus*. Even more preferably the toxin or the toxin intermediate compound is a toxin or toxin intermediate compound from *Aspergillus niger*. Even more preferably the toxin or toxin intermediate compound is a toxin or toxin intermediate compound from *Aspergillus niger* CBS 513.88. Even more preferably, the toxin or the toxin intermediate compound is fumonisin or a fumonisin intermediate compound. Even more preferably, the toxin or the toxin intermediate compound is ochratoxin or an ochratoxin intermediate compound. Most preferably, the toxin or the toxin intermediate compound is ochratoxin or fumonisin or an ochratoxin or a fumonisin intermediate compound.

Preferably, the toxin associated polynucleotide encodes a compound (which may e.g. be a polypeptide which may be an enzyme) or a biochemical pathway which is involved in the production of a fungal toxin or toxin intermediate compound. More preferably, a toxin or toxin intermediate compound from *Aspergillus*. Even more preferably, a toxin or toxin intermediate compound from *Aspergillus niger*. Even more preferably, a toxin or toxin intermediate compound from *Aspergillus niger* CBS 513.88. Even more preferably, a fumonisin or a fumonisin intermediate compound. Even more preferably, a fumonisin-B or a fumonisin-B intermediate compound. Even more preferably, a fumonisin-B2 or a fumonisin-B2 intermediate compound. Even more preferably, the toxin associated polynucleotide comprises the sequence of the fumonisin cluster from An01g06820 until An01g06930. Most preferably, the toxin associated polynucleotide comprises the sequence of An01g06930.

In another preferred embodiment, the toxin associated polynucleotide encodes a compound (which may e.g. be a polypeptide which may be an enzyme) or a biochemical pathway which is involved in ochratoxin or an ochratoxin intermediate compound. More preferably, an ochratoxin A or an ochratoxin A intermediate compound. More preferably, the toxin associated polynucleotide comprises the sequence of the cluster from An15g07880 until An15g07930. Most preferably, the toxin associated polynucleotide comprises the sequence of An15g07910 and/or the sequence of An15g07920.

Preferably, the mutant microbial host cell according to the invention comprises at least one toxin associated polynucleotide encoding a compound (which may e.g. be a polypeptide which may be an enzyme) or biochemical pathway, said toxin associated polynucleotide comprising at least one modification, wherein the host cell is deficient in the production of a toxin or, toxin intermediate compound compared to the parent cell it originates from when cultivated under comparable conditions.

More preferably, the host cell according to the invention comprises two toxin associated polynucleotides, said two toxin associated polynucleotides each comprising at least one modification, wherein the host cell is preferably deficient in the production of fumonisin and ochratoxin compared to the parent cell it originates from when cultivated under comparable conditions.

Even more preferably, the mutant microbial host cell according to the invention comprises three or more toxin associated polynucleotides said three or more toxin associated polynucleotides each comprising at least one modification, wherein the host cell is preferably deficient in the production of fumonisin, ochratoxin and at least one additional toxin or toxin intermediate compound compared to the parent cell it originates from when cultivated under comparable conditions.

Therefore, when the mutant microbial host cell according to the invention is a filamentous fungal host cell the host cell may comprise one or more modifications in its genome to result in a deficiency in the production of the major extracellular aspartic protease PepA. For example the host cell according to the invention may further comprise a disruption of the pepA gene encoding the major extracellular aspartic protease PepA. More preferably, the pepA is the pepA from *Aspergillus*. Even more preferably the pepA is the pepA from *Aspergillus niger*. Even more preferably the pepA is the pepA from *Aspergillus niger* CBS 513.88. Most preferably, the pepA comprises the sequence of An14g04710. Preferably, the efficiency of targeted integration of a polynucleotide to a pre-determined site into the genome of the mutant microbial host cell according to the invention is increased by making the cell deficient in a component in NHR (non-homologous recombination). Preferably, the mutant microbial host cell according to the invention comprises a polynucleotide encoding an NHR component comprising a modification, wherein said host cell is deficient in the production of said NHR component compared to a parent cell it originates from when cultivated under the same conditions.

The NHR component to be modified can be any NHR component known to the person skilled in the art. Preferred NHR components to be modified are selected from the group of filamentous fungal homologues of yeast KU70, KU80, MRE11, RAD50, RAD51, RAD52, XRS2, SIR4, LIG4. More preferred NHR components to be modified are filamentous fungal homologues of yeast KU70 and KU80, preferably hdfA (homologue of yeast KU70) or homologues thereof and hdfB (homologue of yeast KU80) or homologues thereof. The most preferred NHR component to be modified is KU70 or hdfA, or a homologue thereof. Another preferred NHR component to be modified is KU80 or hdfB, or a homologue thereof. Methods to obtain such host cell deficient in a component involved in NHR are known to the skilled person and are extensively described in WO2005/095624. Preferably the hdfA gene is the hdfA gene from *A. niger*, more preferably the hdfA from *A. niger* according to SEQ ID NO: 1 of WO2005/095624. In another preferred embodiment the hdfB gene is the hdfB gene from *A. niger*, more preferably the hdfB from *A. niger* according to SEQ ID NO: 4 of WO2005/095624.

Therefore when the mutant microbial host cell according to the invention is a filamentous fungal host cell the host cell according to the invention may additionally comprises one or more modifications in its genome to result in a deficiency in the production of the product encoded by the hdfA gene (as depicted in SEQ ID NO: 3 of WO 2005/095624) and/or hdfB gene (as depicted in SEQ ID NO: 6 of WO 2005/095624). For example the host cell according to the invention may further comprise a disruption of the hdfA and/or hdfB gene. Filamentous fungal host cells which are deficient in a product encoded by the hdfA and/or hdfB gene have been described in WO 2005/095624.

When the mutant microbial host cell according to the invention is a filamentous fungal host cell the host cell according to the invention may additionally comprise a modification in its genome which results in the deficiency in the production of the non-ribosomal peptide synthase npsE. Such host cells deficient in the production of non-ribosomal peptide synthase npsE have been described in WO2012/001169 (npsE has a genomic sequence as depicted in SEQ ID NO: 35, a coding sequence depicted in SEQ ID NO: 36, the mRNA depicted in SEQ ID NO: 37 and the nrps protein depicted in SEQ ID NO: 38 of WO2012/001169).

The mutant microbial host cell according to the invention may additionally comprises a modification in its genome which results in the deficiency in the production of the protein product of the agsE gene. Such host cells deficient in this protein product have been described in a co-pending International patent application filed on 19 Jul. 2013 entitled "AgsE-deficient strain" and which claims priority from EP12177172.9 filed on 19 Jul. 2012 and U.S. 61/673596 filed on 19 Jul. 2012. agsE has a genomic sequence as depicted in SEQ ID NO: 1 and a coding sequence depicted in SEQ ID NO: 2 and the AgsE protein as depicted in SEQ ID NO: 3 with the mature AgsE protein shown in SEQ ID NO: 4 of this co-pending International patent application. SEQ ID NOs: 1, 2, 3 and 4 correspond to SEQ ID NOs: 17, 18, 19 and 20 herein respectively.

The deficiency in the production of at least one product selected from glucoamylase (glaA), acid stable alpha-amylase (amyA), neutral alpha-amylase (amyBI and amyBII), oxalic acid hydrolase (oahA), a toxin, preferably ochratoxin and/or fumonisin, a protease transcriptional regulator prtT, PepA, a product encoded by the gene hdfA and/or hdfB, a non-ribosomal peptide synthase npsE, a protein product encoded by AgsE if compared to a parent host cell and measured under the same conditions may already be present in the parent host cell from which the mutant microbial host cell according to the invention is derived.

In one embodiment the mutant microbial cell according to the invention further comprises a deficiency in the production of glaA and optionally at least another product selected from the group consisting of acid stable alpha-amylase (amyA), neutral alpha-amylase (amyBI and amyBII), oxalic acid hydrolase (oahA), a toxin, preferably ochratoxin and/or fumonisin, a protease transcriptional regulator prtT, PepA, a product encoded by the gene hdfA and/or hdfB, a non-ribosomal peptide synthase npsE, a protein product encoded by AgsE if compared to a parent host cell and measured under the same conditions.

In one embodiment the mutant microbial cell according to the invention further comprises a deficiency in the production of glaA, PepA and optionally at least another product selected from the group consisting of acid stable alpha-amylase (amyA), neutral alpha-amylase (amyBI and amyBII), oxalic acid hydrolase (oahA), a toxin, preferably ochratoxin and/or fumonisin, a protease transcriptional regulator prtT, a product encoded by the gene hdfA and/or hdfB, a non-ribosomal peptide synthase npsE, a protein product encoded by AgsE if compared to a parent host cell and measured under the same conditions.

In one embodiment the mutant microbial cell according to the invention further comprises a deficiency in the production of glaA, PepA, acid stable alpha-amylase (amyA) and optionally at least another product selected from the group consisting of neutral alpha-amylase (amyBI and amyBII), oxalic acid hydrolase (oahA), a toxin, preferably ochratoxin and/or fumonisin, a protease transcriptional regulator prtT, a product encoded by the gene hdfA and/or hdfB, a non-ribosomal peptide synthase npsE, a protein product encoded by AgsE if compared to a parent host cell and measured under the same conditions.

In one embodiment the mutant microbial cell according to the invention further comprises a deficiency in the production of glaA, PepA, acid stable alpha-amylase (amyA), neutral alpha-amylase amyBI and optionally at least another product selected from the group consisting of neutral alpha-amylase amyBII, oxalic acid hydrolase (oahA), a toxin, preferably ochratoxin and/or fumonisin, a protease transcriptional regulator prtT, a product encoded by the gene hdfA and/or hdfB, a non-ribosomal peptide synthase npsE, a protein product encoded by AgsE if compared to a parent host cell and measured under the same conditions.

In one embodiment the mutant microbial cell according to the invention further comprises a deficiency in the production of glaA, PepA, acid stable alpha-amylase (amyA), neutral alpha-amylase amyBI and amyBII, and optionally at least another product selected from the group consisting of oxalic acid hydrolase (oahA), a toxin, preferably ochratoxin and/or fumonisin, a protease transcriptional regulator prtT, a product encoded by the gene hdfA and/or hdfB, a non-ribosomal peptide synthase npsE, a protein product encoded by AgsE if compared to a parent host cell and measured under the same conditions.

In one embodiment the mutant microbial cell according to the invention further comprises a deficiency in the production of glaA, PepA, acid stable alpha-amylase (amyA), neutral alpha-amylase amyBI and amyBII, a product encoded by the gene hdfA and optionally at least another product selected from the group consisting of oxalic acid hydrolase (oahA), a toxin, preferably ochratoxin and/or fumonisin, a protease transcriptional regulator prtT, a product encoded by the gene hdfB, a non-ribosomal peptide synthase npsE, a protein product encoded by AgsE if compared to a parent host cell and measured under the same conditions.

In one embodiment the mutant microbial cell according to the invention further comprises a deficiency in the production of glaA, PepA, acid stable alpha-amylase (amyA), neutral alpha-amylase amyBI and amyBII, a product encoded by the gene hdfA, oxalic acid hydrolase (oahA) and optionally at least another product selected from the group consisting of, a toxin, preferably ochratoxin and/or fumonisin, a protease transcriptional regulator prtT, a product encoded by the gene hdfB, a non-ribosomal peptide synthase npsE, a protein product encoded by AgsE if compared to a parent host cell and measured under the same conditions.

In one embodiment the mutant microbial cell according to the invention further comprises a deficiency in the production of glaA, PepA, acid stable alpha-amylase (amyA), neutral alpha-amylase amyBI and amyBII, a product encoded by the gene hdfA, oxalic acid hydrolase (oahA), ochratoxin, fumonisin, and optionally at least another product selected from the group consisting of a protease transcriptional regulator prtT, a product encoded by the gene hdfB, a non-ribosomal peptide synthase npsE, a protein product encoded by AgsE if compared to a parent host cell and measured under the same conditions.

In one embodiment the mutant microbial cell according to the invention further comprises a deficiency in the production of glaA, PepA, acid stable alpha-amylase (amyA), neutral alpha-amylase amyBI and amyBII, a product encoded by the gene hdfA, oxalic acid hydrolase (oahA), ochratoxin, fumonisin, a protease transcriptional regulator prtT and optionally at least another product selected from the group consisting of a product encoded by the gene hdfB, a non-ribosomal peptide synthase npsE, a protein product encoded by AgsE if compared to a parent host cell and measured under the same conditions.

In one embodiment the mutant microbial cell according to the invention further comprises a deficiency in the production of glaA, PepA, acid stable alpha-amylase (amyA), neutral alpha-amylase amyBI and amyBII, a product encoded by the gene hdfA, oxalic acid hydrolase (oahA), ochratoxin, fumonisin, a protease transcriptional regulator prtT, a non-ribosomal peptide synthase npsE and optionally at least another product selected from the group consisting of a product encoded by the gene hdfB, a protein product encoded by AgsE if compared to a parent host cell and measured under the same conditions.

In one embodiment the mutant microbial cell according to the invention further comprises a deficiency in the production of glaA, PepA, acid stable alpha-amylase (amyA), neutral alpha-amylase amyBI and amyBII, a product encoded by the gene hdfA, oxalic acid hydrolase (oahA), ochratoxin, fumonisin, a protease transcriptional regulator prtT, a protein product encoded by AgsE and optionally at least another product selected from the group consisting of a product encoded by the gene hdfB, a non-ribosomal peptide synthase npsE, if compared to a parent host cell and measured under the same conditions.

In a more preferred embodiment the mutant microbial cell according to the invention further has a reduced amylase background and comprises a deficiency in the production of glaA, acid stable alpha-amylase (amyA), neutral alphaamylase amyBI and amyBII, if compared to a parent host cell and measured under the same conditions. Such a microbial mutant cell may also comprise a deficiency in the production of a filamentous fungal homolog of KU70 or KU80. Such a microbial mutant cell may also comprise a deficiency in the production of a toxin. Such a microbial mutant cell may also comprise a deficiency in the production of a filamentous fungal homolog of KU70 or KU80 and a deficiency in the production of a toxin.

In an even more preferred embodiment the mutant microbial cell according to the invention has a reduced amylase background and further comprises a deficiency in the production of glaA, acid stable alpha-amylase (amyA), neutral alpha-amylase amyBI, amyBII and a protein product encoded by AgsE if compared to a parent host cell and measured under the same conditions. Such a microbial mutant cell may also comprise a filamentous fungal homolog of KU70 or KU80. Such a microbial mutant cell may also comprise a deficiency in the production of a toxin. Such a microbial mutant cell may also comprise a deficiency in the production of a filamentous fungal homolog of KU70 or KU80 and a deficiency in the production of a toxin.

In a most preferred embodiment the mutant microbial cell according to the invention further has a reduced alpha-amylase background and comprises a deficiency in the production acid stable alpha-amylase (amyA), neutral alpha-amylase amyBI and amyBII, if compared to a parent host cell and measured under the same conditions. Such a microbial mutant cell may also comprise a filamentous fungal homolog of KU70 or KU80. Such a microbial mutant cell may also comprise a deficiency in the production of a toxin. Such a microbial mutant cell may also comprise a deficiency in the production of a filamentous fungal homolog of KU70 or KU80 and a deficiency in the production of a toxin.

When the mutant microbial host cell according to the invention is a filamentous fungal host cell the host cell may additionally comprise at least two substantially homologous DNA domains suitable for integration of one or more copies of a polynucleotide encoding a compound of interest wherein at least one of the at least two substantially homologous DNA domains is adapted to have enhanced integration preference for the polynucleotide encoding a compound of interest compared to the substantially homologous DNA domain it originates from, and wherein the substantially homologous DNA domain where the adapted substantially homologous DNA domain originates from has a gene conversion frequency that is at least 10% higher than one of the other of the at least two substantially homologous DNA domains. These cells have been described in WO2011/009700. Strains containing two or more copies of these substantially homologous DNA domains are also referred hereafter as strain containing two or more amplicons. Examples of host cells comprising such amplicons are e.g. described in van Dijck et al, 2003, Regulatory Toxicology and Pharmacology 28; 27-35: *On the safety of a new generation of DSM Aspergillus niger enzyme production strains*. In van Dijck et al, an *Aspergillus niger* strain is described that comprises 7 amplified glucoamylase gene loci, i.e. 7 amplicons. Preferred host cells within this context are filamentous fungus host cells, preferably *A. niger* host cells, comprising two or more amplicons, preferably two or more ΔglaA amplicons (preferably comprising 3, 4, 5, 6, 7 ΔglaA amplicons) wherein the amplicon which has the highest frequency of gene conversion, has been adapted to have enhanced integration preference for the polynucleotide encoding a compound of interest compared to the amplicon it originates from. Adaptation of the amplicon can be performed according to any one of the methods described in WO2011/009700 (which is here fully incorporated by reference). An example of these host cells, described in WO2011/009700, are host cells comprising three ΔglaA amplicons being a BamHI truncated amplicon, a SalI truncated amplicon and a Bg/II truncated amplicon and wherein the BamHI amplicon has been adapted to have enhanced integration preference for a polynucleotide encoding a compound of interest compared to the BamHI amplicon it originates from. Host cells comprising two or more amplicons wherein one amplicon has been adapted to have enhanced integration preference for a polynucleotide encoding a compound of interest compared to the amplicon it originates from are hereafter referred as host cells comprising an adapted amplicon.

When the mutant microbial host cell according to the invention is a filamentous fungal host cell, the host cell according to the invention may additionally comprises a modification of Sec61. A preferred SEC61 modification is a modification which results in a one-way mutant of SEC61; i.e. a mutant wherein the de novo synthesized protein can enter the ER via SEC61, but the protein cannot leave the ER via SEC61. Such modifications are extensively described in WO2005/123763. In a preferred embodiment the mutant microbial host cell comprises a modification in a Sec61 as depicted in SEQ ID NO: 3 of WO2005/123763. Most preferably, the SEC 61 modification is the S376W mutation in which Serine 376 is replaced by Tryptophan in SEQ ID NO: 3 of WO2005/123763.

In a preferred embodiment, the mutant microbial host cell according to the invention comprises at least one polynucleotide coding for a compound of interest or at least one polynucleotide coding for a compound involved in the production of a compound of interest by the cell.

The compound of interest can be any biological compound. The biological compound may be biomass or a biopolymer or metabolite. The biological compound may be encoded by a single polynucleotide or a series of polynucleotides composing a biosynthetic or metabolic pathway or may be the direct result of the product of a single polynucleotide or products of a series of polynucleotides. The biological compound may be native to the host cell or heterologous.

The term "heterologous biological compound" is defined herein as a biological compound which is not native to the cell; or a native biological compound in which structural modifications have been made to alter the native biological compound.

The term "biopolymer" is defined herein as a chain (or polymer) of identical, similar, or dissimilar subunits (monomers). The biopolymer may be any biopolymer. The biopolymer may for example be, but is not limited to, a nucleic acid, polyamine, polyol, polypeptide (or polyamide), or polysaccharide.

The biopolymer may be a polypeptide. The polypeptide may be any polypeptide having a biological activity of interest. The term "polypeptide" is not meant herein to refer to a specific length of the encoded product and, therefore, encompasses peptides, oligopeptides, and proteins. Polypeptides further include naturally occurring allelic and engineered variations of the above-mentioned polypeptides and hybrid polypeptides. The polypeptide may be native or may be heterologous to the host cell. The polypeptide may be a collagen or gelatin, or a variant or hybrid thereof. The polypeptide may be an antibody or parts thereof, an antigen, a clotting factor, an enzyme, a hormone or a hormone variant, a receptor or parts thereof, a regulatory protein, a structural protein, a reporter, or a transport protein, protein involved in secretion process, protein involved in folding process, chaperone, peptide amino acid transporter, glycosylation factor, transcription factor, synthetic peptide or oligopeptide, intracellular protein. The intracellular protein may be an enzyme such as, a protease, ceramidases, epoxide hydrolase, aminopeptidase, acylases, aldolase, hydroxylase, aminopeptidase, lipase. The polypeptide may also be an enzyme secreted extracellularly. Such enzymes may belong to the groups of oxidoreductase, transferase, hydrolase, lyase, isomerase, ligase, catalase, cellulase, chitinase, cutinase, deoxyribonuclease, dextranase, esterase. The enzyme may be a carbohydrase, e.g. cellulases such as endoglucanases, β-glucanases, cellobiohydrolases or β-glucosidases, hemicellulases or pectinolytic enzymes such as xylanases, xylosidases, mannanases, galactanases, galactosidases, pectin methyl esterases, pectin lyases, pectate lyases, endo polygalacturonases, exopolygalacturonases rhamnogalacturonases, arabanases, arabinofuranosidases, arabinoxylan hydrolases, galacturonases, lyases, or amylolytic enzymes; hydrolase, isomerase, or ligase, phosphatases such as phytases, esterases such as lipases, proteolytic enzymes, oxidoreductases such as oxidases-transferases, or isomerases. The enzyme may be a phytase. The enzyme may be an aminopeptidase, asparaginase, amylase, a maltogenic amylase, carbohydrase, carboxypeptidase, endo-protease, metallo-protease, serine-protease catalase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, protein deaminase, invertase, laccase, lipase, mannosidase, mutanase, oxidase, pectinolytic enzyme, peroxidase, phospholipase, galactolipase, chlorophyllase, polyphenoloxidase, ribonuclease, transglutaminase, or glucose oxidase, hexose oxidase, monooxygenase.

Preferably the compound of interest is a glucose oxidase. According to the present invention, a polypeptide or enzyme also can be a product as described in WO2010/102982. According to the present invention, a polypeptide can also be a fused or hybrid polypeptide to which another polypeptide is fused at the N-terminus or the C-terminus of the polypeptide or fragment thereof. A fused polypeptide is produced by fusing a nucleic acid sequence (or a portion thereof) encoding one polypeptide to a nucleic acid sequence (or a portion thereof) encoding another polypeptide.

Techniques for producing fusion polypeptides are known in the art, and include, ligating the coding sequences encoding the polypeptides so that they are in frame and expression of the fused polypeptide is under control of the same promoter (s) and terminator. The hybrid polypeptides may comprise a combination of partial or complete polypeptide sequences obtained from at least two different polypeptides wherein one or more may be heterologous to the host cell. Example of fusion polypeptides and signal sequence fusions are for example as described in WO2010/121933.

The biopolymer may be a polysaccharide. The polysaccharide may be any polysaccharide, including, but not limited to, a mucopolysaccharide (e. g., heparin and hyaluronic acid) and nitrogen-containing polysaccharide (eg., chitin). In a more preferred option, the polysaccharide is hyaluronic acid.

The polynucleotide coding for the compound of interest or coding for a compound involved in the production of the compound of interest according to the invention may encode an enzyme involved in the synthesis of a primary or secondary metabolite, such as organic acids, carotenoids, (beta-lactam) antibiotics, and vitamins. Such metabolite may be considered as a biological compound according to the present invention.

The term "metabolite" encompasses both primary and secondary metabolites; the metabolite may be any metabolite. Preferred metabolites are citric acid, gluconic acid, adipic acid, fumaric acid, itaconic acid and succinic acid.

The metabolite may be encoded by one or more genes, such as in a biosynthetic or metabolic pathway. Primary metabolites are products of primary or general metabolism of a cell, which are concerned with energy metabolism, growth, and structure. Secondary metabolites are products of secondary metabolism (see, for example, R. B. Herbert, The Biosynthesis of Secondary Metabolites, Chapman and Hall, New York, 1981).

The primary metabolite may be, but is not limited to, an amino acid, fatty acid, nucleoside, nucleotide, sugar, triglyceride, or vitamin.

The secondary metabolite may be, but is not limited to, an alkaloid, coumarin, flavonoid, polyketide, quinine, steroid, peptide, or terpene. The secondary metabolite may be an antibiotic, antifeedant, attractant, bacteriocide, fungicide, hormone, insecticide, or rodenticide. Preferred antibiotics are cephalosporins and beta-lactams. Other preferred metabolites are exo-metabolites. Examples of exo-metabolites are Aurasperone B, Funalenone, Kotanin, Nigragillin, Orlandin, Other naphtho-γ-pyrones, Pyranonigrin A, Tensidol B, Fumonisin B2 and Ochratoxin A.

The biological compound may also be the product of a selectable marker. A selectable marker is a product of a polynucleotide of interest which product provides for biocide or viral resistance, resistance to heavy metals, protothrophy to auxotrophs, and the like. Selectable markers include, but are not limited to, amdS (acetamidase), argB (ornithinecarbamoyltransferase), bar (phosphinothricinacetyltransf erase), hygB (hygromycin phosphotransferase), niaD (nitrate reductase), pyrG (orotidine-5'-phosphate decarboxylase), sC (sulfate adenyltransferase), trpC (anthranilate synthase), ble (phleomycin resistance protein), hyg (hygromycin), NAT or NTC (Nourseothricin) as well as equivalents thereof.

According to the invention, the compound of interest is preferably a polypeptide as described in the list of compounds of interest.

Preferably, the polypeptide is an enzyme as described in the list of compounds of interest. Preferably a glucose oxidase.

According to another embodiment of the invention, the compound of interest is preferably a metabolite.

The mutant microbial cell may already be capable of producing the compound of interest. The mutant microbial host cell may also be provided with a homologous or heterologous nucleic acid construct that encodes a polypeptide wherein the polypeptide may be the compound of interest or a polypeptide involved in the production of the compound of interest. The person skilled in the art knows how to modify a microbial host cell such that it is capable of producing the compound of interest.

The term "nucleic acid construct" is herein referred to as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term "expression cassette" when the nucleic acid construct contains all the control sequences required for expression of a coding sequence, wherein said control sequences are operably linked to said coding sequence.

The term "operably linked" is defined herein as a configuration in which a control sequence is appropriately placed at a position relative to the coding sequence of the DNA sequence such that the control sequence directs the production of an RNA or an mRNA and optionally of a polypeptide translated from said (m)RNA.

The term "control sequences" is defined herein to include all components, which are necessary or advantageous for the expression of mRNA and/or a polypeptide, either in vitro or in a host cell. Each control sequence may be native or foreign to the nucleic acid sequence encoding the polypeptide. Such control sequences include, but are not limited to, a leader, Shine-Delgarno sequence, optimal translation initiation sequences (as described in Kozak, 1991, J. Biol. Chem. 266:19867-19870), a polyadenylation sequence, a pro-peptide sequence, a pre-pro-peptide sequence, a promoter, a signal sequence, and a transcription terminator. At a minimum, the control sequences include a promoter, and transcriptional and translational stop signals. Control sequences may be optimized to their specific purpose. Preferred optimized control sequences used in the present invention are those described in WO2006/077258, which is herein incorporated by reference.

The control sequences may be provided with linkers for the purpose of introducing specific restriction sites facilitating ligation of the control sequences with the coding region of the nucleic acid sequence encoding a polypeptide.

The control sequence may be an appropriate promoter sequence (promoter).

The control sequence may also be a suitable transcription terminator (terminator) sequence, a sequence recognized by a filamentous fungal cell to terminate transcription. The terminator sequence is operably linked to the 3'-terminus of the nucleic acid sequence encoding the polypeptide. Any terminator, which is functional in the cell, may be used in the present invention. The man skilled in the art knows which types of terminators can be used in the microbial host cell as described herein.

Preferred terminator sequences for filamentous fungal cells are obtained from any terminator sequence of a filamentous fungal gene, more preferably from *Aspergillus* genes, even more preferably from the gene *A. oryzae* TAKA amylase, the genes encoding *A. niger* glucoamylase (glaA), *A. nidulans* anthranilate synthase, *A. niger* alpha-glucosidase, trpC and/or *Fusarium oxysporum* trypsin-like protease.

The control sequence may also be an optimal translation initiation sequences (as described in Kozak, 1991, J. Biol. Chem. 266:19867-19870), or a 5'-untranslated sequence, a non-translated region of a mRNA which is important for translation by the mutated microbial host cell. The translation initiation sequence or 5'-untranslated sequence is operably linked to the 5'-terminus of the coding sequence encoding the polypeptide. Each control sequence may be native or foreign to the nucleic acid sequence encoding the polypeptide. Control sequences may be optimized to their specific purpose.

Suitable 5'-untranslated sequences may be those polynucleotides preceeding the fungal amyloglucosidase (AG) gene, *A. oryzae* TAKA amylase and *Aspergillus* triose phosphate isomerase genes and *A. niger* glucoamylase glaA, alpha-amylase, xylanase and phytase encoding genes.

The control sequence may also be a non-translated region of a mRNA which is important for translation by the mutated microbial host cell. The leader sequence is operably linked to the 5'-terminus of the nucleic acid sequence encoding the polypeptide. Any leader sequence, which is functional in the cell, may be used in the present invention.

Leader sequences may be those originating from the fungal amyloglucosidase (AG) gene (glaA-both 18 and 24 amino acid versions e. g. from *Aspergillus*), the α-factor gene (yeasts e. g. *Saccharomyces* and *Kluyveromyces*) or the α-amylase (amyE, amyQ and amyL) and alkaline protease aprE and natural protease genes (*Bacillus*), or signal sequences ad described in WO2010/121933.

Preferred leaders for filamentous fungal cells are obtained from the polynucleotides preceding *A. oryzae* TAKA amylase and *A. nidulans* triose phosphate isomerase and *A. niger* glaA and phytase Other control sequences may be isolated from the *Penicillium* IPNS gene, or pcbC gene, the beta tubulin gene. All the control sequences cited in WO 01/21779 are herewith incorporated by reference.

The control sequence may also be a polyadenylation sequence, a sequence which is operably linked to the 3'-terminus of the nucleic acid sequence and which, when transcribed, is recognized by the microbial host cell (mutated or parent) as a signal to add polyadenosine residues to transcribed mRNA. Any polyadenylation sequence, which is functional in the cell, may be used in the present invention.

Preferred polyadenylation sequences for filamentous fungal cells are obtained from the polynucleotides encoding *A. oryzae* TAKA amylase, *A. niger* glucoamylase, *A. nidulans* anthranilate synthase, *Fusarium oxysporum* trypsin-like protease and *A. niger* alpha-glucosidase.

In the mutant microbial host cell according to the invention the at least one polynucleotide coding for the compound of interest or the at least one polynucleotide coding for a compound involved in the production of a compound of interest may be operably linked to a promoter.

The term "promoter" is defined herein as a DNA sequence that binds RNA polymerase and directs the polymerase to the correct downstream transcriptional start site of a nucleic acid sequence encoding a biological compound to initiate transcription. RNA polymerase effectively catalyzes the assembly of messenger RNA complementary to the appropriate DNA strand of a coding region. The term "promoter" will also be understood to include the 5'-non-coding region (between promoter and translation start) for translation after transcription into mRNA, cis-acting transcription control elements such as enhancers, and other nucleotide sequences capable of interacting with transcription factors. The promoter may be any appropriate promoter sequence suitable for a eukaryotic or prokaryotic host cell, which shows transcriptional activity, including mutant, truncated, and hybrid promoters, and may be obtained from polynucleotides encoding extra-cellular or intracellular polypeptides either homologous (native) or heterologous (foreign) to the cell. The promoter may be a constitutive or inducible promoter.

The promoter may be an inducible promoter. The promoter may be a carbohydrate inducible promoter. Carbohydrate inducible promoters that can be used are a starch-, cellulose-, hemicellulose (such as xylan- and/or xylose-inducible) promoters. Other inducible promoters are copper-, oleic acid-inducible promoters. Promoters suitable in filamentous fungi are promoters which may be selected from the group, which includes but is not limited to promoters obtained from the polynucleotides encoding *A. oryzae* TAKA amylase, *Rhizomucor miehei* aspartic proteinase, *A. niger* neutral alpha-amylase, *A. niger* acid stable alphaamylase, *A. niger* or *A. awamori* glucoamylase (glaA), *A. niger* or *A. awamori* endoxylanase (xlnA) or beta-xylosidase (xlnD), *T. reesei* cellobiohydrolase I (CBHI), *R. miehei* lipase, *A. oryzae* alkaline protease, *A. oryzae* triose phosphate isomerase, *A. nidulans* acetamidase, *Fusarium venenatum* amyloglucosidase (WO 00/56900), *Fusarium venenatum* Dania (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the polynucleotides encoding *A. niger* neutral alpha-amylase and *A. oryzae* triose phosphate isomerase), and mutant, truncated, and hybrid promoters thereof. Other examples of promoters are the promoters described in WO2006/092396 and WO2005/100573, which are herein incorporated by reference. An even other example of the use of promoters is described in WO2008/098933. Promoters can also be constitutive promoters.

Examples of promoters from Gram-positive microorganisms include, but are not limited to, gnt (gluconate operon promoter); penP from *Bacillus licheniformis*; glnA (glutamine synthetase); xylAB (xylose operon); araABD (L-arabinose operon) and Pspac promoter, a hybrid SPO1/lac promoter that can be controlled by inducers such as isopropyl-β-D-thiogalactopyranoside [IPTG] ((Yansura D. G., Henner D. J. Proc Natl Acad Sci USA. 1984 81(2):439-443). Activators are also sequence-specific DNA binding proteins that induce promoter activity. Examples of such promoters from Gram-positive microorganisms include, but are not limited to, two-component systems (PhoP-PhoR, DegU-DegS, SpoOA-Phosphorelay), LevR, Mry and GltC. (ii) Production of secondary sigma factors can be primarily responsible for the transcription from specific promoters. Examples from Gram-positive microorganisms include, but are not limited to, the promoters activated by sporulation specific sigma factors: σF, σE, σG and σK and general stress sigma factor, σB. The σB-mediated response is induced by energy limitation and environmental stresses (Hecker M, Völker U. Mol Microbiol. 1998; 29(5):1129-1136). (iii) Attenuation and antitermination also regulates transcription. Examples from Gram-positive microorganisms include, but are not limited to, trp operon and sacB gene. (iv) Other regulated promoters in expression vectors are based the sacR regulatory system conferring sucrose inducibility (Klier A F, Rapoport G. Annu Rev Microbiol. 1988; 42:65-95).

Suitable inducible promoters useful in bacteria, such as Bacilli, include: promoters from Gram-positive microorganisms such as, but are not limited to, SP01-26, SP01-15, veg, pyc (pyruvate carboxylase promoter), and amyE. Examples of promoters from Gram-negative microorganisms include, but are not limited to, tac, tet, trp-tet, lpp, lac, lpp-lac, laclq, T7, T5, T3, gal, trc, ara, SP6, λ-PR, and λ-PL.

Additional examples of promoters useful in bacterial cells, such as Bacilli, include the α-amylase and SPo2 promoters as well as promoters from extracellular protease genes.

Other example of a suitable promoter are the promoter obtained from the *E. coli* lac operon. Another example is the promoter of the *Streptomyces coelicolor* agarase gene (dagA). Another example is the promoter of the *Bacillus lentus* alkaline protease gene (aprH). Another example is the promoter of the *Bacillus licheniformis* alkaline protease gene (subtilisin Carlsberg gene). Another example is the promoter of the *Bacillus subtilis* levansucrase gene (sacB). Another example is the promoter of the *Bacillus subtilis* alphaamylase gene (amyF). Another example is the promoter of the *Bacillus licheniformis* alphaamylase gene (amyL). Another example is the promoter of the *Bacillus stearothermophilus* maltogenic amylase gene (amyM). Another example is the promoter of the *Bacillus amyloliquefaciens* alpha-amylase gene (amyQ). Another example is a "consensus" promoter having the sequence TTGACA for the "-35" region and TATAAT for the "-10" region. Another example is the promoter of the *Bacillus licheniformis* penicillinase gene (penP). Another example are the promoters of the *Bacillus subtilis* xylA and xylB genes.

Preferably the promoter sequence is from a highly expressed gene. Examples of preferred highly expressed genes from which promoters may be selected and/or which are comprised in preferred predetermined target loci for integration of expression constructs, include but are not limited to genes encoding glycolytic enzymes such as triosephosphate isomerases (TPI), glyceraldehyde-phosphate dehydrogenases (GAPDH), phosphoglycerate kinases (PGK), pyruvate kinases (PYK or PKI), alcohol dehydrogenases (ADH), as well as genes encoding amylases, glucoamylases, proteases, xylanases, cellobiohydrolases, β-galactosidases, alcohol (methanol) oxidases, elongation factors and ribosomal proteins. Specific examples of suitable highly expressed genes include e. g. the LAC4 gene from *Kluyveromyces* sp., the methanol oxidase genes (AOX and MOX) from *Hansenula* and *Pichia*, respectively, the glucoamylase (glaA) genes from *A. niger* and *A. awamori*, the *A. oryzae* TAKA-amylase gene, the *A. nidulans* gpdA gene and the *T. reesei* cellobiohydrolase genes.

Promoters which can be used in yeast include e.g. promoters from glycolytic genes, such as the phosphofructokinase (PFK), triose phosphate isomerase (TPI), glyceraldehyde-3-phosphate dehydrogenase (GPD, TDH3 or GAPDH), pyruvate kinase (PYK), phosphoglycerate kinase (PGK) promoters from yeasts or filamentous fungi; more details about such promoters from yeast may be found in (WO 93/03159). Other useful promoters are ribosomal protein encoding gene promoters, the lactase gene promoter (LAC4), alcohol dehydrogenase promoters (ADHI, ADH4, and the like), and the enolase promoter (ENO). Other promoters, both constitutive and inducible, and enhancers or upstream activating sequences will be known to those of skill in the art. The promoters used in the host cells of the invention may be modified, if desired, to affect their control characteristics. Suitable promoters in this context include both constitutive and inducible natural promoters as well as engineered promoters, which are well known to the person skilled in the art. Suitable promoters in eukaryotic host cells may be GAL7, GAL10, or GAL1, CYC1, HIS3, ADH1, PGL, PH05, GAPDH, ADC1, TRP1, URA3, LEU2, ENO1, TPI1, and AOX1. Other suitable promoters include PDC1, GPD1, PGK1, TEF1, and TDH3

In order to facilitate expression, the polynucleotide encoding the polypeptide being the compound of interest or the polypeptide involved in the production of the compound of interest may be a synthetic polynucleotide. The synthetic polynucleotides may be optimized in codon use, preferably according to the methods described in WO2006/077258 and/or PCT/EP2007/055943 (published as WO2008/000632), which are herein incorporated by reference. PCT/EP2007/055943 addresses codon-pair optimization. Codon-pair optimization is a method wherein the nucleotide sequences encoding a polypeptide have been modified with respect to their codon-usage, in particular the codon-pairs that are used, to obtain improved expression of the nucleotide sequence encoding the polypeptide and/or improved production of the encoded polypeptide. Codon pairs are defined as a set of two subsequent triplets (codons) in a coding sequence.

In order to facilitate expression and/or translation, the polynucleotide encoding the polypeptide being the compound of interest or encoding the polypeptide involved in the production of the compound of interest may be comprised in an expression vector such that the gene encoding the polypeptide product is operably linked to the appropriate control sequences for expression and/or translation in vitro, or in the mutant microbial host cell.

The expression vector may be any vector (e.g., a plasmid or virus), which can be conveniently subjected to recombinant DNA procedures and can bring about the expression of the polynucleotide encoding the polypeptide. The choice of the vector will typically depend on the compatibility of the vector with the cell into which the vector is to be introduced. The vectors may be linear or closed circular plasmids. The vector may be an autonomously replicating vector, i. e., a vector, which exists as an extra-chromosomal entity, the replication of which is independent of chromosomal replication, e.g., a plasmid, an extra-chromosomal element, a mini-chromosome, or an artificial chromosome. An autonomously maintained cloning vector may comprise the AMA1-sequence (see e.g. Aleksenko and Clutterbuck (1997), Fungal Genet. Biol. 21: 373-397).

Alternatively, the vector may be one which, when introduced into the host cell, is integrated into the genome and replicated together with the chromosome(s) into which it has been integrated. The integrative cloning vector may integrate at random or at a predetermined target locus in the chromosomes of the host cell. In a preferred embodiment of the invention, the integrative cloning vector comprises a DNA fragment, which is homologous to a DNA sequence in a predetermined target locus in the genome of host cell for targeting the integration of the cloning vector to this predetermined locus. In order to promote targeted integration, the cloning vector is preferably linearized prior to transformation of the cell. Linearization is preferably performed such that at least one but preferably either end of the cloning vector is flanked by sequences homologous to the target locus. The length of the homologous sequences flanking the target locus is preferably at least 30 bp, preferably at least 50 bp, preferably at least 0.1 kb, even preferably at least 0.2 kb, more preferably at least 0.5 kb, even more preferably at least 1 kb, most preferably at least 2 kb. Preferably, the efficiency of targeted integration into the genome of the host cell, i.e. integration in a predetermined target locus, is increased by augmented homologous recombination abilities of the host cell.

Preferably, the homologous flanking DNA sequences in the cloning vector, which are homologous to the target locus, are derived from a highly expressed locus meaning that they are derived from a gene, which is capable of high expression level in the host cell. A gene capable of high expression level, i.e. a highly expressed gene, is herein defined as a gene whose mRNA can make up at least 0.5% (w/w) of the total cellular mRNA, e.g. under induced conditions, or alternatively, a gene whose gene product can make up at least 1% (w/w) of the total cellular protein, or, in case of a secreted gene product, can be secreted to a level of at least 0.1 g/l (as described in EP 357 127 B1).

A number of preferred highly expressed fungal genes are given by way of example: the amylase, glucoamylase, alcohol dehydrogenase, xylanase, glyceraldehyde-phosphate dehydrogenase or cellobiohydrolase (cbh) genes from *Aspergilli, Chrysosporium* or *Trichoderma*. Most preferred highly expressed genes for these purposes are a glucoamylase gene, preferably an *A. niger* glucoamylase gene, an *A. oryzae* TAKA-amylase gene, an *A. nidulans* gpdA gene, a *Trichoderma reesei* cbh gene, preferably cbh1, a *Chrysosporium lucknowense* cbh gene or a cbh gene from *P. chrysogenum*.

More than one copy of a nucleic acid sequence may be inserted into the mutated microbial host cell to increase production of the product (over-expression) encoded by said sequence. This can be done, preferably by integrating into its genome copies of the DNA sequence, more preferably by targeting the integration of the DNA sequence at one of the highly expressed loci defined in the former paragraph. Alternatively, this can be done by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent. To increase even more the number of copies of the DNA sequence to be over expressed the technique of gene conversion as described in WO98/46772 may be used.

The vector system may be a single vector or plasmid or two or more vectors or plasmids, which together contain the total DNA to be introduced into the genome of the host cell, or a transposon.

The vectors preferably contain one or more selectable markers, which permit easy selection of transformed cells. A selectable marker is a gene the product of which provides for biocide or viral resistance, resistance to heavy metals, prototrophy to auxotrophs, and the like. The selectable marker may be introduced into the cell on the expression vector as the expression cassette or may be introduced on a separate expression vector.

A selectable marker for use in a filamentous fungal cell may be selected from the group including, but not limited to, amdS (acetamidase), argB (ornithine carbamoyltransferase), bar (phosphinothricinacetyltransferase), bleA (phleomycin binding), hygB (hygromycinphosphotransferase), niaD (nitrate reductase), pyrG (orotidine-5'-phosphate decarboxylase), sC (sulfate adenyltransferase), NAT or NTC (Nourseothricin) and trpC (anthranilate synthase), as well as equivalents from other species. Preferred for use in an *Aspergillus* and *Penicillium* cell are the amdS (see for example EP 635574 B1, EP0758020A2, EP1799821A2, WO 97/06261A2) and pyrG genes of *A. nidulans* or *A. oryzae* and the bar gene of *Streptomyces hygroscopicus*. More preferably an amdS gene is used, even more preferably an amdS gene from *A. nidulans* or *A. niger*. A most preferred selectable marker gene is the *A. nidulans* amdS coding sequence fused to the *A. nidulans* gpdA promoter (see EP 635574 B1). Other preferred AmdS markers are those described in WO2006/040358. AmdS genes from other filamentous fungi may also be used (WO 97/06261).

Markers which can be used in bacteria include ATP synthetase, subunit 9 (oliC), orotidine-5'-phosphatedecarboxylase (pyrA), the bacterial G418 resistance gene (this may also be used in yeast, but not in filamentous fungi), the ampicillin resistance gene (*E. coli*), resistance genes for, neomycin, kanamycin, tetracycline, spectinomycin, erythromycin, chloramphenicol, phleomycin (*Bacillus*) and the *E. coli* uidA gene, coding for β-glucuronidase (GUS). Vectors may be used in vitro, for example for the production of RNA or used to transfect or transform a host cell.

Versatile marker genes that can be used for transformation of most filamentous fungi and yeasts such as acetamidase genes or cDNAs (the amdS, niaD, facA genes or cDNAs from *A. nidulans, A. oryzae* or *A. niger*), or genes providing resistance to antibiotics like G418, hygromycin, bleomycin, kanamycin, methotrexate, phleomycin orbenomyl resistance (benA). Alternatively, specific selection markers can be used such as auxotrophic markers which require corresponding mutant host strains: e. g. D-alanine racemase (from *Bacillus*), URA3 (from *S. cerevisiae* or analogous genes from other yeasts), pyrG or pyrA (from *A. nidulans* or *A. niger*), argB (from *A. nidulans* or *A. niger*) or trpC. In a preferred embodiment the selection marker is deleted from the transformed host cell after introduction of the expression construct so as to obtain transformed host cells capable of producing the polypeptide which are free of selection marker genes.

The procedures used to ligate the elements described above to construct the recombinant expression vectors of the present invention are well known to one skilled in the art (see, e.g. Sambrook & Russell, *Molecular Cloning: A Laboratory Manual*, 3rd Ed., CSHL Press, Cold Spring Harbor, N.Y., 2001; and Ausubel et al., *Current Protocols in Molecular Biology*, Wiley InterScience, NY, 1995).

Furthermore, standard molecular cloning techniques such as DNA isolation, gel electrophoresis, enzymatic restriction modifications of nucleic acids, Southern analyses, transformation of cells, etc., are known to the skilled person and are for example described by Sambrook et al. (1989) "Molecular Cloning: a laboratory manual", Cold Spring Harbor Laboratories, Cold Spring Harbor, N.Y. and Innis et al. (1990) "PCR protocols, a guide to methods and applications" Academic Press, San Diego.

A nucleic acid may be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis.

Preferably, the mutant microbial host cell is modified to improve the expression of the polynucleotides to enhance production of the polypeptides being the compound of interest or a polypeptide involved in the production of a compound of interest.

Preferably, the efficiency of targeted integration into the genome of the host cell, i.e. integration in a predetermined target locus, is increased by augmented homologous recombination abilities of the host cell. Such phenotype of the cell preferably involves a deficient hdfA or hdfB as described in WO2005/095624. WO2005/095624 discloses a preferred method to obtain a filamentous fungal cell comprising increased efficiency of targeted integration.

Optionally, the host cell has been modified to comprise an elevated unfolded protein response (UPR) to enhance production abilities of a polypeptide of interest. UPR may be increased by techniques described in US2004/0186070A1 and/or US2001/0034045A1 and/or WO01/72783A2 and/or WO2005/123763. More specifically, the protein level of HAC1 and/or IRE1 and/or PTC2 may be modulated, and/or the SEC61 protein may be engineered in order to obtain a host cell having an elevated UPR.

The person skilled in the art knows how to transform cells with the one or more expression cassettes and the selectable marker. For example, the skilled person may use one or more expression vectors, wherein the one or more cloning vectors comprise the expression cassettes and the selectable marker.

Transformation of the mutant microbial host cell may be conducted by any suitable known methods, including e.g. electroporation methods, particle bombardment or microprojectile bombardment, protoplast methods and *Agrobacterium* mediated transformation (AMT). Preferably the protoplast method is used. Procedures for transformation are described by J. R. S. Fincham, Transformation in fungi. 1989, Microbiological reviews. 53, 148-170.

Transformation of the mutant microbial host cell by introduction of a polynucleotide an expression vector or a nucleic acid construct into the cell is preferably performed by techniques well known in the art (see Sambrook & Russell; Ausubel, supra).

Transformation may involve a process consisting of protoplast formation, transformation of the protoplasts, and regeneration of the cell wall in a manner known per se. Suitable procedures for transformation of *Aspergillus* cells are described in EP 238 023 and Yelton et al., 1984, Proceedings of the National Academy of Sciences USA 81:1470-1474. Suitable procedures for transformation of *Aspergillus* and other filamentous fungal host cells using *Agrobacterium tumefaciens* are described in e.g. De Groot et al., *Agrobacterium tumefaciens*-mediated transformation of filamentous fungi. Nat Biotechnol. 1998, 16:839-842. Erratum in: Nat Biotechnol 1998 16:1074. A suitable method of transforming *Fusarium* species is described by Malardier et al., 1989, Gene 78:147156 or in WO 96/00787. Other methods can be applied such as a method using biolistic transformation as described in: Christiansen et al., *Biolistic transformation of the obligate plant pathogenic fungus, Erysiphe graminis fsp. hordei*. 1995, Curr Genet. 29:100-102. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al., 1983, Journal of Bacteriology 153: 163; and Hinnen et al., 1978, Proceedings of the National Academy of Sciences USA 75: 1920.

In order to enhance the amount of copies of the polynucleotide coding for the compound of interest or coding for a compound involved in the production by the cell of the compound of interest (the gene) in the mutated microbial host cell, multiple transformations of the host cell may be required. In this way, the ratios of the different enzymes produced by the host cell may be influenced. Also, an expression vector may comprise multiple expression cassettes to increase the amount of copies of the polynucleotide(s) to be transformed.

Another way could be to choose different control sequences for the different polynucleotides, which—depending on the choice—may cause a higher or a lower production of the desired polypeptide(s).

The cells transformed with the selectable marker can be selected based on the presence of the selectable marker. In case of transformation of (*Aspergillus*) cells, usually when the cell is transformed with all nucleic acid material at the same time, when the selectable marker is present also the polynucleotide(s) encoding the desired polypeptide(s) are present.

The invention also provides a method of producing a mutant microbial host cell according to the invention comprising the steps of:
  a. providing a parent microbial host cell as described herein;

b. modifying the parent microbial host cell, preferably modifying the genome of the parent microbial host cell, to yield a mutant microbial host cell as described herein which is deficient in the production of a polypeptide as described herein having amylase activity, preferably α-amylase activity selected from the group consisting of:
  i. a polypeptide according to SEQ ID NO: 3 or 7 or a polypeptide at least 70% identical thereto;
  ii. a mature polypeptide comprised in SEQ ID NO: 3 or 7 or a polypeptide at least 70% identical thereto
  iii. a polypeptide encoded by a polynucleotide according to SEQ ID NO: 1, 2, 5 or 6 or encoded by a polynucleotide at least 70% identical to SEQ ID NO: 1, 2, 5 or 6;
  iv. a polypeptide encoded by a polynucleotide capable of hybridising to a polynucleotide according to SEQ ID NO: 1, 2, 5 or 6 or capable of hybridising to the complementary strand of a polynucleotide according to SEQ ID NO: 1, 2, 5 or 6;
  if compared with the parent microbial host cell and measured under the same conditions.

Within this context it will be clear to those skilled in the art that the specific embodiments that may be applicable to the mutant microbial host cell according to the invention may also be applicable to the other aspects of the invention.

The invention further provides a method for the production of a compound of interest by microbial fermentation comprising:
  a. providing a mutant microbial host cell according to the invention capable of expressing the compound of interest,
  b. culturing said microbial host cell under conditions conducive to the expression of the compound of interest,
  c. optionally isolating the compound of interest from the culture medium.

In step a. a mutant microbial host cell may be a mutant host cell as described herein.

In step b. the mutant microbial host cell of step a. is cultured under conditions conducive to the expression of the compound of interest as described herein. The mutant microbial cells are cultivated in a nutrient medium suitable for production of the compound of interest using methods known in the art. For example, the cells may be cultivated by shake flask cultivation, small-scale or large-scale fermentation (including continuous, batch, fed-batch, or solid state fermentations) in laboratory or industrial fermentors performed in a suitable medium and under conditions allowing the compound of interest to be produced and/or isolated. The cultivation takes place in a suitable nutrient medium comprising carbon and nitrogen sources and inorganic salts, using procedures known in the art (see, e. g., Bennett, J. W. and LaSure, L., eds., *More Gene Manipulations in Fungi*, Academic Press, CA, 1991). Suitable media are available from commercial suppliers or may be prepared using published compositions (e. g., in catalogues of the American Type Culture Collection). If the compound of interest is secreted into the nutrient medium, the compound can be isolated directly from the medium. If the compound of interest is not secreted, it can be isolated from cell lysates.

In step c. the compound of interest may be optionally isolated. The compound of interest as described herein may be isolated by methods known in the art. For example, the compound of interest may be isolated from the nutrient medium by conventional procedures including, but not limited to, centrifugation, filtration, extraction, spray drying, evaporation, or precipitation. The isolated compound of interest may then be further purified by a variety of procedures known in the art including, but not limited to, chromatography (e. g., ion exchange, affinity, hydrophobic, chromatofocusing, and size exclusion), electrophoretic procedures (e.g., preparative isoelectric focusing), differential solubility (e. g., ammonium sulfate precipitation), or extraction (see, e.g., *Protein Purification*, J.-C. Janson and Lars Ryden, editors, VCH Publishers, New York, 1989). In some applications the compound of interest may be used without substantial isolation from the culture broth; separation of the culture medium from the biomass may be adequate. The method for producing a compound of interest according to the invention offers the great advantage that less purification steps to eliminate amylase enzymatic side activities may be necessary, making such a method economically attractive.

A mutant microbial host cell as defined herein may be used in the method for the production of a compound of interest of the invention.

The compound of interest produced in the method for the production of a compound of interest by microbial fermentation may be any compound of interest as described herein.

Preferred Embodiments of the Invention

1. A mutant microbial host cell which has been modified, preferably in its genome, to result in a deficiency in the production of a polypeptide having amylase activity, preferably α-amylase activity selected from the group consisting of:
  a. a polypeptide according to SEQ ID NO: 3 or 7 or a polypeptide at least 70% identical thereto;
  b. a mature polypeptide comprised in SEQ ID NO: 3 or 7 or a polypeptide at least 70% identical thereto;
  c. a polypeptide encoded by a polynucleotide according to SEQ ID NO: 1, 2, 5 or 6 or encoded by a polynucleotide at least 70% identical to SEQ ID NO: 1, 2, 5 or 6;
  d. a polypeptide encoded by a polynucleotide capable of hybridising to a polynucleotide according to SEQ ID NO: 1, 2, 5 or 6 or capable of hybridising to the complementary strand of a polynucleotide according to SEQ ID NO: 1, 2, 5 or 6;
  if compared with a parent microbial host cell which has not been modified and measured under the same conditions.

2. A mutant microbial host cell according to embodiment 1 wherein the mature polypeptide comprised in SEQ ID NO: 3 or 7 is a mature polypeptide according to SEQ ID NO: 4 or 8 respectively.

3. The mutant microbial host cell according to embodiment 1 or 2 wherein the modification comprises:
  a) a modification which results in a reduced or no production of a polypeptide having amylase activity, preferably α-amylase activity as defined in embodiment 1 a. to 1.d. if compared to the parent microbial host cell that has not been modified, when analysed under the same conditions; and/or
  b) a modification which results in a polypeptide, derived from a polypeptide as defined in embodiment 1 a. to 1 d., but with decreased or no amylase activity, preferably with decreased or no α-amylase activity as compared to the parent microbial host cell that has not been modified, when analysed under the same conditions.

4. The mutant microbial host cell according to any one of embodiments 1 to 3 wherein the mutant microbial host cell
  a. produces less polypeptide as defined in embodiment 1 a. to 1 d. or it produces no polypeptide as defined in embodiment 1 a. to 1 d if compared with the parent microbial host cell which has not been modified and measured under the same conditions; and/or b. produces a polypeptide derived from the polypeptide as defined in embodiment 1 a. to 1 d, but with decreased or no amylase activity, preferably with decreased or no α-amylase activity if compared to the parent microbial host cell that has not been modified, when analysed under the same conditions.

5. The mutant microbial host cell according to any one of embodiments 1 to 4 wherein the mutant microbial host cell produces 1% less polypeptide having amylase activity, preferably α-amylase activity as defined in embodiment 1 a. to 1 d. if compared with the parent microbial host cell which has not been modified and measured under the same conditions, at least 5% less, at least 10% less, at least 20% less, at least 30% less, at least 40% less, at least 50% less, at least 60% less, at least 70% less, at least 80% less, at least 90% less, at least 91% less, at least 92% less, at least 93% less, at least 94% less at least 95% less, at least 96% less, at least 97% less, at least 98% less, at least 99% less, or at least 99.9% less, preferably the mutant microbial host cell produces substantially no polypeptide as defined in embodiment 1 a. to 1 d. if compared with the parent microbial host cell which has not been modified and measured under the same conditions.

6. The mutant microbial host cell according to any one of embodiments 1 to 5 wherein the mutant microbial host cell produces a polypeptide derived from the polypeptide having amylase activity, preferably α-amylase activity as defined in embodiment 1 a. to 1 d. with 1% less (α-) amylase activity, if compared with the parent microbial host cell which has not been modified and measured under the same conditions, at least 5% less activity, at least 10% less activity, at least 20% less activity, at least 30% less activity, at least 40% less activity, at least 50% less activity, at least 60% less activity, at least 70% less activity, at least 80% less activity, at least 90% less activity, at least 91% less activity, at least 92% less activity, at least 93% less activity, at least 94% less activity, at least 95% less activity, at least 96% less activity, at least 97% less activity, at least 98% less activity, at least 99% less activity, or at least 99.9% less activity, preferably the mutant microbial host cell produces a polypeptide derived from a polypeptide as defined in embodiment 1 a. to 1 d. with substantially no (α-) amylase activity if compared with the parent microbial host cell which has not been modified and analysed under the same conditions.

7. The mutant microbial host cell according to any one of embodiments 1 to 6 wherein the modification in its genome is selected from:
a) a full or partial deletion of a polynucleotide as defined in embodiment 1 c. or 1 d.,
b) a full or partial replacement of a polynucleotide as defined in embodiment 1 c. or 1 d. with a polynucleotide sequence which does not code for a polypeptide as defined in claims 1 a. to 1 d. or which code for a partially or fully inactive form of a polypeptide as defined in embodiment 1 a. to 1 d.;
c) a disruption of a polynucleotide as defined in embodiment 1 c. or 1 d. by the insertion of one or more nucleotides in the polynucleotide sequence and consequent partial or full inactivation of the polypeptide as defined in embodiment 1 a. to 1 d.

8. The mutant microbial host cell according to any one of embodiments 1 to 7 wherein the modification which results in a reduced or no production of a polypeptide as defined in embodiment 1 a. to 1 d. is due to a reduced production of the mRNA encoding said polypeptide.

9. The mutant microbial host cell according to any one of embodiments 1 to 8 comprising at least one polynucleotide coding for a compound of interest or at least one polynucleotide coding for a compound involved in the production of a compound of interest.

10. The mutant microbial host cell according to embodiment 9 wherein the at least one polynucleotide coding for the compound of interest or the at least one polynucleotide coding for a compound involved in the production of a compound of interest is operably linked to a promoter.

11. The mutant microbial host cell according to any one of embodiments 1 to 10 which is a eukaryotic cell, more preferably a fungal cell, even more preferably the mutant microbial host cell is a filamentous fungus.

12. The mutant microbial host cell according to embodiment 11 which is a filamentous fungus selected from *Aspergillus, Acremonium, Myceliophthora, Thielavia Chrysosporium, Penicillium, Talaromyces, Rasamsonia, Fusarium* or *Trichoderma*, preferably a species of *Aspergillus niger, Aspergillus awamori, Aspergillus foetidus, Aspergillus sojae, Aspergillus fumigatus, Aspergillus oryzae, Acremonium alabamense, Myceliophthora thermophila, Thielavia terrestris, Chrysosporium lucknowense, Fusarium oxysporum, Rasamsonia emersonii, Talaromyces emersonii, Trichoderma reesei* or *Penicillium chrysogenum*.

13. The mutant microbial host cell according to any one of the preceding embodiments which has been modified, preferably in its genome, to result in a deficiency in the production of one or more of a polypeptide having glucoamylase glaA activity, a polypeptide having alpha-amylase amyBII activity, a polypeptide having ΔamyBI activity and a polypeptide having acid stable alpha-amylase amyA activity, preferably a cell which has been modified, preferably in its genome, to result in a deficiency in the production of glucoamylase glaA activity, a polypeptide having alpha-amylase amyBII activity, a polypeptide having ΔamyBI activity and a polypeptide having acid stable alpha-amylase amyA activity.

14. A method of producing a mutant microbial host cell comprising the steps of:
a. providing a parent microbial host cell;
b. modifying the parent microbial host cell, preferably modifying the genome of the parent microbial host cell, to yield a mutant microbial host cell which is deficient in the production of a polypeptide having amylase activity, preferably α-amylase activity selected from the group consisting of:
i. a polypeptide according to SEQ ID NO: 3 or 7 or a polypeptide at least 70% identical thereto;
ii. a mature polypeptide comprised in SEQ ID NO: 3 or 7 or a polypeptide at least 70% identical thereto;
iii. a polypeptide encoded by a polynucleotide according to SEQ ID NO: 1, 2, 5 or 6 or encoded by a polynucleotide at least 70% identical to SEQ ID NO: 1, 2, 5 or 6;
iv. a polypeptide encoded by a polynucleotide capable of hybridising to the polynucleotide according to SEQ ID NO: 1, 2, 5 or 6 or capable of hybridising to the complementary strand of a polynucleotide according to SEQ ID NO: 1, 2, 5 or 6;
if compared with the parent microbial host cell and measured under the same conditions.

15. The method according to embodiment 14 wherein the mutant microbial host cell is a mutant microbial host cell according to any one of embodiments 1 to 13.

16. A method for the production of a compound of interest by microbial fermentation comprising:
   a. providing a mutant microbial host cell according to any one of embodiments 1 to 13 or produced by a method according to embodiments 14 or 15 capable of expressing the compound of interest,
   b. culturing said mutant microbial host cell under conditions conducive to the expression of the compound of interest,
   c. optionally isolating the compound of interest from the culture medium.
17. The method according to embodiment 16 wherein the compound of interest is a biological compound selected from the group consisting of biomass, a biopolymer, a metabolite, preferably the compound of interest is selected from a biopolymer or a metabolite.
18. The method according to embodiment 17 wherein the biopolymer is selected from a nucleic acid, a polyamine, a polyol, a polypeptide (such as a protein, preferably an enzyme) or a polyamide, or a polysaccharide or a metabolite is selected from a primary or secondary metabolite.
19. The method according to embodiment 18 wherein the compound of interest is an enzyme, preferably glucose oxidase.

Hereafter the invention will be illustrated by examples which however should not be interpreted as limiting the scope of the invention.

EXAMPLES

Strains

WT 1: This *Aspergillus niger* strain is used as a wild-type strain. This strain is deposited at the CBS Institute under the deposit number CBS 513.88.

GBA 306: The construction of GBA 306 using WT1 as starting strain has been described in detail in WO2011/009700. This GBA 306 strain has the following genotype: ΔglaA, ΔpepA, ΔhdfA, an adapted BamHI amplicon, ΔamyBII, ΔamyBI, and ΔamyA.

PGOX-2: This *A. niger* strain is a GBA306 strain expressing the *Penicillium chrysogenum* glucose oxidase enzyme. The PGOX-2 strain was constructed using the pGBTOP-GOX-3 expression vector (see FIG. 1—pGBTOP12 expression vector (WO2011/009700) with a codon pair optimized *Penicillium chrysogenum* glucose oxidase (as depicted in SEQ ID NO: 29 of WO2012/001169) coding sequence cloned in), which was introduced by co-transformation with the amdS selectable marker-gene containing vector pGBAAS-3 using the method as described in WO2011/009700 and WO2012/001169. After transformation and counter-selection (as also described in WO98/46772 and WO99/32617), followed by selection of strains with multiple copies, 1 multi-copy enzyme-producing strain was selected and named PGOX-2. This strain is used as the glucose oxidase enzyme producing strain in subsequent experiments.

Molecular Biology Techniques

In these strains, using molecular biology techniques known to the skilled person (see: Sambrook & Russell, *Molecular Cloning: A Laboratory Manual*, 3rd Ed., CSHL Press, Cold Spring Harbor, N.Y., 2001), several genes were over expressed and others were down regulated as described below. Examples of the general design of expression vectors for gene over expression and disruption vectors for down-regulation, transformation, use of markers and selective media can be found in WO199846772, WO199932617, WO2001121779, WO2005095624, WO2006040312, EP 635574B, WO2005100573, WO2011009700 and WO2012001169. All gene replacement vectors comprise approximately 1-2 kb flanking regions of the respective ORF sequences, to target for homologous recombination at the predestined genomic loci. In addition, they contain the *A. nidulans* bi-directional amdS selection marker for transformation, in-between direct repeats. The method applied for gene deletion in all examples herein uses linear DNA, which integrates into the genome at the homologous locus of the flanking sequences by a double cross-over, thus substituting the gene to be deleted by the amdS gene. After transformation, the direct repeats allow for the removal of the selection marker by a (second) homologous recombination event. The removal of the amdS marker can be done by plating on fluoro-acetamide media, resulting in the selection of marker-gene-free strains. Using this strategy of transformation and subsequent counter-selection, which is also described as the "MARKER-GENE FREE" approach in EP 0 635 574, the amdS marker can be used indefinitely in strain modification programs.

*A. niger* Shake Flask Fermentations

*A. niger* strains were pre-cultured and cultured at 34° C. and 170 rpm as described in WO2010/102982. Pre-culture was in 20 ml CSL pre-culture medium and after overnight growth 10 ml of this culture was transferred to 100 ml fermentation medium (FM) as described in more detail in WO2010/102982 with a cultivation time as indicated in the examples.

Enzyme Activity Measurements

Glucose oxidase (GOX) activity and the GOX activity plate assay (using o-anisidine) were measured as described in Witteveen et al. 1990, "Glucose oxidase overproducing and negative mutants of *Aspergillus niger*", Appl Microbiol Biotechnol 33:683-686.

Fungal alpha-amylase measurement was determined in *A. niger* culture broth, using the Megazyme cereal alpha-amylase kit (Megazyme, CERALPHA alpha amylase assay kit, catalogus. ref. K-CERA, year 2000-2001), according to basic instructions of the supplier with some modifications. The measured activity is based on hydrolysis of non-reducing-end-blocked ρ-nitrophenyl maltoheptaoside in the presence of excess glucoamylase and α-glucosidase. The amount of formed ρ-nitrophenol is a measure for alpha-amylase activity present in a sample. To make this assay sensitive for the amount of enzyme present in the culture samples, the following setup for measurement was used in the assay: 20 μl culture sample was mixed with 90 μl substrate solution (Ceralpha reagent), dissolved in 10 ml water with 8 ml of buffer added). Incubation was done for one hour at 37° C., after which the reaction was stopped with 20 μl 0.635 M Tris and measurement of the absorption at 405 nm. Activity was calculated using an enzymatic Fungal Amylase standard in the range of 0.00005-0.0005 FAUs/ml (Amylase enzyme was diluted in 50 mM malic acid buffer pH 5.2 (50 mM NaCl, 2 mM CaCl2, 0.05% BSA).

Example 1

Construction Approach of *Aspergillus* Niger PGOX-2 Strains, Containing Glycoside Hydrolase Gene Deletions To be able to disrupt the glycoside hydrolase (GH)-related genes (also known under the gene codes: An01g10930, An04g06920, and An04g06930 encoding amylase and/or (putative) alpha-glucosidase enzymes), a gene replacement vector was designed for each of the three genes as described above. Details of the amylase encoding genes can be found in Table 1.

TABLE 1

Gene and strain details for respective GH disruption strain constructed

| Strain code for disruption strain | Amy gene disrupted | Disruption vector | PCR results amdS | Amy gene |
|---|---|---|---|---|
| PGOX-2 | — | — | − | − |
| PGOX-2_AMY1 | AgdB - An01g10930 | pGBDEL-AMY1 | + | − |
| PGOX-2_AMY2 | AgdA - An04g06920 | pGBDEL-AMY2 | + | − |
| PGOX-2_AMY3 | AmyC - An04g06930 | pGBDEL-AMY3 | + | − |

Figure 2:
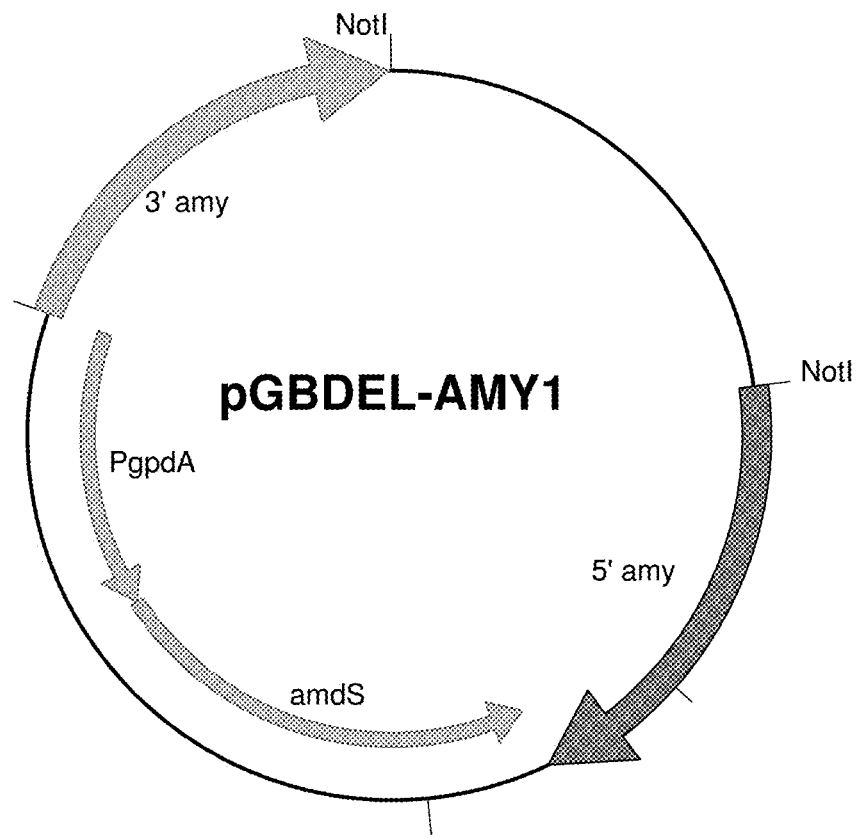
FIG. 2 depicts pGBDEL-AMY1, the plasmid used for deletion of the amylase encoding agoB gene with a layout representative for other deletion constructs (i.e. pGBDEL-AMY2 and pGBDEL-AMY3).

Vector pGBDEL-AMY1 (FIG. 2) and the other pGBDEL variants, which comprise approximately 1 kb flanking regions of the respective amylase encoding ORF's for homologous recombination, were used to transform *Aspergillus niger* PGOX-2. After verification of the truthful recombination events and correctness of the strains, the resulting correct strains PGOX-2, PGOX-2_AMY1, PGOX-2_AMY2, PGOX-2_AMY3-1, and PGOX-2_AMY3-2, were selected as representative strains with the respective amy genes (Table 1) inactivated in the PGOX-2 strain background.

Example 2

Figure 3:
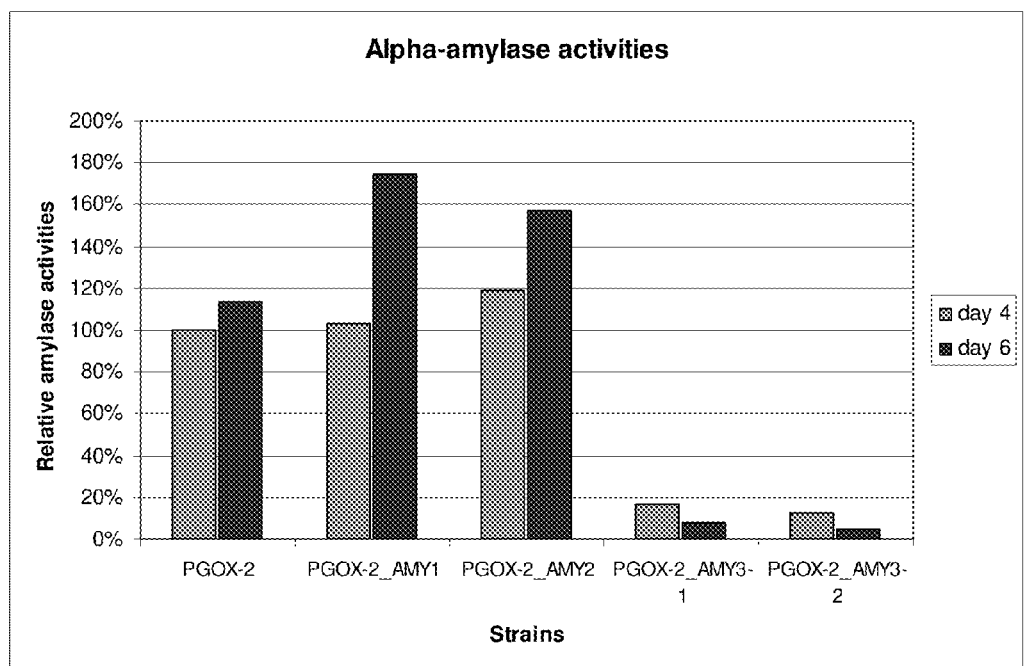
FIG. 3 depicts relative alpha-amylase activities, as measured in the culture supernatant of the different strains. The activity of the PGOX-2 reference strain at day 4 was set at a level of 100%.

Analysis of the *A. niger* PGOX-2 Derived Strains for the Amount of Glucose Oxidase Enzyme Product Produced To be able to assess the effect of the GH gene disruptions, shake-flask analysis in FM1 medium of these transformants was analysed. At day 4 and 6 after inoculation, medium samples were taken. Both the alpha-amylase activities and the glucose oxidase levels were analysed in the culture supernatant. In the PGOX-2 based strain background, the most important and abundant amylases, being glucoamylase glaA, alpha-amylase amyBII and ΔamyBI and acid stable alpha-amylase amyA were already disrupted. Surprisingly, upon disruption of AmyC-An04g06930, the alpha-amylase activity was reduced dramatically in PGOX-2_AMY3-1 and PGOX-2_AMY3-2 strains, whereas the other amy disruptions showed no pronounced effect in alpha-amylase activity (FIG. 3). This means that specifically amyC-An04g06930 disruption results in an important reduction in alpha-amylase activity.

Figure 4:
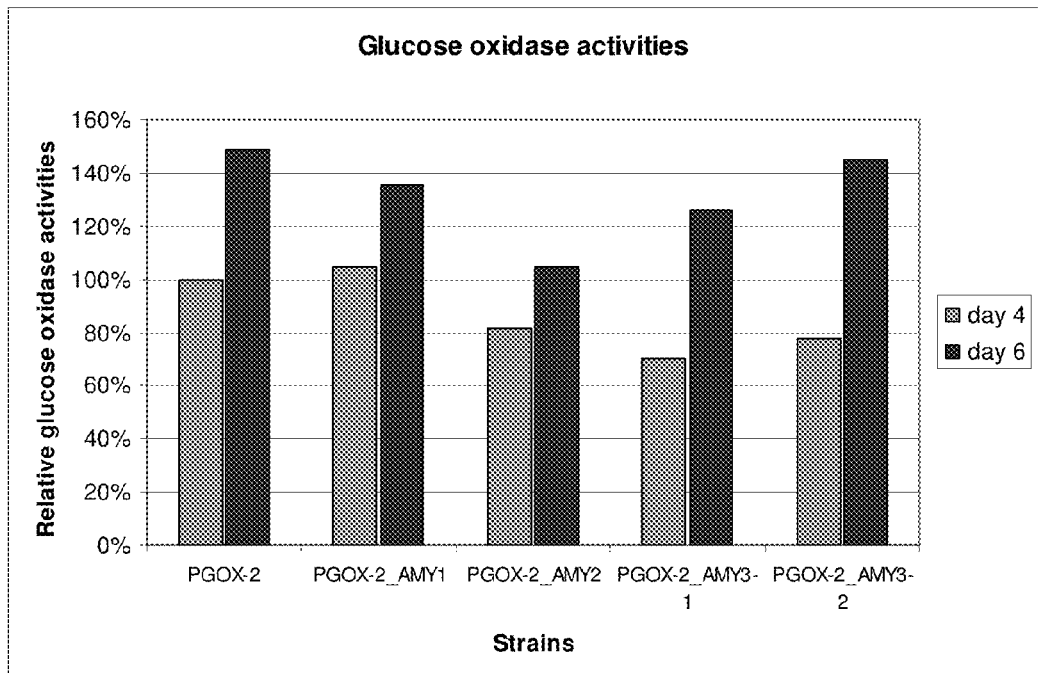
FIG. 4 depicts relative glucose oxidase activities, as measured in the culture supernatant of the different strains. The activity of the PGOX-2 reference strain at day 4 was set at a level of 100%.
Figure 5:
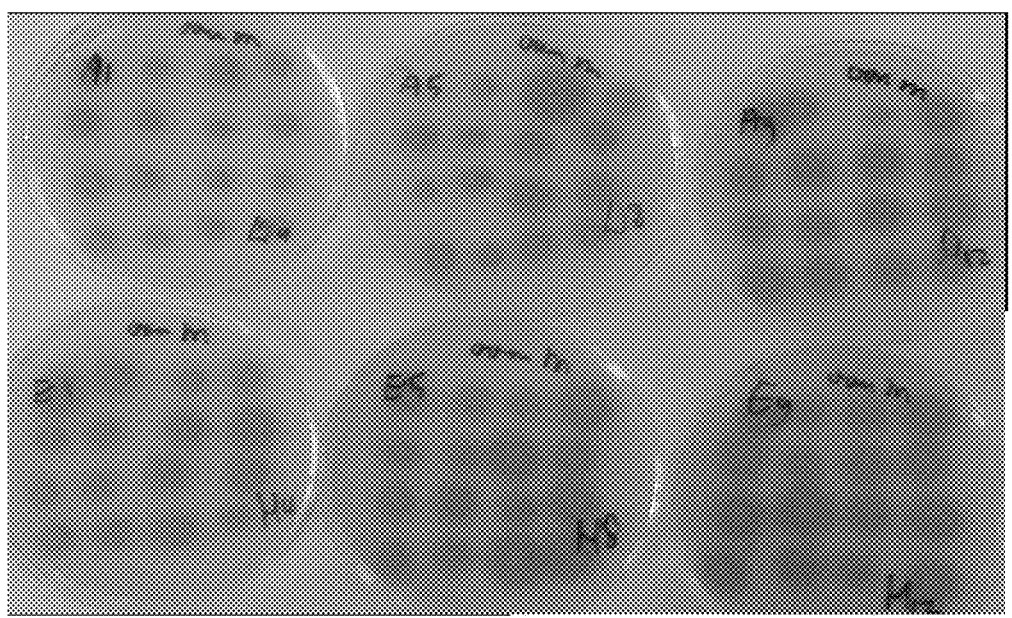
FIG. 5 depicts glucose oxidase activities on plate of the different mutant strains. Growth was on 1% maltose and staining with o-anisidine was done after 4 days of growth.

For glucose oxidase production, (FIG. 4) it can be seen that both the PGOX-2_AMY3-1 and PGOX-2_AMY3-2 strain, as identified from glucose oxidase activities in the culture supernatant, had an activity on both sampling days (day 4 and 6) comparable with the original strain. This was confirmed by analyzing GOX expression on plate (FIG. 5) for random transformants, which were isolated as described in Example 1.

The invention claimed is:

1. A mutant microbial host cell which has been modified to result in a deficiency in production of a polypeptide having α-amylase activity selected from the group consisting of:
   a. a polypeptide according to SEQ ID NO: 3 or 7 or a polypeptide at least 90% identical thereto;
   b. a mature polypeptide comprised in SEQ ID NO: 3 or 7 or a polypeptide at least 90% identical thereto;
   c. a polypeptide encoded by a polynucleotide according to SEQ ID NO: 1, 2, 5 or 6 or encoded by a polynucleotide at least 90% identical to SEQ ID NO: 1, 2, 5 or 6;
   d. a polypeptide encoded by a polynucleotide capable of hybridising to a polynucleotide according to SEQ ID NO: 1, 2, 5 or 6 or capable of hybridising to the complementary strand of a polynucleotide according to SEQ ID NO: 1, 2, 5 or 6;
   wherein the modification comprises a modification which results in a reduced or no production of a polypeptide having α-amylase activity as defined in a)-d) compared to the parent microbial host cell that has not been modified;
   wherein the modification is made in the genome of the microbial host cell;
   wherein the modification is selected from the group consisting of:
   1) a full or partial deletion of a polynucleotide as defined in c) or d);
   2) a full or partial replacement of a polynucleotide as defined in c) or d) with a polynucleotide sequence which does not code for a polypeptide as defined in a)-d) or which code for a partially or fully inactive form of a polypeptide as defined in a)-d);
   3) a disruption of a polynucleotide as defined in c) or d) by the insertion of one or more nucleotides in the polynucleotide sequence and consequent partial or full inactivation of the polypeptide as defined in a)-d);
   wherein the mutant microbial host cell is an *Aspergillus niger* cell; wherein the mutant microbial host cell has been further modified to result in a deficiency in the production of at least one of a polypeptide selected from the group consisting of: a polypeptide having glucoamylase glaA activity, a polypeptide having alpha-amylase amyBII activity, a polypeptide having amyBI activity, and a polypeptide having acid stable alpha-amylase amyA activity, if compared with a parent microbial host cell which has not been modified and measured under the same conditions.

2. A mutant microbial host cell according to claim 1, wherein the mature polypeptide comprised in SEQ ID NO: 3 or 7 is a mature polypeptide according to SEQ ID NO: 4 or 8.

3. The mutant microbial host cell according to claim 1, wherein the mutant microbial host cell
   1) produces less of the polypeptide having α-amylase activity or produces none of the polypeptide having a-amylase activity compared with the parent microbial host cell which has not been modified and measured under the same conditions; and/or
   2) produces a polypeptide derived from the polypeptide as defined in a) to d), but with decreased or no α-amylase activity if compared to the parent microbial host cell that has not been modified, when analysed under the same conditions.

4. The mutant microbial host cell according to claim 1, wherein the mutant microbial host cell produces 1% less polypeptide having α-amylase activity as defined in a) to d) compared with the parent microbial host cell which has not been modified and measured under the same conditions.

5. The mutant microbial host cell according to claim 1, wherein the mutant microbial host cell produces a polypeptide derived from the polypeptide having α-amylase activity with at least 1% less α-amylase activity, if compared with the parent microbial host cell which has not been modified and measured under the same condition.

6. The mutant microbial host cell according to claim 1, wherein a modification which results in a reduced or no production of the polypeptide having α-amylase activity is due to a reduced production of mRNA encoding said polypeptide.

7. The mutant microbial host cell according to claim 1, further comprising at least one polynucleotide coding for a compound of interest or at least one polynucleotide coding for a compound involved in the production of a compound of interest.

8. The mutant microbial host cell according to claim 7, wherein the at least one polynucleotide coding for the compound of interest or the at least one polynucleotide coding for a compound involved in the production of a compound of interest is operably linked to a promoter.

9. The mutant microbial host cell according to claim 1 which has been modified to result in a deficiency in production of glucoamylase glaA activity, a polypeptide having alpha-amylase amylase amyBII activity, a polypeptide having ΔamyBI activity and a polypeptide having acid stable alpha-amylase amyA activity.

10. A method of producing a mutant microbial host cell comprising:
   a. providing a parent microbial host cell;
   b. modifying the parent microbial host cell, optionally modifying the genome of the parent host cell, to yield a mutant host cell which is deficient in the production of a polypeptide having α-amylase activity selected from the group consisting of:
      i. a polypeptide according to SEQ ID NO: 3 or 7 or a polypeptide at least 90% identical thereto;
      ii. a mature polypeptide comprised in SEQ ID NO: 3 or 7 or a polypeptide at least 90% identical thereto;
      iii. a polypeptide encoded by a polynucleotide according to SEQ ID NO: 1, 2, 5 or 6 or encoded by a polynucleotide at least 90% identical to SEQ ID NO: 1, 2, 5 or 6;
      iv. a polypeptide encoded by a polynucleotide capable of hybridising to the polynucleotide according to SEQ ID NO: 1, 2, 5 or 6 or capable of hybridising to the complementary strand of a polynucleotide according to SEQ ID NO: 1, 2, 5 or 6;
   wherein the modification comprises a modification which results in a reduced or no production of a polypeptide having α-amylase activity as defined in a)-d) compared to the parent microbial host cell that has not been modified;
   wherein the modification is made in the genome of the microbial host cell;
   wherein the modification is selected from the group consisting of:
   1) a full or partial deletion of a polynucleotide as defined in c) or d);
   2) a full or partial replacement of a polynucleotide as defined in c) or d) with a polynucleotide sequence which does not code for a polypeptide as defined in a)-d) or which code for a partially or fully inactive form of a polypeptide as defined in a)-d);
   3) a disruption of a polynucleotide as defined in c) or d) by the insertion of one or more nucleotides in the polynucleotide sequence and consequent partial or full inactivation of the polypeptide as defined in a)-d);
      wherein the mutant microbial host cell is an *Aspergillus niger* cell; wherein the mutant microbial host cell has been modified to result in a deficiency in the production of at least one of a polypeptide selected from the group consisting of: a polypeptide having glucoamylase glaA activity, a polypeptide having alpha-amylase amyBII activity, a polypeptide having amyBI activity, and a polypeptide having acid stable alpha-amylase amyA activity, if compared with the parent microbial host cell and measured under the same conditions.

11. A method for production of a compound of interest by microbial fermentation comprising:
   a. providing a mutant microbial host cell according to claim 1 capable of expressing the compound of interest,
   b. culturing said mutant microbial host cell under conditions conducive to expression of the compound of interest,
   c. optionally isolating the compound of interest from a culture medium.

12. The method according to claim 11 wherein the compound of interest is a biological compound selected from the group consisting of biomass, a biopolymer, a metabolite, preferably the compound of interest is selected from a biopolymer or a metabolite.

13. The method according to claim 12, wherein the biopolymer is selected from a nucleic acid, a polyamine, a polyol, a polypeptide, a protein, optionally an enzyme or a polyamide, or a polysaccharide or a metabolite is selected from a primary or secondary metabolite.

14. The method according to claim 13, wherein the compound of interest is an enzyme.

15. The mutant microbial host cell according to claim 4, wherein the mutant microbial host cell produces at least 95% less polypeptide having α-amylase activity as defined in a) to d) compared with the parent microbial host cell which has not been modified and measured under the same conditions.

16. The mutant microbial host cell according to claim 5, wherein the mutant microbial host cell produces a polypeptide derived from the polypeptide having α-amylase activity with at least 95% less α-amylase activity, if compared with the parent microbial host cell which has not been modified and measured under the same conditions.

17. The method according to claim 14, wherein the enzyme is a glucose oxidase.

* * * * *